(12) United States Patent
David et al.

(10) Patent No.: US 8,012,220 B2
(45) Date of Patent: Sep. 6, 2011

(54) SPECIFIC MONOCATIONIC MONOCHROMOPHORIC COMPOUNDS OF HYDRAZONE TYPE COMPRISING A 2-, 4-PYRIDINIUM OR 2-, 4-QUINOLINIUM UNIT, SYNTHESIS THEREOF, DYE COMPOSITIONS CONTAINING THEM, AND METHOD FOR DYEING KERATIN FIBRES

(75) Inventors: Hervé David, La Varenne Saint Hilaire (FR); Nadège Murguet, Palaiseau (FR); Andrew Greaves, Montevrain (FR)

(73) Assignee: L'Oreal S.A., Paris (FR)

( * ) Notice: Subject to any disclaimer, the term of this patent is extended or adjusted under 35 U.S.C. 154(b) by 0 days.

(21) Appl. No.: 12/296,721

(22) PCT Filed: Apr. 13, 2007

(86) PCT No.: PCT/FR2007/051111
§ 371 (c)(1), (2), (4) Date: Jul. 13, 2009

(87) PCT Pub. No.: WO2007/125238
PCT Pub. Date: Nov. 8, 2007

(65) Prior Publication Data
US 2009/0300856 A1   Dec. 10, 2009

Related U.S. Application Data

(60) Provisional application No. 60/796,516, filed on May 2, 2006.

(30) Foreign Application Priority Data

Apr. 13, 2006 (FR) .................................. 06 03322

(51) Int. Cl.
*A61Q 5/10* (2006.01)
*C07D 211/02* (2006.01)

(52) U.S. Cl. ............. 8/405; 8/406; 8/408; 8/423; 8/435; 8/568; 546/249

(58) Field of Classification Search ............... 8/405, 406, 8/408, 423, 435, 568; 546/249
See application file for complete search history.

(56) References Cited

U.S. PATENT DOCUMENTS 4,424,349 A * 1/1984 Giesecke .......................... 546/9
6,001,135 A  12/1999 Rondeau et al.
6,712,861 B2   3/2004 Rondeau

FOREIGN PATENT DOCUMENTS

| EP | 0 850 638 B1 | 7/1998 |
|---|---|---|
| EP | 1 172 082 B1 | 1/2002 |
| EP | 1 437 123 B1 | 7/2004 |
| GB | 924 601 | 4/1963 |
| WO | WO 95/01772 | 1/1995 |
| WO | WO 03/060015 A1 | 7/2003 |
| WO | WO 2004/072183 A1 | 8/2004 |

OTHER PUBLICATIONS

STIC Search Report dated Dec. 13, 2010.*
International Search Report for PCT/FR2007/051111, dated Sep. 13, 2007.
English language abstract of EP 1 172 082 B1, Jun. 16, 2002.

* cited by examiner

*Primary Examiner* — Eisa B Elhilo
(74) *Attorney, Agent, or Firm* — Finnegan, Henderson, Farabow, Garrett & Dunner, LLP

(57) ABSTRACT

The present disclosure relates to monocationic monochromophoric compounds of formula (I) and (II) and dyeing compositions and multicompartment devices comprising monocationic monochromophoric compounds of formula (I) and (II). The disclosure also relates to methods for preparing monocationic monochromophoric compounds of formula (I) and (II), and also to methods for dyeing comprising applying monocationic monochromophoric compounds of formula (I) and (II) to keratin fibers.

10 Claims, No Drawings

SPECIFIC MONOCATIONIC MONOCHROMOPHORIC COMPOUNDS OF HYDRAZONE TYPE COMPRISING A 2-, 4-PYRIDINIUM OR 2-, 4-QUINOLINIUM UNIT, SYNTHESIS THEREOF, DYE COMPOSITIONS CONTAINING THEM, AND METHOD FOR DYEING KERATIN FIBRES

CROSS REFERENCE TO RELATED APPLICATIONS

This application is a National Phase application based on PCT/FR2007/051111 filed on Apr. 13, 2007, the contents of which are incorporated herein by reference and claims the priority of French Application No. 0603322, filed on Apr. 13, 2006, and the benefit of U.S. Provisional Application No. 60/796,516, filed on May 2, 2006, the contents of both of which are incorporated herein by reference.

One subject of the present invention is specific monocationic monochromophoric dyes of hydrazone type of specific formula comprising a 2- or 4-pyridinium or 2- or 4-quinolinium unit, dyeing compositions comprising, in a medium suitable for dyeing keratin fibres, such compounds as direct dye, a method for dyeing keratin fibres that uses this composition, and also a multicompartment device. It also relates to a method for synthesizing such compounds.

It is known practice to dye keratin fibres, and in particular human keratin fibres such as the hair, with dyeing compositions containing direct dyes. These compounds are coloured and colouring molecules that have a certain affinity for the fibres. It is, for example, known practice to use direct dyes of nitrobenzene type, anthraquinone dyes, nitropyridines, azo, xanthene, acridine, azine or triarylmethane type dyes or else aromatic direct dyes comprising a hydrazone functional group.

Direct dyes having a hydrazone functional group are interesting compounds but they have the drawback, in the majority of cases, of only allowing shades ranging from yellow to orange to be attained. In very rare cases, dyes having a hydrazone functional group provide other shades. For example, the hydrazone-type dyes with an acridinium unit from Patent GB924601 provide violet shades, the hydrazone-type dyes with a 2-oxopyrimidinium unit from Patent FR1532806 provide shades ranging from yellow to violet.

However, these dyes are unstable under alkaline and lightening conditions. They also exhibit a poor resistance to repeated shampooings.

It has surprisingly been discovered that it was possible to substantially extend the range of colours capable of being obtained from this family of direct dyes, these dyes being stable under alkaline lightening conditions. Thus, the compounds according to the invention make it possible to obtain shades ranging through to violet. To obtain such a variation was a priori far from being obvious since the known hydrazone-type dyes have a colour that varies relatively little even when the nature of the group borne by the aromatic ring and located in the para position with respect to the hydrazone functional group changes from a hydrogen atom to a halogen atom, or else to an alkoxy group.

These objectives and others are achieved by the present invention, the subject of which is therefore monocationic monochromophoric compounds comprising a hydrazone functional group of formulae (I) and (II) below, mesomeric forms thereof and also addition salts thereof with an acid and solvates thereof:

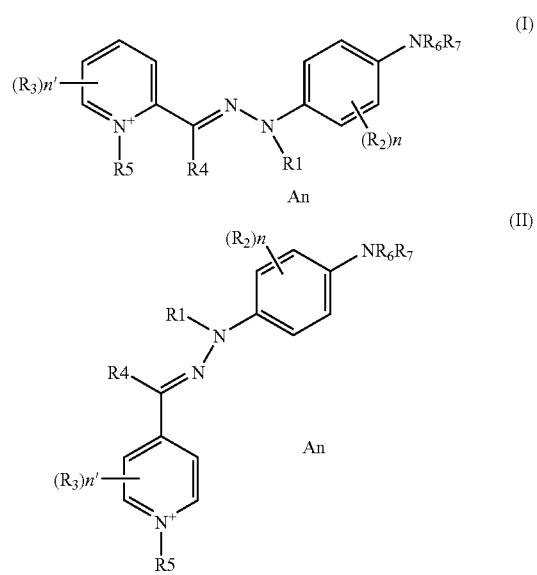

in which formulae (I) and/or (II):
the $R_1$ radical represents:
  a hydrogen;
  an optionally substituted $C_1$-$C_{20}$ alkyl radical, optionally interrupted by one or more heteroatoms and/or by one or more groups comprising at least one heteroatom, preferably chosen from oxygen, nitrogen, sulphur, CO, SO and $SO_2$, or combinations thereof; the alkyl radical not comprising any nitro, nitroso, peroxo or diazo functional groups;
  an optionally substituted phenyl radical;
  an optionally substituted benzyl radical;
  an alkylcarbonyl radical (R—CO—) in which R represents a $C_1$-$C_4$ alkyl radical;
  an alkylsulphonyl radical ($RSO_2$—) in which R represents a $C_1$-$C_4$ alkyl radical;
  an arylsulphonyl radical ($R'SO_2$—) in which R' represents an optionally substituted phenyl or benzyl radical;
  a (di)(alkyl)aminosulphonyl radical $((R)_2N$—$SO_2$—$)$ in which the R radicals independently represent a hydrogen or a $C_1$-$C_4$ alkyl radical;
  a (di)(alkyl)aminocarbonyl radical $((R)_2N$—CO—$)$ in which the R radicals independently represent a hydrogen or a $C_1$-$C_4$ alkyl radical;
the $R_5$ radicals, which may be identical or different, represent:
  an optionally substituted $C_1$-$C_{20}$ alkyl radical, optionally interrupted by one or more heteroatoms and/or by one or more groups comprising at least one heteroatom, preferably chosen from oxygen, sulphur, CO, SO and $SO_2$, or combinations thereof; the alkyl radical not comprising any nitro, nitroso, peroxo or diazo functional groups;
  a trimethylsilyl($C_1$-$C_4$)alkyl radical;
  an optionally substituted phenyl radical;
  an optionally substituted benzyl radical;
the $R_2$ and $R_3$ radicals, which may be identical or different, represent, independently of one another:
  a halogen atom;
  an optionally substituted $C_1$-$C_{16}$ alkyl radical, optionally interrupted by one or more heteroatoms and/or by one or more groups comprising at least one heteroatom preferably chosen from oxygen, nitrogen, sulphur, CO, SO and $SO_2$, or combinations thereof; the alkyl radical not comprising any nitro, nitroso, peroxo or diazo functional groups;
a hydroxyl radical;
a $C_1$-$C_4$ alkoxy radical; a $C_2$-$C_4$ (poly)hydroxyalkoxy group;
an alkoxycarbonyl radical (RO—CO—) in which R represents a $C_1$-$C_4$ alkyl radical;
an alkylcarbonyloxy radical (RCO—O) in which R represents a $C_1$-$C_4$ alkyl radical;
an optionally substituted aryloxy radical;
an optionally substituted (di)arylamino radical;
an amino radical optionally substituted by one or two $C_1$-$C_4$ alkyl radicals, which may be identical or different, optionally bearing at least one hydroxyl or $C_1$-$C_2$ alkoxy group, it being possible for said alkyl radicals to optionally form, with the nitrogen atom to which they are attached, a saturated or unsaturated, optionally substituted, optionally aromatic heterocycle having 5 or 7 ring members, optionally comprising another heteroatom which may be identical to or different from nitrogen;
an alkylcarbonylamino radical (RCO—NR'—) in which the R radical represents a $C_1$-$C_4$ alkyl radical and R' represents a hydrogen or a $C_1$-$C_4$ alkyl radical;
a (di)(alkyl)aminocarbonyl group ((R)$_2$N—CO—) in which the R radicals, independently of one another, represent a hydrogen or a $C_1$-$C_4$ alkyl radical;
a ureido radical (N(R)$_2$—CO—NR'—) in which the R radicals, independently of one another, represent a $C_1$-$C_4$ alkyl radical, and R' represents a hydrogen or a $C_1$-$C_4$ alkyl radical;
a (di)(alkyl)aminosulphonyl radical ((R)$_2$N—$SO_2$—) in which the R radical represents a hydrogen or a $C_1$-$C_4$ alkyl radical;
an alkylthio radical (R—S—) in which the R radical represents a $C_1$-$C_4$ alkyl radical;
an alkylsulphonylamino radical ($RSO_2$—NR'—) in which the R radical represents a $C_1$-$C_4$ alkyl radical, and the R' radical represents a hydrogen atom or a $C_1$-$C_4$ alkyl radical;
a cyano radical (—C≡N);
a phenyl radical;
a trifluoromethyl radical (—$CF_3$);
a thio (—SH) radical;
an alkylsulphinyl radical (RSO—) in which the R radical represents a $C_1$-$C_4$ alkyl radical;
an alkylsulphonyl radical ($RSO_2$—) in which the R radical represents a $C_1$-$C_4$ alkyl radical;
$R_1$ can form with an $R_2$ radical located in the ortho position with respect to the $NR_1$ group and with the nitrogen atom substituted by $R_1$, a substituted or unsubstituted, saturated or unsaturated heterocycle comprising 5 or 6 ring members;
two adjacent $R_2$ radicals can form, with one another and with the carbon atoms to which they are attached, a substituted or unsubstituted, aromatic or non-aromatic (hetero)cyclic radical comprising 5 or 6 ring members;
two adjacent $R_3$ radicals can form, with one another and with the carbon atoms to which they are attached, a substituted or unsubstituted aromatic ring comprising 5 or 6 ring members;
the $R_4$ radical represents:
a hydrogen atom;
an optionally substituted $C_1$-$C_{16}$ alkyl radical, optionally interrupted by one or more heteroatoms and/or by one or more groups comprising at least one heteroatom, preferably chosen from oxygen, nitrogen, sulphur, CO, SO and $SO_2$, or combinations thereof; the alkyl radical not comprising any nitro, nitroso, peroxo or diazo functional groups;
an amino radical optionally substituted by one or two $C_1$-$C_4$ alkyl radicals, which may be identical or different, optionally bearing at least one hydroxyl or $C_1$-$C_2$ alkoxy group, it being possible for said alkyl radicals to optionally form, with the nitrogen atom to which they are attached, a saturated or unsaturated or aromatic, optionally substituted heterocycle having 5 or 6 ring members, optionally comprising at least one other heteroatom which may be identical to or different from nitrogen;
an alkylcarbonylamino radical (RCO—NR'—) in which the R radical represents a $C_1$-$C_4$ alkyl radical and R' represents a hydrogen or a $C_1$-$C_4$ alkyl radical;
a ureido radical (N(R)$_2$—CO—NR'—) in which the R radicals, independently of one another, represent a $C_1$-$C_4$ alkyl radical, and R' represents a hydrogen or a $C_1$-$C_4$ alkyl radical;
an alkylsulphonylamino radical ($RSO_2$—NR'—) in which the R radical represents a $C_1$-$C_4$ alkyl radical, and R' represents a hydrogen or a $C_1$-$C_4$ alkyl radical;
a hydroxycarbonyl radical;
a $C_1$-$C_4$ alkoxycarbonyl radical;
a cyano radical;
an optionally substituted phenyl radical;
an optionally substituted benzyl radical;
the $R_6$ and $R_7$ radicals, which may be identical or different, represent:
a hydrogen atom;
an optionally substituted $C_1$-$C_{16}$ alkyl radical, optionally interrupted by one or more heteroatoms and/or by one or more groups comprising at least one heteroatom, preferably chosen from oxygen, nitrogen, sulphur, CO, SO and $SO_2$, or combinations thereof; the alkyl radical not comprising any nitro, nitroso, peroxo or diazo functional groups;
an (alkoxy)aryl radical (-Ph-OR) in which the R radical represents a hydrogen or a $C_1$-$C_4$ alkyl radical;
a (di)(alkyl)aminoaryl radical (-Ph-N(R)$_2$) in which the R radicals, independently of one another, represent a hydrogen or a $C_1$-$C_4$ alkyl radical optionally substituted by a hydroxyl;
an alkylsulphonyl radical ($RSO_2$—) in which the R radical represents a $C_1$-$C_4$ alkyl radical;
an aminocarbonyl radical, a (di)($C_1$-$C_4$)alkylaminocarbonyl radical;
optionally a $CH_3CO$— radical;
a phenyl;
a benzyl optionally substituted by one or more hydroxyl and/or amino groups;
the $R_6$ and $R_7$ radicals can optionally form with the nitrogen atom to which they are attached, a saturated or unsaturated, optionally substituted heterocycle comprising from 5 to 7 ring members, optionally comprising another heteroatom which may be identical to or different from nitrogen;
one of the $R_6$ or $R_7$ radicals can also form with the nitrogen atom to which it is attached and with an $R_2$ radical located in the ortho position with respect to the $NR_6R_7$ group, a substituted or unsubstituted, saturated or unsaturated heterocycle comprising 5 or 6 ring members;
the $R_6$ and $R_7$ radicals can form with the nitrogen atom to which they are attached and each with an $R_2$ radical located in the ortho position with respect to the $NR_6R_7$ group, a substituted or unsubstituted, saturated or unsaturated heterocycle comprising 5 or 6 ring members;

n is an integer between 0 and 4, when n is below 4, the unsubstituted carbon atom or atoms bear(s) a hydrogen atom;

n' is an integer between 0 and 4, when n' is below 4, the unsubstituted carbon atom or atoms bear(s) a hydrogen atom;

the electroneutrality of the compounds of formulae (I) and/or (II) being ensured by one or more cosmetically acceptable anions An, which may be identical or different.

Another subject of the present invention is dyeing compositions comprising such compounds, as direct dyes, in a medium suitable for dyeing keratin fibres.

It also relates to a method for dyeing keratin fibres that consists in bringing a composition according to the invention into contact with said dry or wet fibres for a sufficient time to obtain the desired effect.

Another subject of the invention is a multicompartment device comprising, in a first compartment, the composition according to the invention and, in a second compartment, an oxidizing composition.

A last subject of the invention is finally constituted of several methods for preparing compounds according to the invention.

It has been observed that the compounds having a hydrazone functional group as defined previously made it possible to broaden the colour range and had a good fastness to external agents such as shampoos in particular, even when the keratin fibre is sensitized. They are also stable under alkaline lightening conditions.

Moreover, these compounds can constitute synthesis intermediates for dyes comprising several chromophores linked to one another by one or more linker arm(s).

However, other features and advantages of the present invention will emerge more clearly on reading the description and the examples which will be presented.

In the subsequent text, and unless otherwise indicated, the limits delimiting a range of values are included in this range.

In the meaning of the present invention, and unless otherwise indicated:
an alkyl radical is linear or branched;
an alkyl radical or the alkyl part of a radical is said to be "substituted" when it comprises at least one substituent chosen from the groups:
hydroxyl;
$C_1$-$C_4$ alkoxy, (poly)hydroxy($C_2$-$C_4$)alkoxy;
amino optionally substituted by one or more $C_1$-$C_4$ alkyl groups, which may be identical or different, optionally bearing at least one hydroxyl group, it being possible for said alkyl radicals to form, with the nitrogen atom to which they are attached, a heterocycle comprising 5 or 6 ring members, and optionally comprising at least one other heteroatom which may or may not be different from nitrogen.

Preferably, the alkyl radicals do not bear an alkyl-$SO_2$—O— group or aryl-$SO_2$—O— group with an aryl group substituted by an alkyl radical.

An aryl or heteroaryl radical or the aryl or heteroaryl Part of a radical is said to be "substituted" when it comprises at least one substituent borne by a carbon atom, chosen from
a $C_1$-$C_{16}$, preferably $C_1$-$C_8$, alkyl radical optionally substituted by one or more radicals chosen from the radicals: hydroxyl, $C_1$-$C_2$ alkoxy, (poly)hydroxy($C_2$-$C_4$) alkoxy, acylamino, amino substituted by two $C_1$-$C_4$ alkyl radicals, which may be identical or different, optionally bearing at least one hydroxyl group, or it being possible for the two radicals to form, with the nitrogen atom to which they are attached, a heterocycle comprising 5 or 7 ring members, preferably 5 or 6 ring members, and optionally comprising another heteroatom which may be identical to or different from nitrogen;

a halogen atom such as chlorine, fluorine or bromine;

a hydroxyl group;

a $C_1$-$C_2$ alkoxy radical; a (poly)hydroxy($C_2$-$C_4$)alkoxy radical;

an amino radical optionally substituted by one or two $C_1$-$C_4$ alkyl radicals, which may be identical or different, optionally bearing at least one hydroxyl or amino group substituted by two optionally substituted $C_1$-$C_2$ alkyl radicals;

an alkylcarbonylamino radical (—NR—COR') in which the R radical is a hydrogen atom or a $C_1$-$C_4$ alkyl radical optionally bearing at least one hydroxyl group, and the R' radical is a $C_1$-$C_2$ alkyl radical;

a (di)(alkyl)aminocarbonyl radical ((R)$_2$N—CO) in which the R radicals, which may be identical or different, represent a hydrogen atom or a $C_1$-$C_4$ alkyl radical optionally bearing at least one hydroxyl group;

an alkylsulphonylamino radical (R'SO$_2$—NR—) in which the R radical represents a hydrogen atom or a $C_1$-$C_4$ alkyl radical optionally bearing at least one hydroxyl group, and the R' radical represents a $C_1$-$C_4$ alkyl radical or a phenyl radical;

an aminosulphonyl radical ((R)$_2$N—SO$_2$—) in which the R radicals, which may be identical or different, represent a hydrogen atom or a $C_1$-$C_4$ alkyl radical optionally bearing at least one hydroxyl group.

The cyclic or heterocyclic part of a non-aromatic radical or a (hetero)cyclic radical is said to be substituted when it comprises at least one substituent borne by a carbon atom, chosen from the groups:
hydroxyl;
$C_1$-$C_4$ alkoxy, (poly)hydroxy($C_2$-$C_4$)alkoxy;
alkylcarbonylamino (RCO—NR'—) in which the R' radical is a hydrogen atom or a $C_1$-$C_4$ alkyl radical optionally bearing at least one hydroxyl group, and the R radical is a $C_1$-$C_2$ alkyl radical or an amino radical substituted by two $C_1$-$C_4$ alkyl groups, which may be identical or different, optionally bearing at least one hydroxyl group, it being possible for said alkyl radicals to form, with the nitrogen atom to which they are attached, a heterocycle comprising 5 or 6 ring members, and optionally comprising at least one other heteroatom which may or may not be different from nitrogen.

As indicated previously, a first subject of the invention consists of compounds corresponding to aforementioned formulae (I) and/or (II).

According to one particular embodiment of the invention, the $R_1$ radical represents:
a hydrogen;
a $C_1$-$C_6$ alkyl radical optionally substituted by at least one hydroxyl group, by at least one $C_1$-$C_2$ alkoxy group, by at least one hydroxycarbonyl group, optionally by at least one amino group which may or may not be substituted by one or two $C_1$-$C_2$ alkyl radicals, which may be identical or different;

a phenyl radical optionally substituted by at least one halogen atom such as chlorine, bromine, iodine or fluorine or by at least one hydroxyl group;

a benzyl radical optionally substituted by one or more hydroxyl and/or amino groups;

a ($C_1$-$C_4$)alkylcarbonyl radical; and a ($C_1$-$C_4$)alkylsulphonyl radical.

Preferably, the $R_1$ radical represents a hydrogen atom; a methyl radical, a 2-hydroxyethyl radical, a 3-methoxypropyl radical, a (di)(methyl)aminoethyl radical, a $CH_3CO$— radical, a $CH_3SO_2$— radical, a phenyl radical, a 4-chlorophenyl radical, a benzyl radical optionally substituted by one or two hydroxyl or amino group(s), or a combination thereof.

In accordance with one even more particular variant of the invention, $R_1$ represents a hydrogen atom; a methyl radical; a 2-hydroxyethyl radical; a $CH_3CO$— radical; a $CH_3SO_2$-radical; or an unsubstituted benzyl radical.

In accordance with one more precise variant of the invention, the $R_5$ radicals, which may be identical or different, represent:

an optionally substituted $C_1$-$C_{16}$, preferably $C_1$-$C_8$, alkyl radical, optionally interrupted by one or more heteroatoms and/or by one or more groups comprising at least one heteroatom, preferably chosen from oxygen, nitrogen, sulphur, CO, SO and $SO_2$, or combinations thereof; the alkyl radical not comprising any nitro, nitroso, peroxo or diazo functional groups;

a trimethylsilyl($C_1$-$C_4$)alkyl radical;

an optionally substituted phenyl radical; and an optionally substituted benzyl radical.

Preferably, the $R_5$ radicals, which may be identical or different, represent the methyl, ethyl, propyl, butyl, pentyl, hexyl, heptyl, octyl, 2-hydroxyethyl, 3-hydroxypropyl, 6-hydroxyhexyl, 2-methoxyethyl, 3-methoxypropyl, 3-trimethylsilylpropyl, 2-((di)methyl)aminopropyl, 3-((di)methyl)aminopropyl, phenyl, 4-chlorophenyl, benzyl or 3,4-dihydroxybenzyl radicals.

According to one even more particular variant of the invention, the $R_5$ radicals, which may be identical or different, represent the methyl, ethyl, propyl, butyl, 3-trimethylsilylpropyl, 4-chlorophenyl or benzyl radicals.

More particularly, the $R_2$, $R_3$ radicals, which may be identical or different, represent:

a halogen atom chosen from bromine, chlorine, fluorine or iodine;

an optionally substituted $C_1$-$C_{16}$ alkyl radical, optionally interrupted by one or more heteroatoms and/or by one or more groups comprising at least one heteroatom, preferably chosen from oxygen, nitrogen, sulphur, CO, SO and $SO_2$, or combinations thereof; the alkyl radical not comprising any nitro, nitroso, peroxo or diazo functional groups;

a hydroxyl radical;

a $C_1$-$C_4$ alkoxy radical; a $C_2$-$C_4$ (poly)hydroxyalkoxy group;

a ($C_1$-$C_4$)alkoxycarbonyl radical;

a ($C_1$-$C_4$)alkylcarbonyloxy radical;

an optionally substituted aryloxy radical;

an amino radical optionally substituted by one or two $C_1$-$C_4$ alkyl radicals, which may be identical or different, optionally bearing at least one hydroxyl or $C_1$-$C_2$ alkoxy group, it being possible for said alkyl radicals to optionally form, with the nitrogen atom to which they are attached, a saturated or unsaturated, optionally substituted, optionally aromatic heterocycle having 5 or 7 ring members, optionally comprising another heteroatom which may be identical to or different from nitrogen; or by one or two phenyl, aminophenyl, N,N-diethylaminophenyl or methoxyphenyl radicals;

a ($C_1$-$C_4$)alkylcarbonylamino radical in which the amino functional group may or may not be substituted by a $C_1$-$C_4$ alkyl radical;

an aminocarbonyl radical, a (di)($C_1$-$C_4$)alkylaminocarbonyl group;

a ureido radical which may or may not be substituted by one or more $C_1$-$C_4$ alkyl radicals;

an aminosulphonyl, (di)($C_1$-$C_4$)alkylaminosulphonyl radical;

a ($C_1$-$C_4$)alkylthio radical;

a ($C_1$-$C_4$)alkylsulphonylamino radical in which the amino functional group may or may not be substituted by a $C_1$-$C_4$ alkyl radical;

a cyano radical;

a phenyl radical;

a trifluoromethyl radical;

a thio radical;

a ($C_1$-$C_4$)alkylsulphinyl radical; and a ($C_1$-$C_4$)alkylsulphonyl radical.

Preferably, the $R_2$, $R_3$ radicals, which may be identical or different, represent:

a halogen atom chosen from chlorine or fluorine;

a $C_1$-$C_8$ alkyl radical optionally substituted by one or more hydroxyl or ((di)alkyl)amino or sulphonylamino groups, optionally interrupted by one or more heteroatoms and/or by one or more groups comprising at least one heteroatom, preferably chosen from oxygen, sulphur, SO and $SO_2$, or combinations thereof;

a hydroxyl radical;

a $C_1$-$C_4$ alkoxy radical;

a ($C_1$-$C_4$)alkoxycarbonyl radical;

an optionally substituted aryloxy radical;

an optionally substituted amino radical:

by one or two $C_1$-$C_4$ alkyl radicals, which may be identical or different, optionally bearing at least one hydroxyl or $C_1$-$C_2$ alkoxy group; or by one or two phenyl, aminophenyl or methoxyphenyl radicals;

a ($C_1$-$C_4$)alkylcarbonylamino radical in which the amino functional group may or may not be substituted by a $C_1$-$C_4$ alkyl radical;

an aminocarbonyl radical;

an aminosulphonyl, (di)($C_1$-$C_4$)alkylaminosulphonyl radical;

a ($C_1$-$C_4$)alkylthio radical;

a phenyl radical;

a trifluoromethyl radical;

a thio radical.

More particularly, the $R_2$, $R_3$ radicals, which may be identical or different, represent:

a chlorine atom;

a $C_1$-$C_3$ alkyl radical optionally substituted by a hydroxy group;

a hydroxyl radical;

a $C_1$-$C_4$ alkoxy radical;

a ($C_2$-$C_3$)alkoxycarbonyl radical;

a phenyloxy radical;

an optionally substituted amino radical:

by one or two $C_1$-$C_4$, preferably $C_1$-$C_2$, alkyl radicals, which may be identical or different, optionally bearing at least one hydroxyl or $C_1$-$C_2$ alkoxy group; or by one or two phenyl, aminophenyl or methoxyphenyl radicals;

a (C$_1$-C$_2$)alkylcarbonylamino radical in which the amino functional group may or may not be substituted by a C$_1$-C$_4$ alkyl radical.

Preferably, the R$_2$, R$_3$ radicals, which may be identical or different, represent:
a chlorine or fluorine atom;
a methyl, ethyl, propyl, butyl, pentyl or hexyl;
a 2-hydroxyethyl, 3-hydroxypropyl or 6-hydroxyhexyl;
a hydroxyl;
a methoxy, ethoxy, propoxy or butoxy;
a hydroxycarbonyl;
a methoxycarbonyl or ethoxycarbonyl;
a phenyloxy;
a phenylamino;
an amino;
a (di)methylamino or (di)ethylamino;
an aminophenylamino or methoxyphenylamino;
a 4-N,N-diethylaminophenylamino radical;
a methylcarbonylamino;
an aminocarbonyl;
an aminosulphonyl or dimethylaminosulphonyl;
a methylthio radical;
a phenyl radical;
a trifluoromethyl radical;
a thio radical.

According to another particular embodiment of the invention, the compounds of formula (I) and/or (II) are such that two adjacent R$_2$ radicals form, with one another and with the carbon atoms to which they are attached, a substituted or unsubstituted, optionally aromatic cyclic radical comprising 5 or 6 ring members.

According to this particular embodiment, two adjacent R$_2$ radicals form, with one another and with the carbon atoms to which they are attached, an unsubstituted, aromatic cyclic radical comprising 6 ring members.

According to another embodiment, two adjacent R$_3$ radicals can form, with one another and with the carbon atoms to which they are attached, a substituted or unsubstituted aromatic ring comprising 6 ring members. Preferably, when said aromatic ring is substituted, it is substituted by one or more radicals chosen from hydroxyl, amino, diethylamino, hydroxycarbonyl, methoxycarbonyl, chlorine, methyl, ethyl and methoxy.

According to this particular embodiment, two adjacent R$_3$ radicals form, with one another and with the carbon atoms to which they are attached, an unsubstituted, aromatic cyclic radical having 6 ring members.

Advantageously, the R$_4$ radical more particularly represents:
a hydrogen atom;
an optionally substituted C$_1$-C$_8$, preferably unsubstituted C$_1$-C$_4$, alkyl radical;
a hydroxycarbonyl radical;
a C$_1$-C$_2$ alkoxycarbonyl radical;
a phenyl radical;
a benzyl radical optionally substituted by one or two hydroxyl or amino groups, or a combination thereof.

Preferably, the R$_4$ radical represents a hydrogen atom, a methyl radical, a methoxycarbonyl radical, optionally a hydroxycarbonyl radical, a phenyl radical, a benzyl radical optionally substituted by one or two hydroxyl or amino groups, or a combination thereof, and even more particularly a hydrogen atom, a methyl radical, a methoxycarbonyl radical, a hydroxycarbonyl radical or an unsubstituted benzyl radical.

As regards the R$_6$ and R$_7$ radicals, the latter, which may be identical or different, more particularly represent:

a hydrogen atom;
an optionally substituted C$_1$-C$_8$ alkyl radical, optionally interrupted by one or more heteroatoms and/or by one or more groups comprising at least one heteroatom, preferably chosen from oxygen, nitrogen, sulphur, CO, SO and SO$_2$, or combinations thereof; the alkyl radical not comprising any nitro, nitroso, peroxo or diazo functional groups;
a phenyl optionally substituted by one or more C$_1$-C$_4$ alkoxy radicals and/or by one or more (di)(C$_1$-C$_4$)(alkyl) amino radicals;
a benzyl optionally substituted by one or more hydroxyl and/or amino groups;
an aminocarbonyl radical, a (di)(C$_1$-C$_4$)alkylaminocarbonyl radical; and
optionally a CH$_3$CO— radical.

Preferably, the R$_6$ and R$_7$ radicals, which may be identical or different, represent:
a hydrogen atom;
a methyl, ethyl, 2-hydroxyethyl, 3-hydroxypropyl or 3-methoxypropyl;
a phenyl;
a benzyl optionally substituted by one or two hydroxyl and/or amino groups;
a methoxyphenyl;
an aminophenyl;
a (4-N,N—)diethylaminophenyl;
optionally a CH$_3$CO— radical.

As regards n, this is an integer between 0 and 4, when n is below 4, the unsubstituted carbon atom or atoms bear(s) a hydrogen atom. Preferably, n is between 0 and 2.

As regards n', this coefficient is an integer between 0 and 4, when n' is below 4, the unsubstituted carbon atom or atoms bear(s) a hydrogen atom. Preferably, n' is between 0 and 2.

In accordance with one advantageous variant of the invention, the compounds of formula (I) and/or (II) are such that the R$_6$ and R$_7$ radicals, especially in the case of alkyl radicals as defined previously, form, with the nitrogen atom to which they are attached, a preferably saturated heterocycle comprising 5, 6 or 7 ring members, optionally comprising another heteroatom which may be identical to or different from nitrogen, such as oxygen preferably.

By way of example of such a group, mention may be made of pyrrolidine, piperidine, piperazine, morpholine, homopiperazine and homopiperidine rings.

According to a second advantageous variant of the invention, the compounds of formula (I) and/or (II) are such that one of the R$_6$ or R$_7$ radicals can also form, with the nitrogen atom to which it is attached and with an R$_2$ radical located in the ortho position with respect to the NR$_6$R$_7$ group, a saturated or unsaturated heterocycle comprising 5 or 6 ring members, which may or may not be substituted, more particularly by a hydroxyl or methoxy group.

For example, the —NR$_6$R$_7$ group, with the aromatic ring optionally substituted by a hydroxyl may correspond to the following compounds:

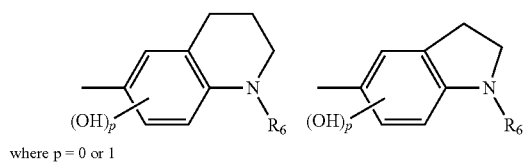

where p = 0 or 1

According to a third advantageous variant of the invention, the compounds of formula (I) and/or (II) are such that the two $R_6$ and $R_7$ radicals can form with the nitrogen atom to which they are attached and each with an $R_2$ radical located in the ortho position with respect to the $NR_6R_7$ group, a saturated or unsaturated heterocycle comprising 5 or 6 ring members, which may or may not be substituted, more particularly by a hydroxyl or methoxy group.

For example, the —$NR_6R_7$ group, with the aromatic ring optionally substituted by a hydroxyl may correspond to the following compounds:

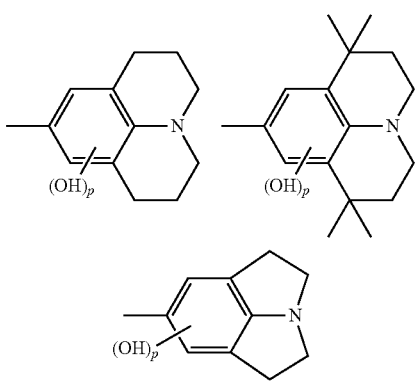

where p = 0 or 1

In the formulae of the compounds of formula (I) and/or (II), An represents an anion or a mixture of organic or mineral anions that makes it possible to balance the charge or charges of the compounds of formula (I) and/or (II), for example chosen from a halide such as chloride, bromide, fluoride or iodide; a hydroxide; a sulphate; a hydrogensulphate; an alkylsulphate for which the linear or branched alkyl part is a $C_1$-$C_6$ alkyl part, such as the methylsulphate or ethylsulphate ion; carbonates and hydrogencarbonates; carboxylic acid salts, such as formate, acetate, citrate, tartrate or oxalate; alkylsulphonates for which the linear or branched alkyl part is a $C_1$-$C_6$ alkyl part such as the methylsulphonate ion; arylsulphonates for which the aryl, preferably phenyl, part, is optionally substituted by one or more $C_1$-$C_4$ alkyl radicals such as, for example, 4-toluoylsulphonate; and alkylsulphonyls such as mesylate.

The addition salts of the compounds of formula (I) and/or (II) with an acid may be, for example, the addition salts with an organic or mineral acid such as hydrochloric acid, hydrobromic acid, sulphuric acid or (alkyl- or phenyl-)sulphonic acids such as p-toluenesulphonic acid or methylsulphonic acid.

The solvates of the compounds of formula (I) and/or (II) represent the hydrates of such compounds and/or the association of a compound of formula (I) and/or (II), with a linear or branched $C_1$-$C_4$ alcohol such as methanol, ethanol, isopropanol or n-propanol.

According to one particular embodiment, the compounds of formula (I) and/or (II) are represented by the following formulae, and also resonant forms thereof and/or addition salts thereof with an acid and/or solvates thereof:

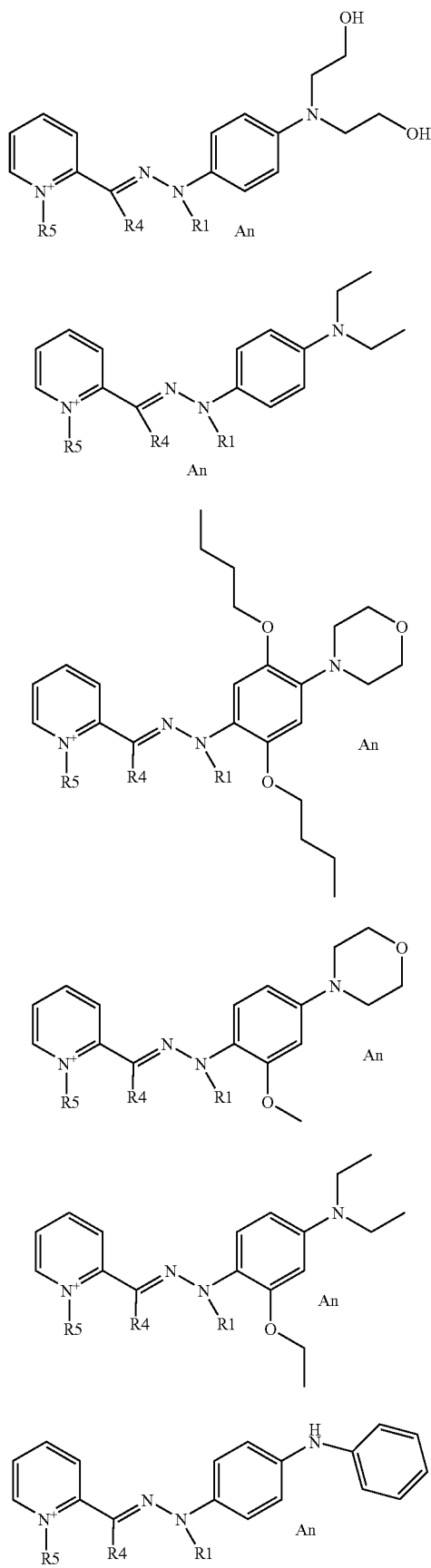

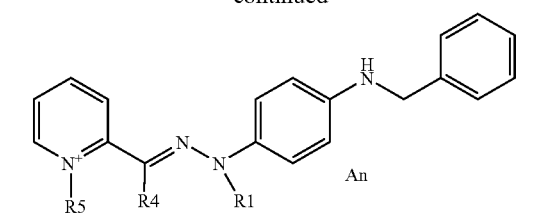
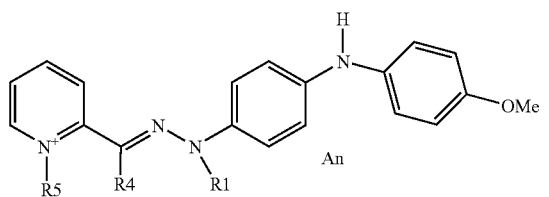
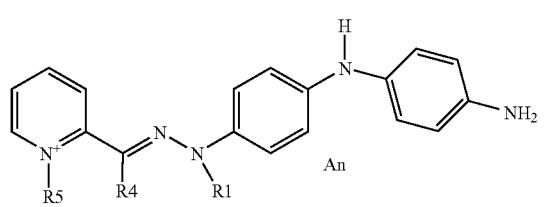
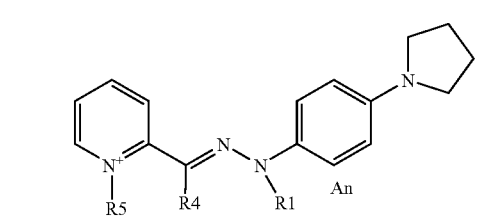
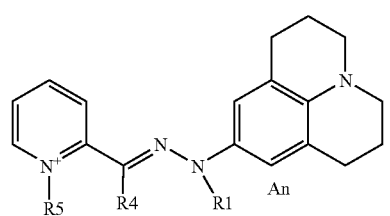
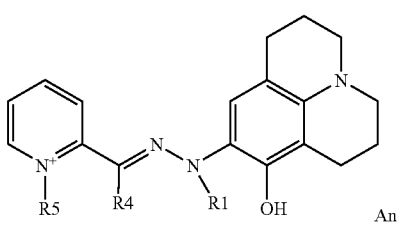
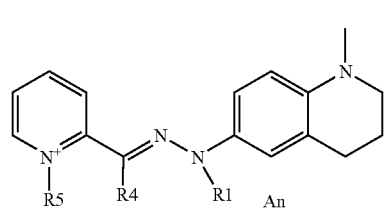
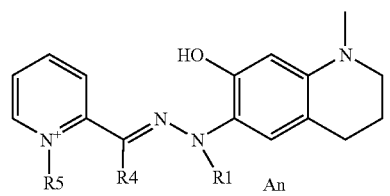
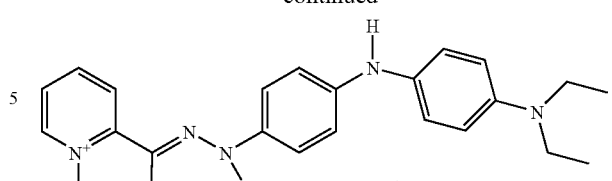
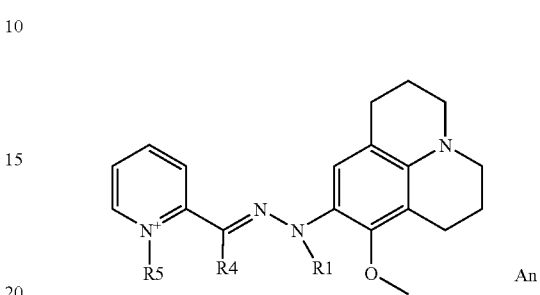
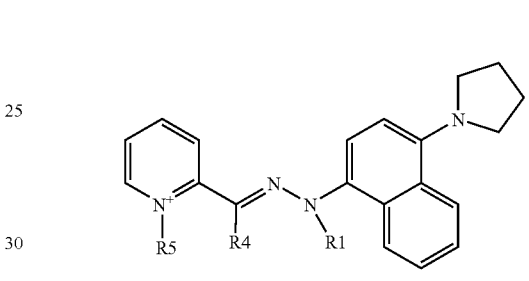
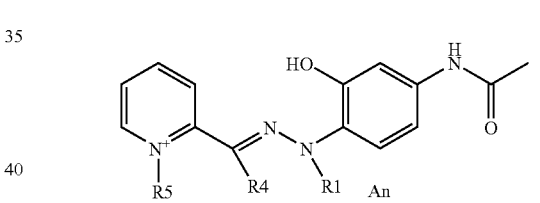
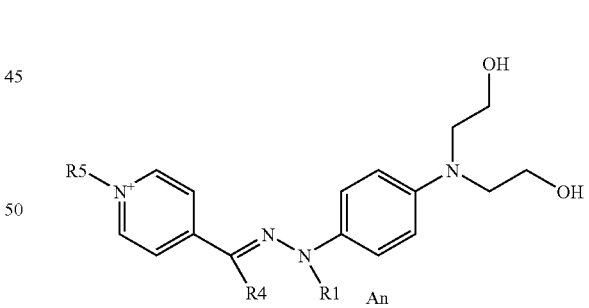
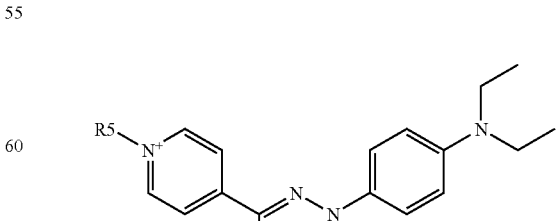
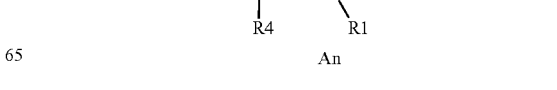

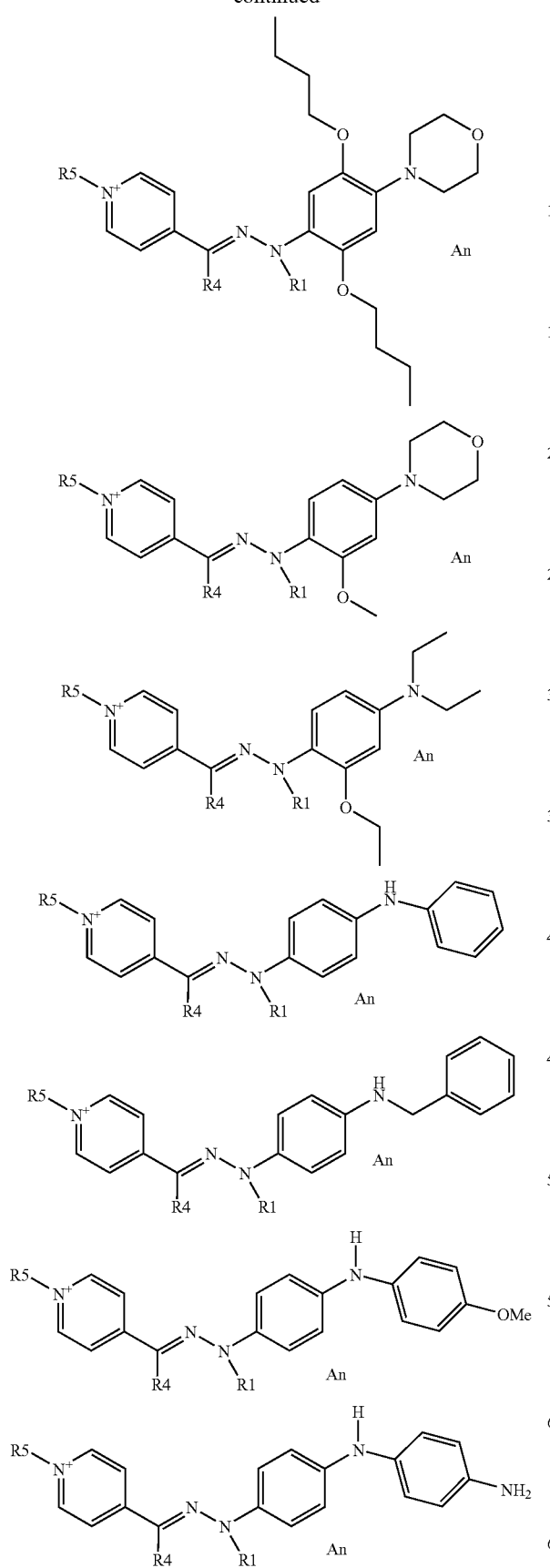
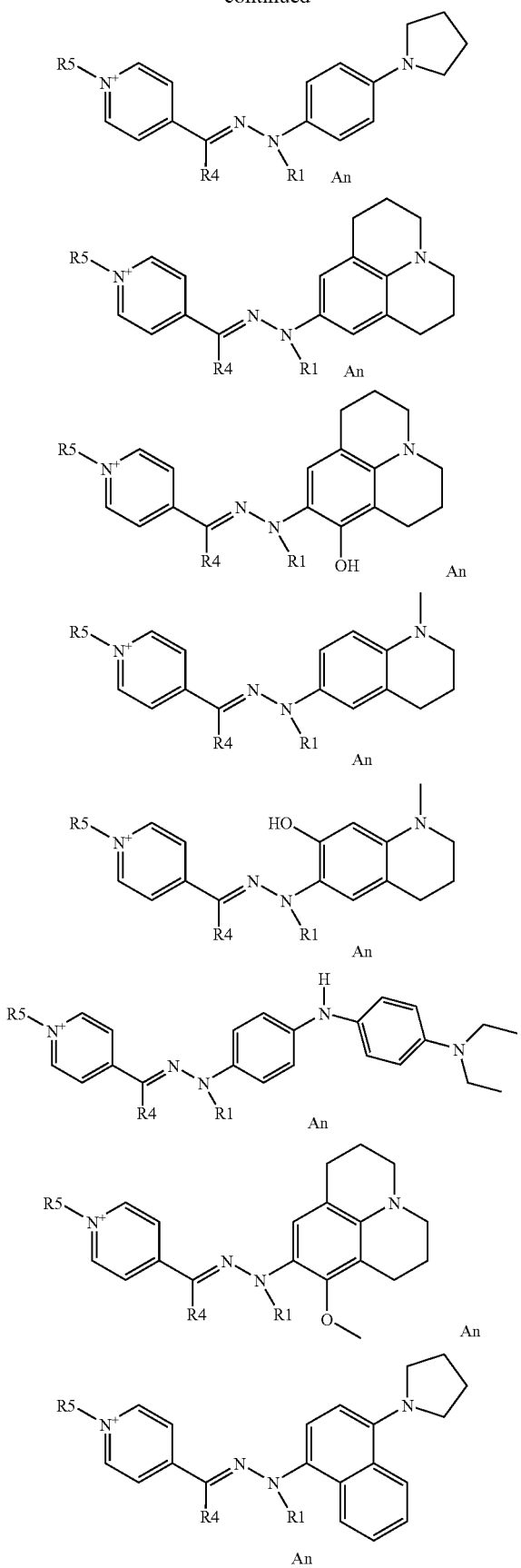

17
-continued
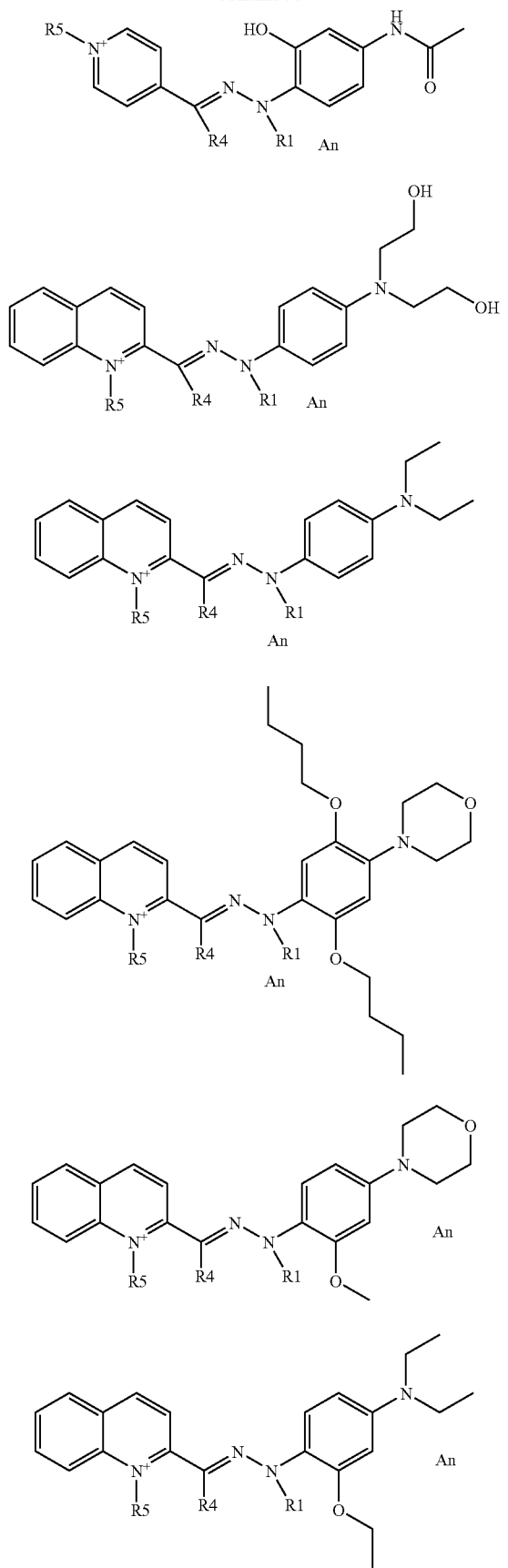
18
-continued
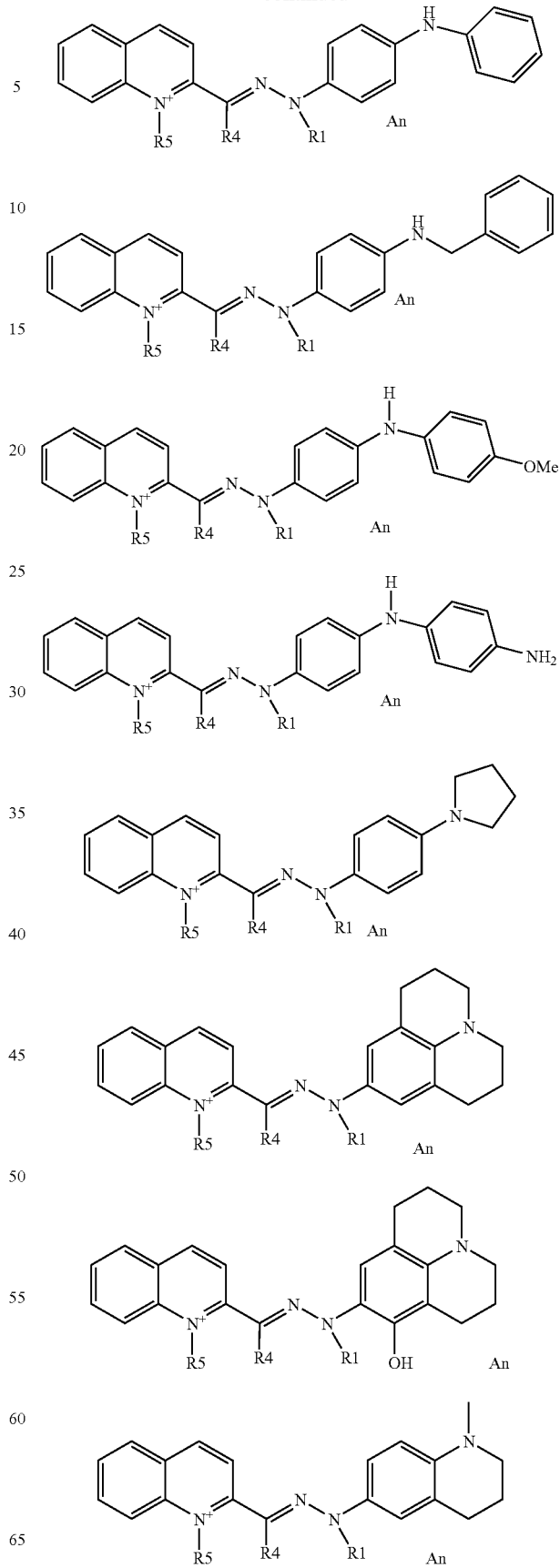

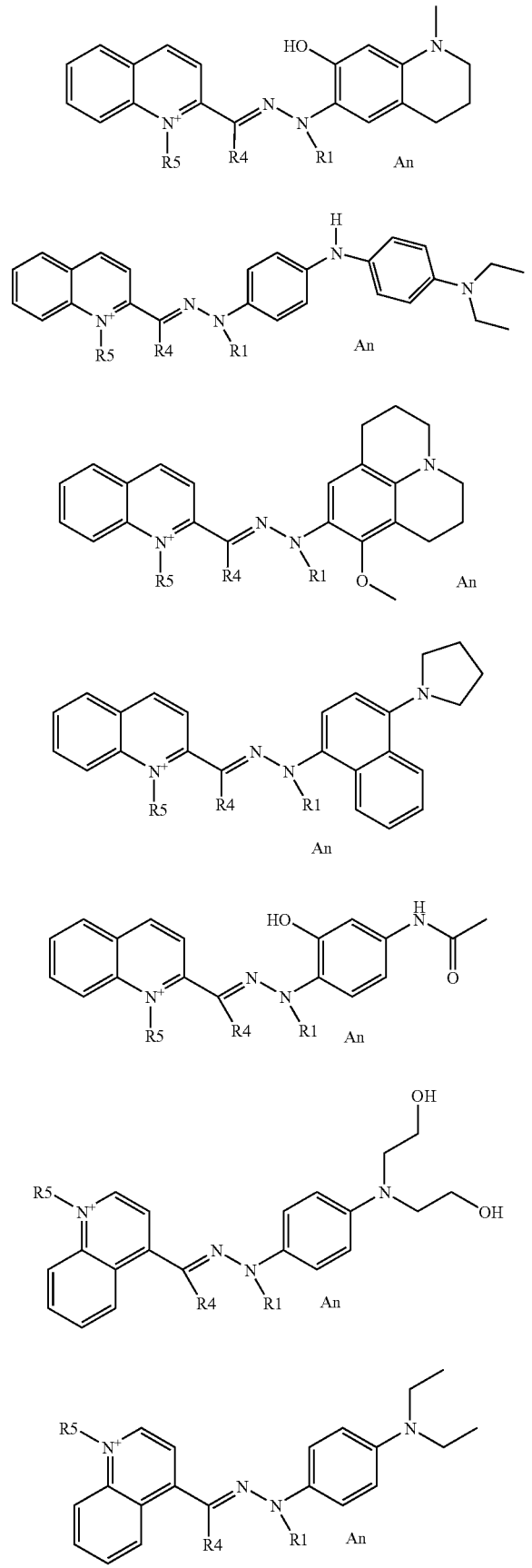
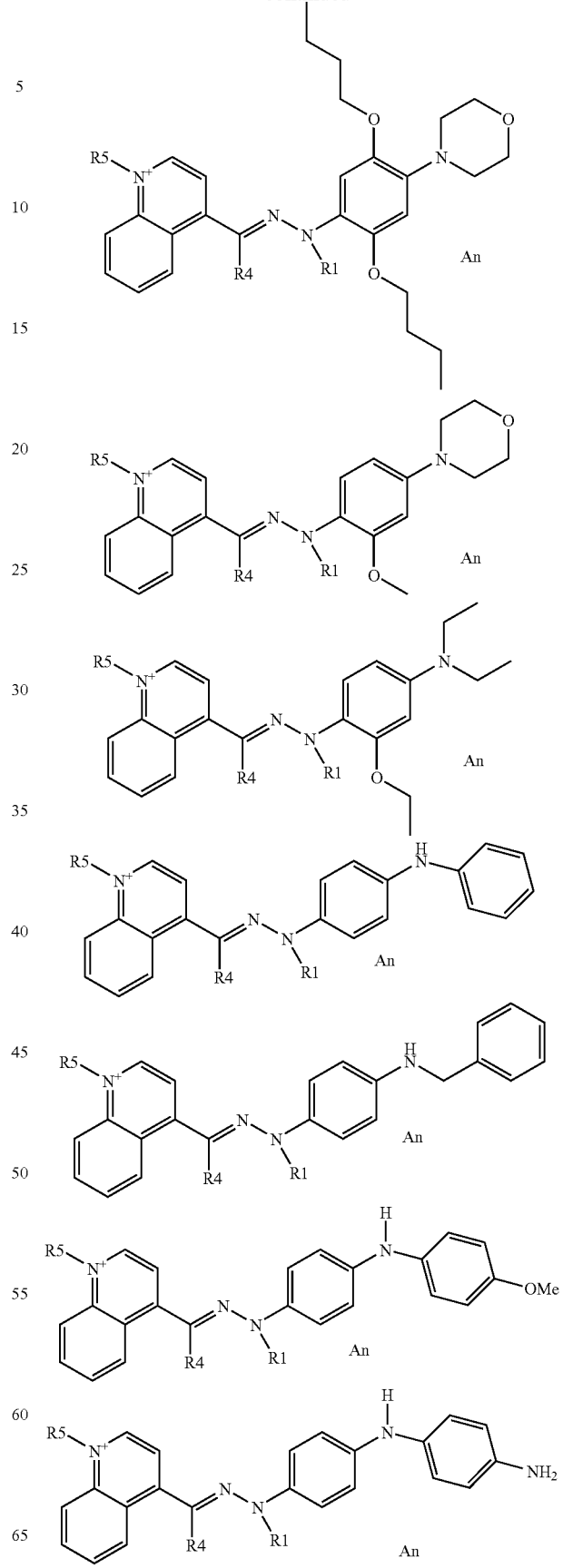

-continued
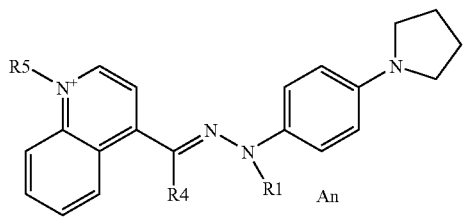
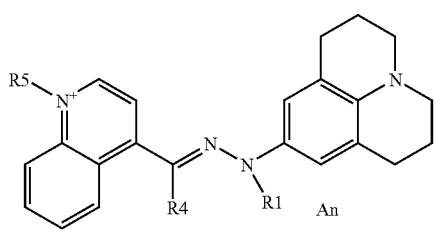
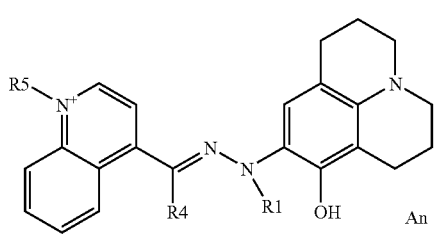
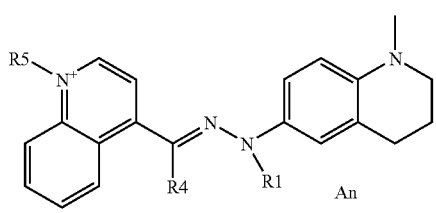
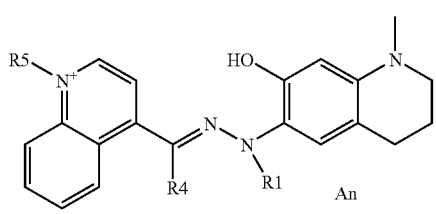
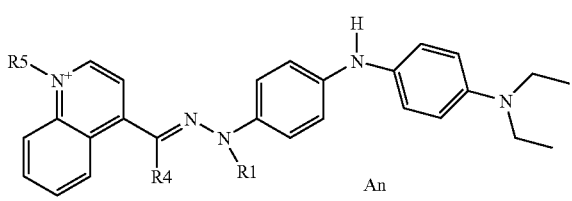
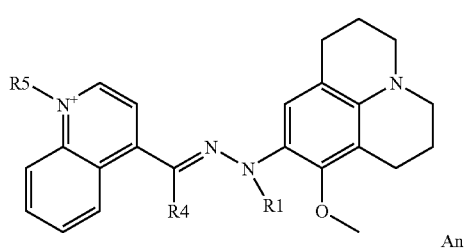
-continued
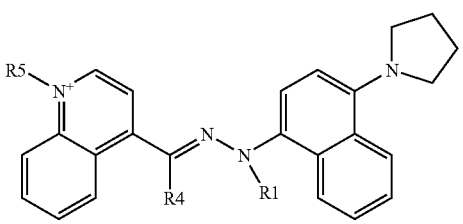
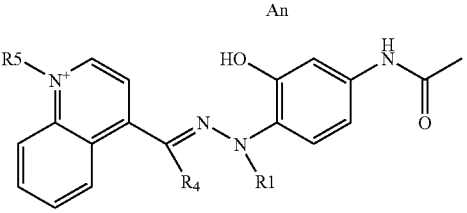
in which the $R_1$, $R_4$, $R_5$ radicals and An are as defined previously.
In particular, the specific monocationic monochromophoric dyes of hydrazone type of specific formula comprising a 2- or 4-pyridinium or 2- or 4-quinolinium unit of formula (I) and/or (II) according to the present invention, are represented by the following compounds:
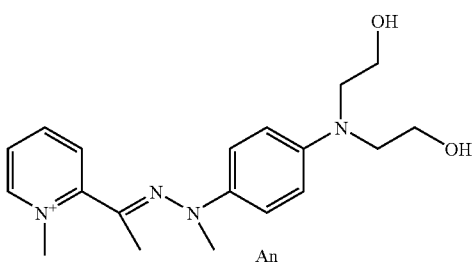
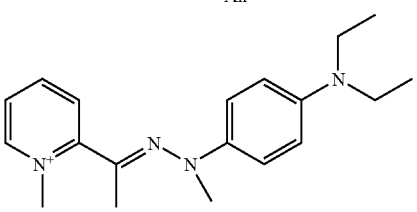
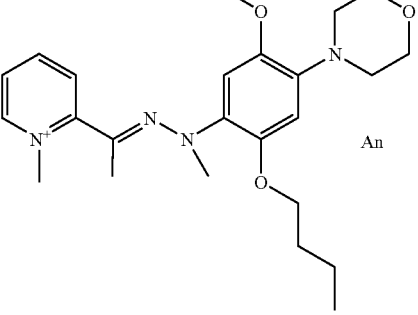

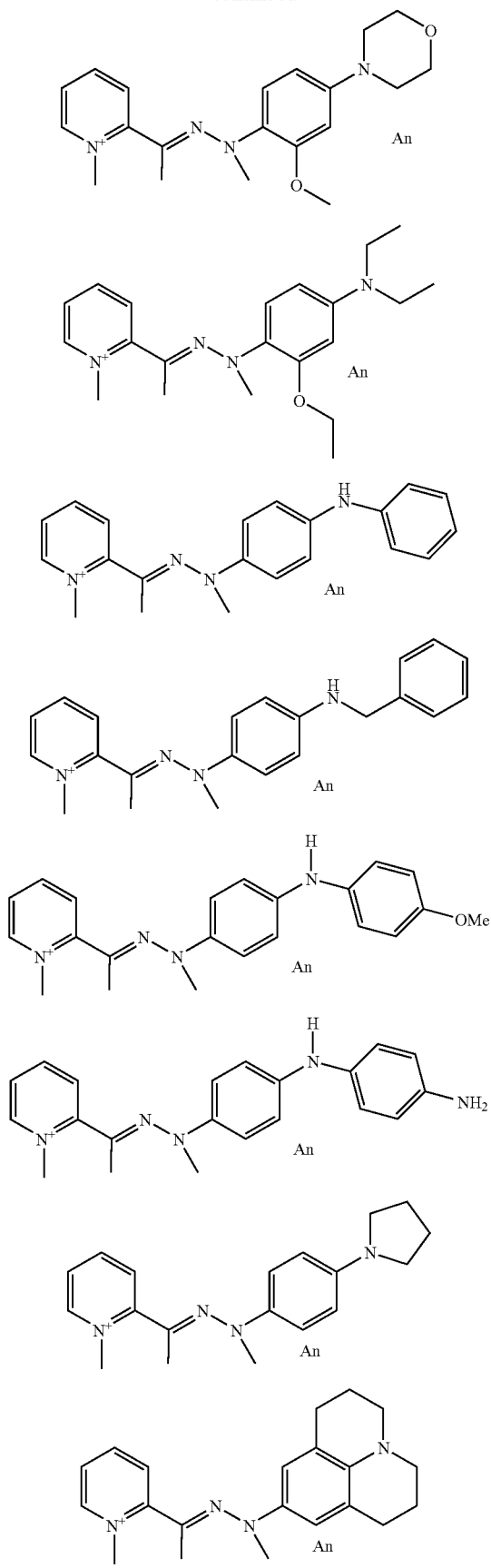
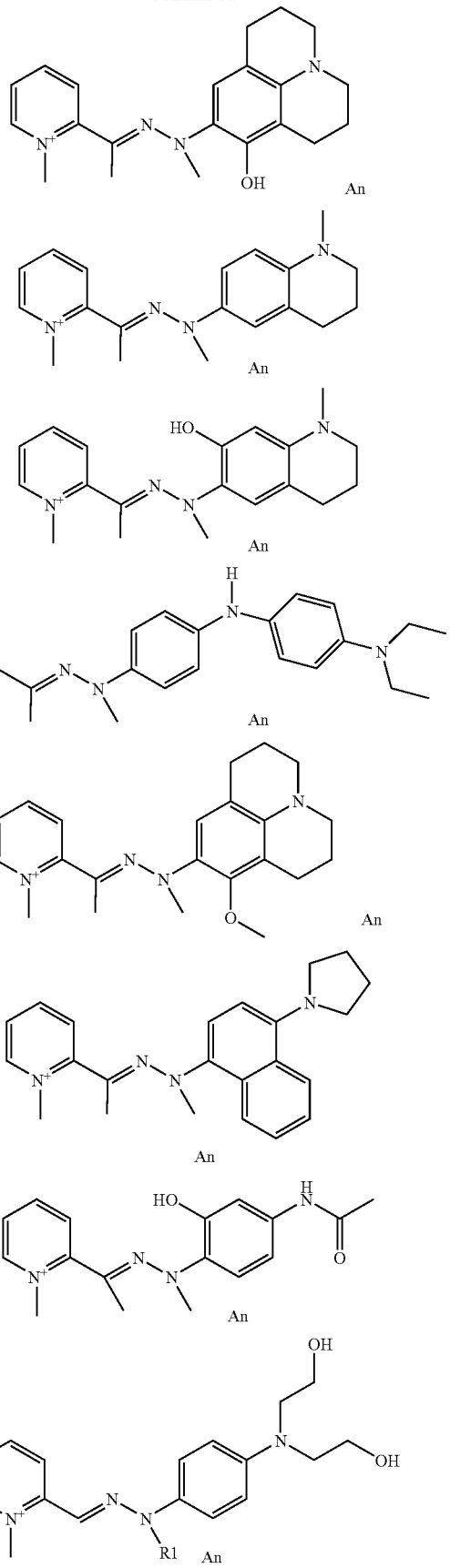

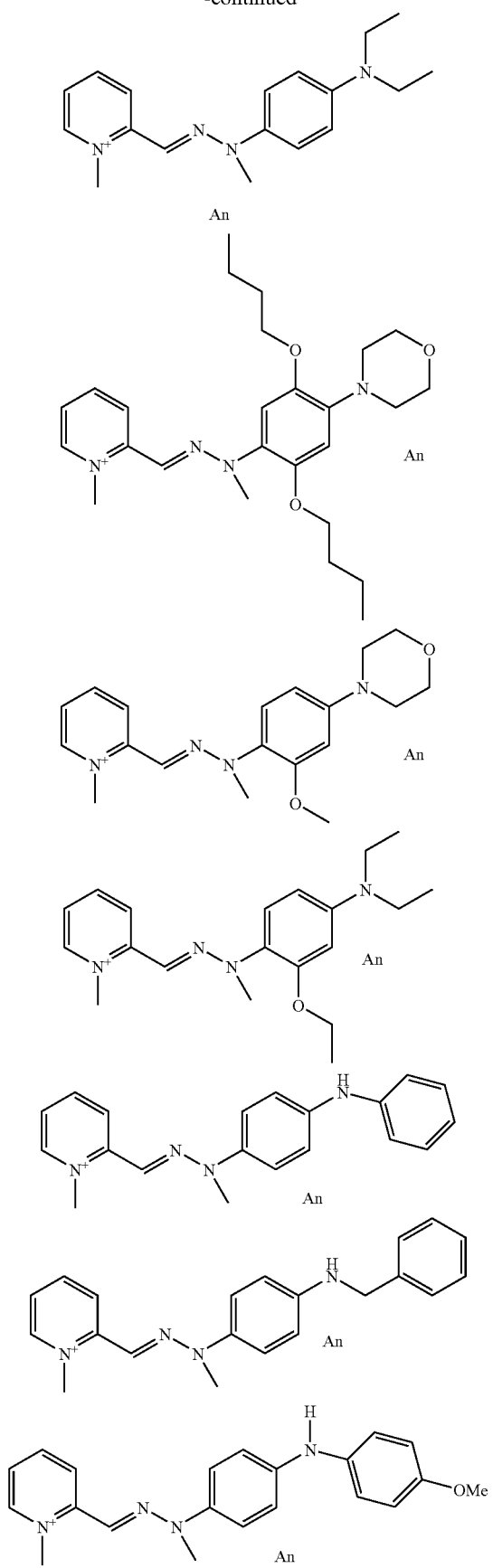
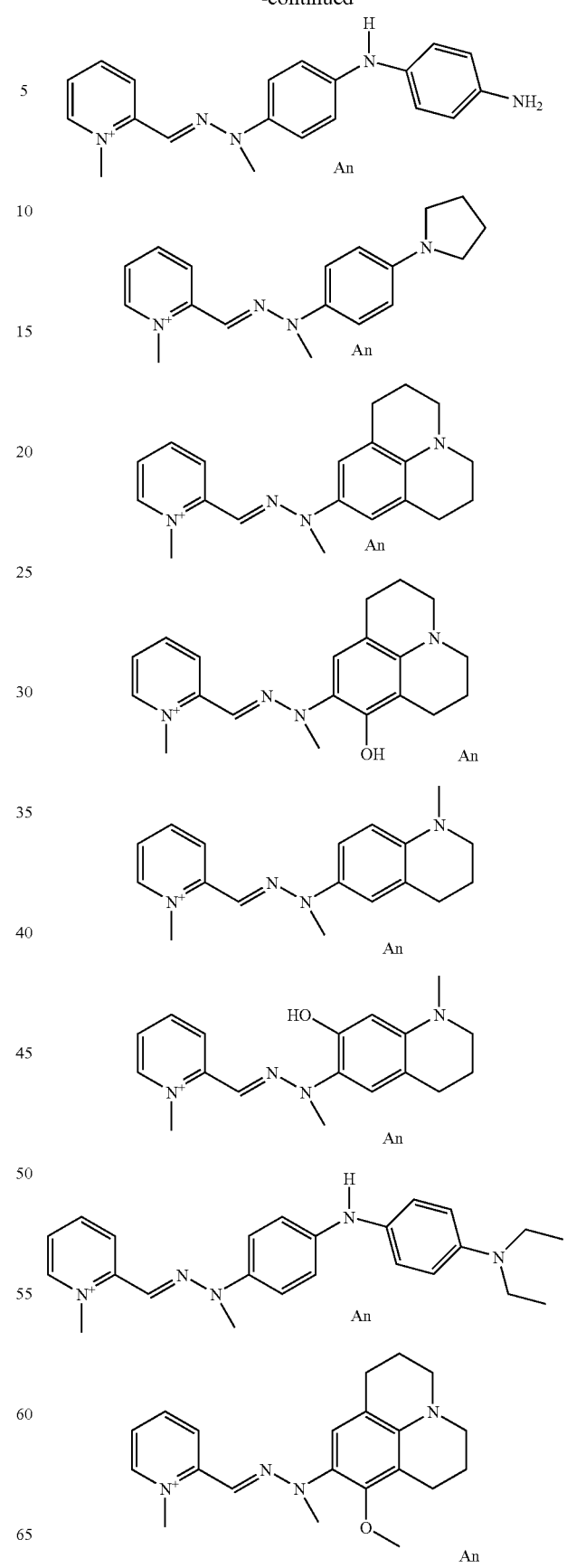

27
-continued
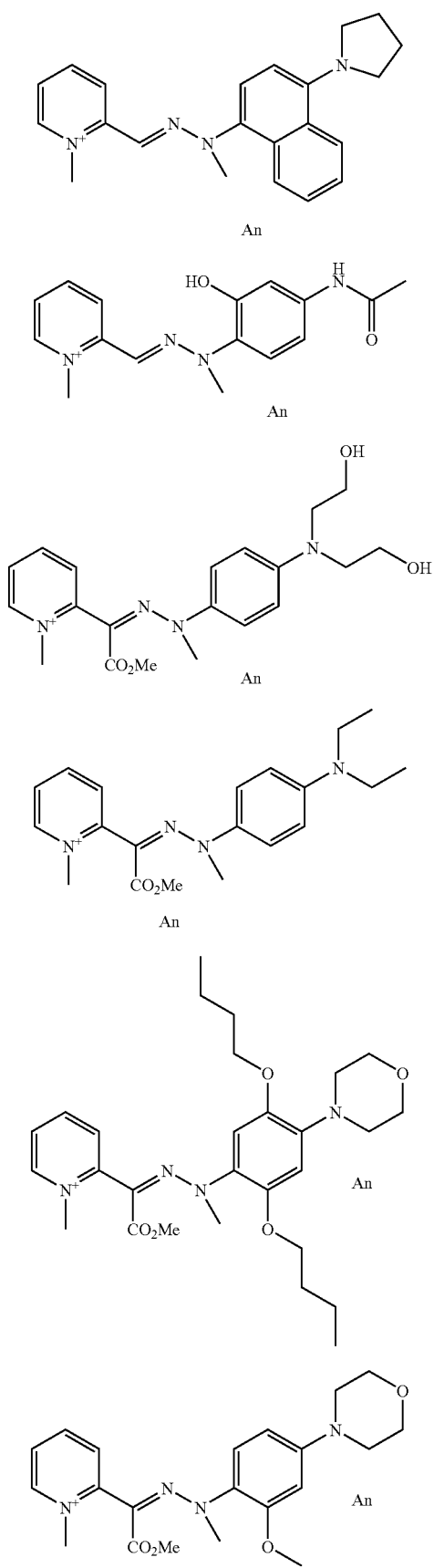
28
-continued
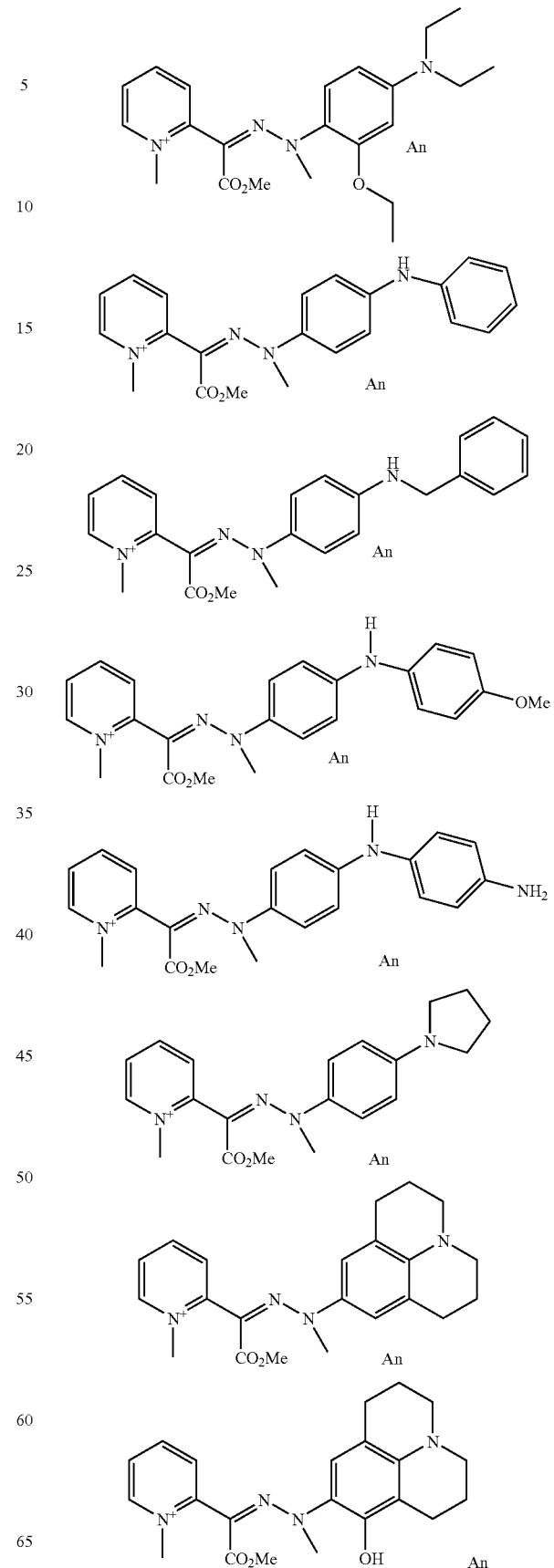

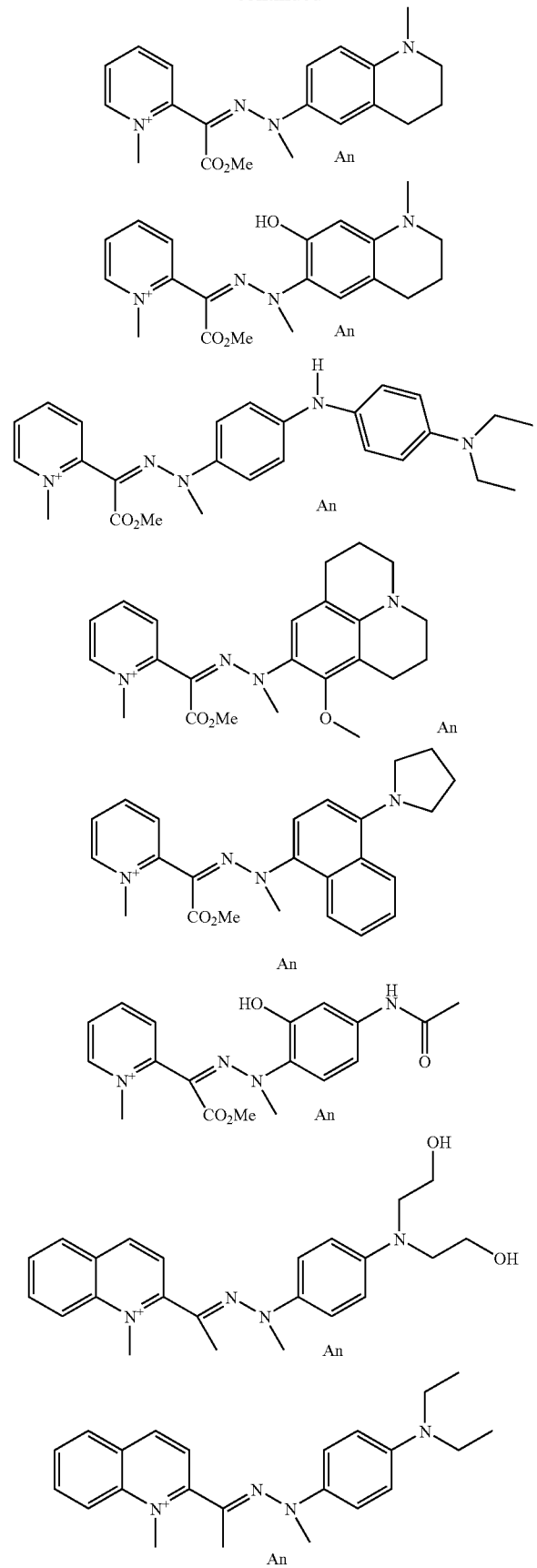
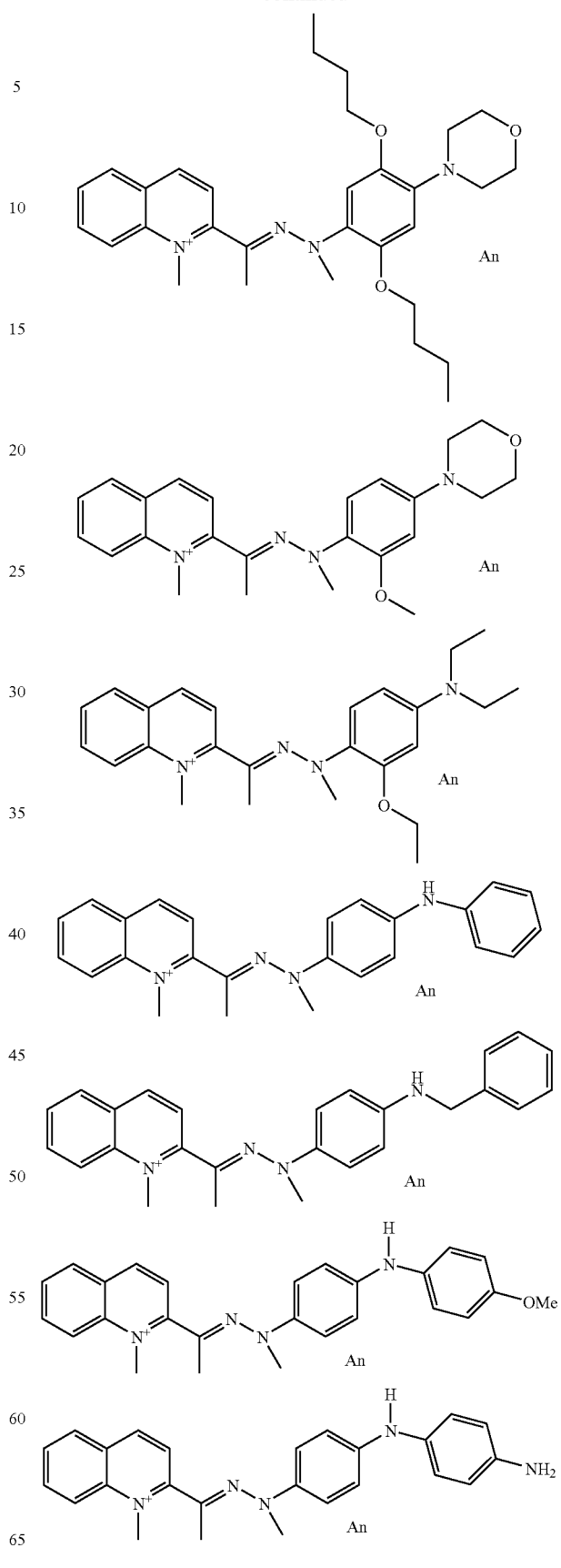

-continued
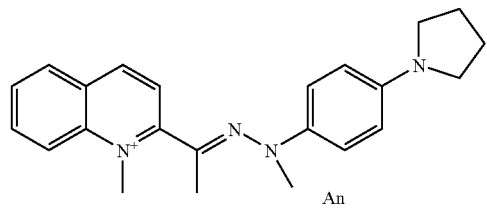
An
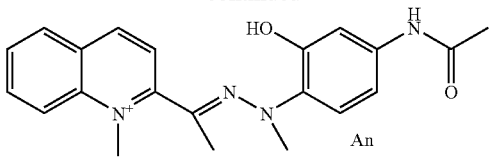
An
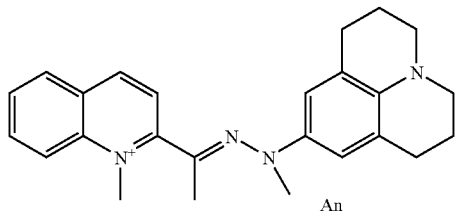
An
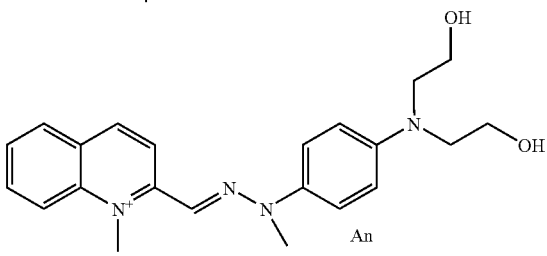
An
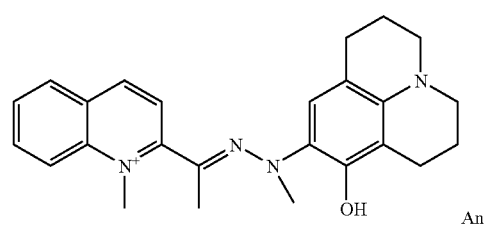
An
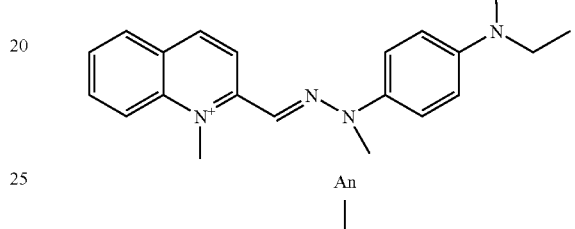
An
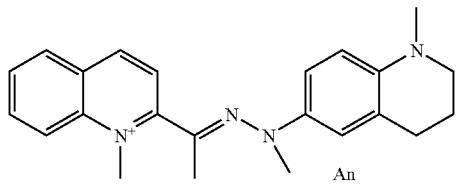
An
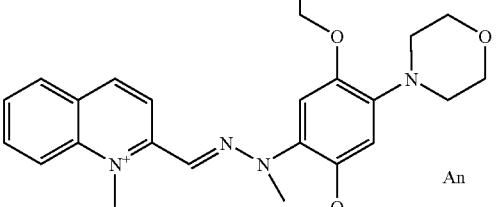
An
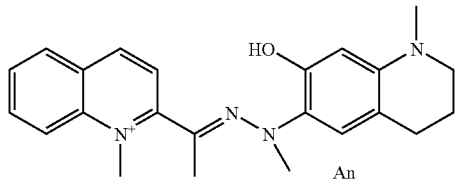
An
An
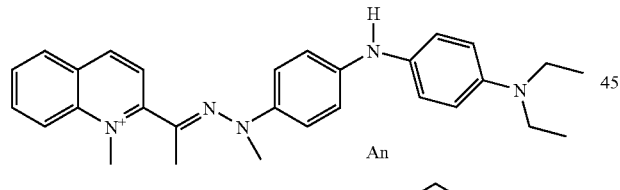
An
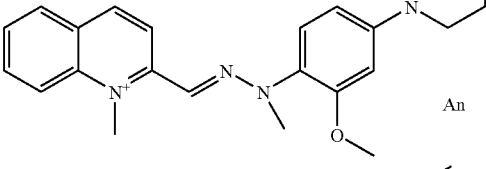
An
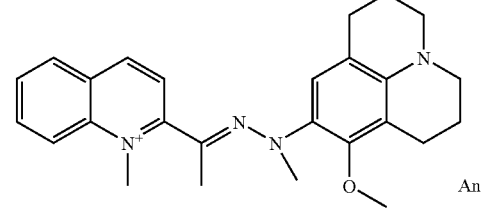
An
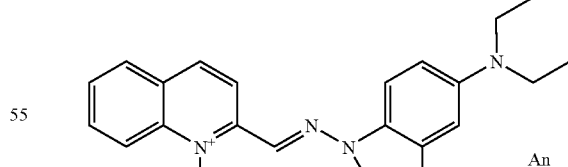
An
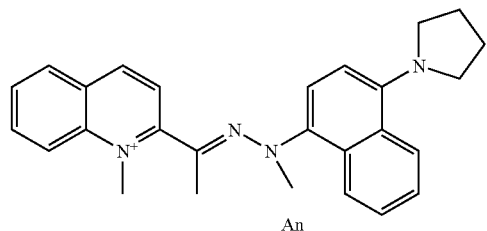
An
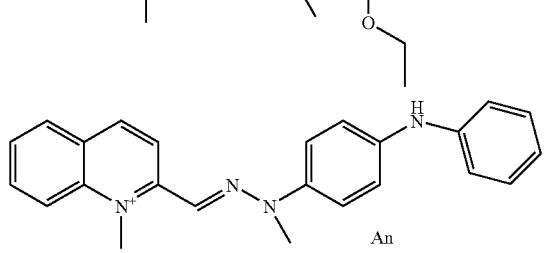
An 33
-continued
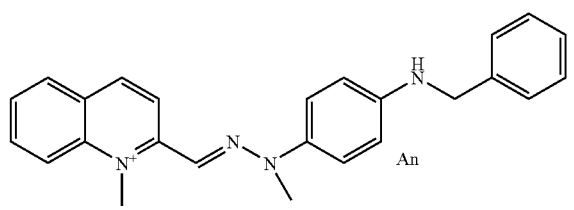
An
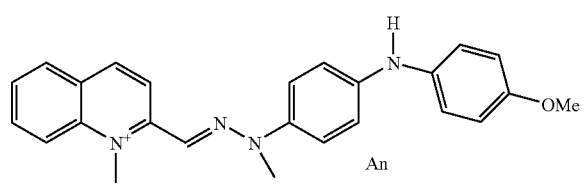
An
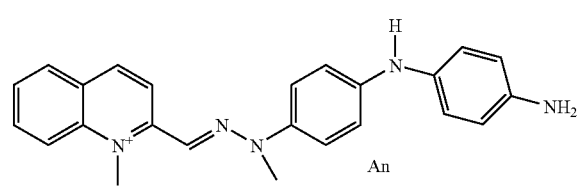
An
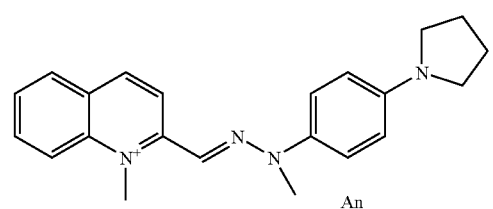
An
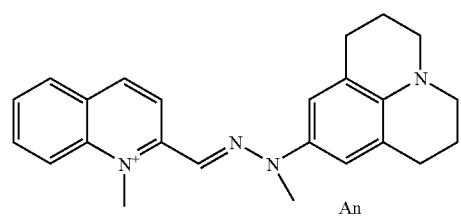
An
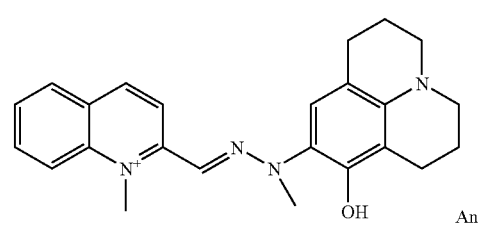
An
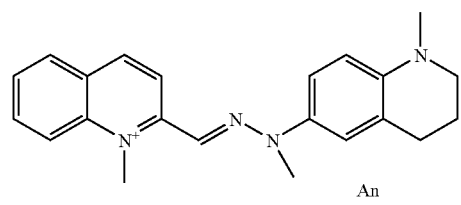
An
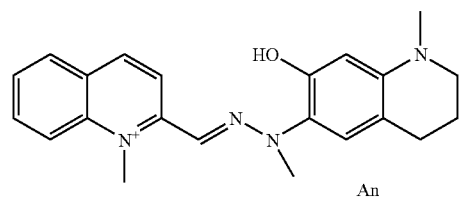
An
34
-continued
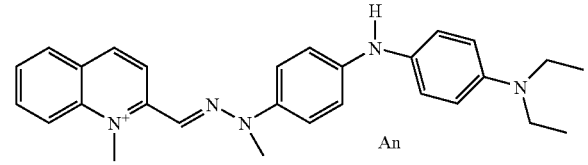
An
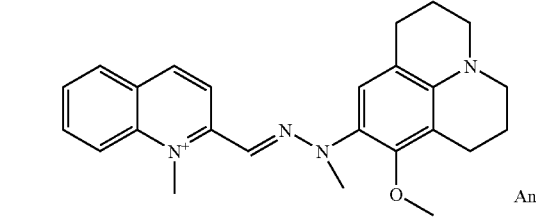
An
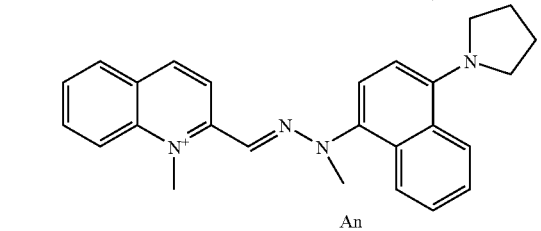
An
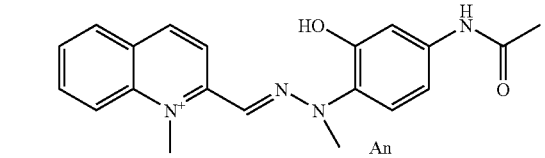
An
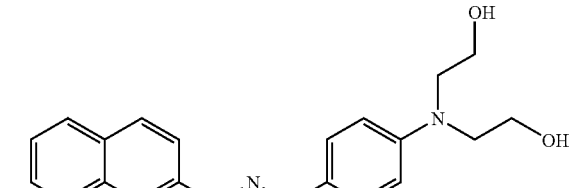
An
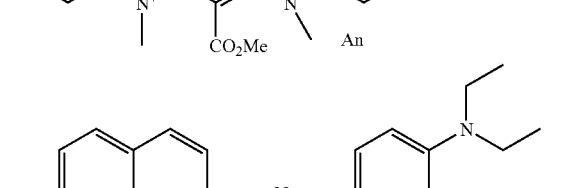
An
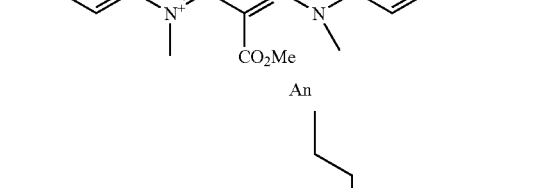
An
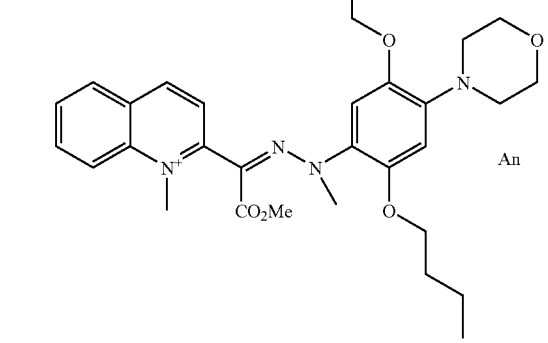
An 35
-continued
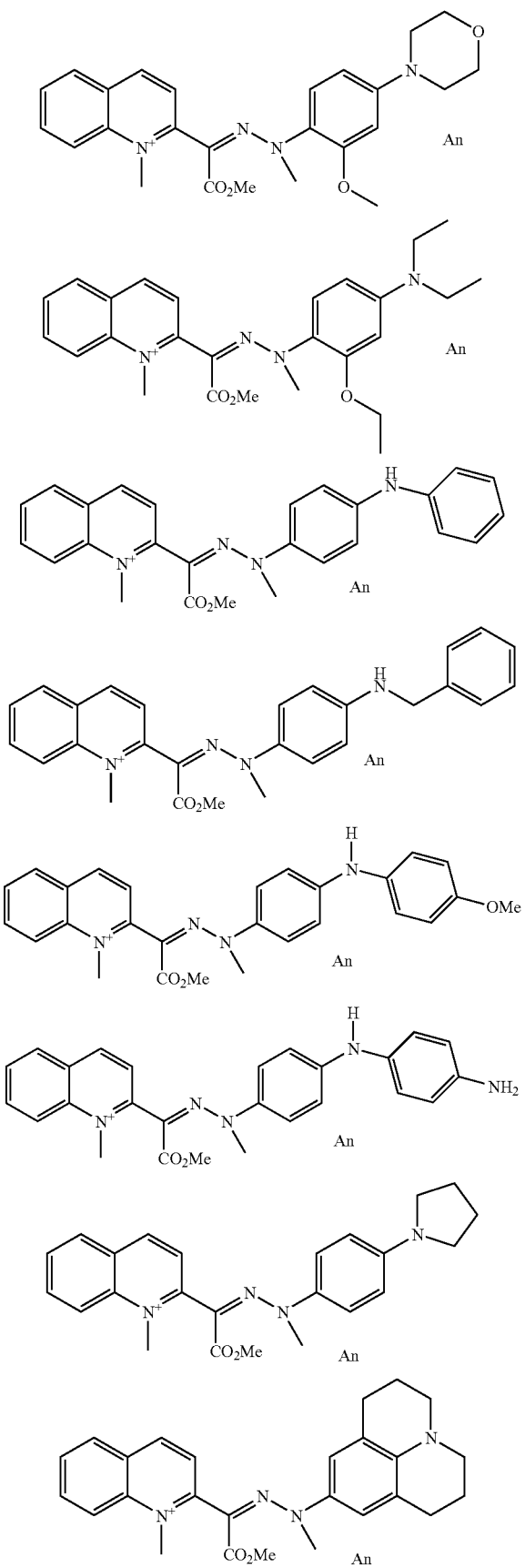
36
-continued
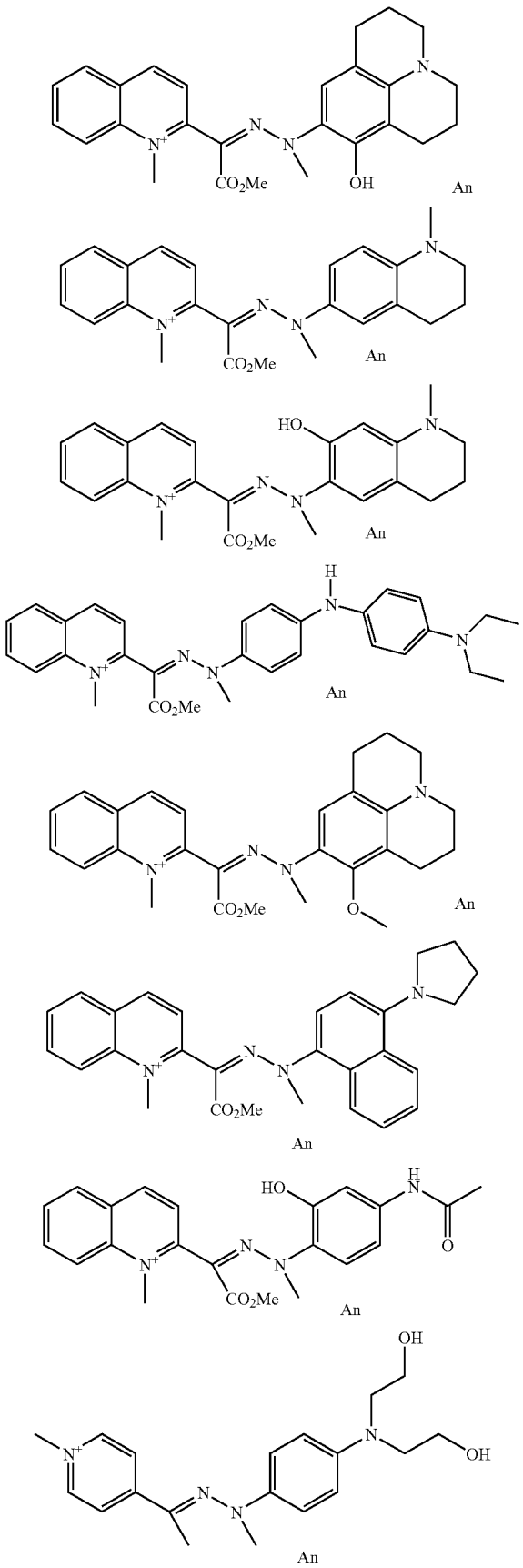

37
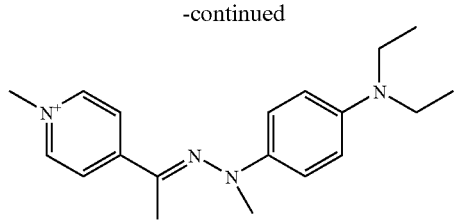
An
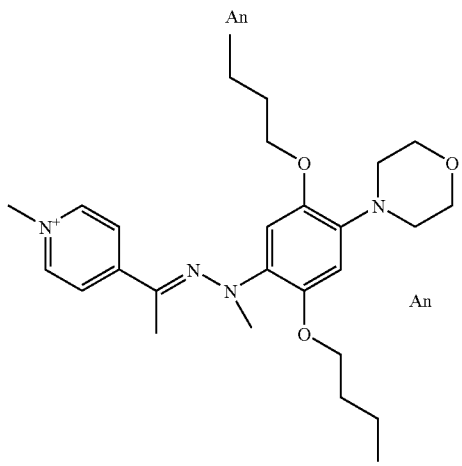
An
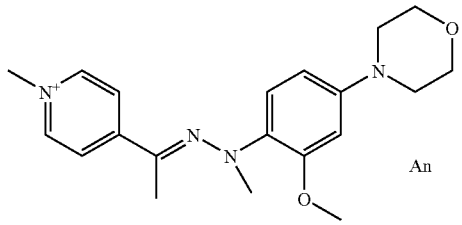
An
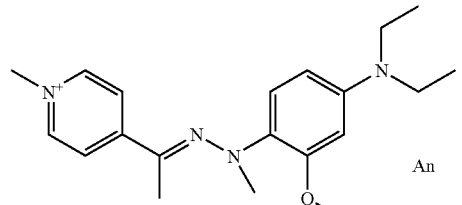
An
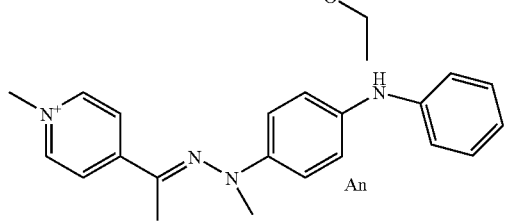
An
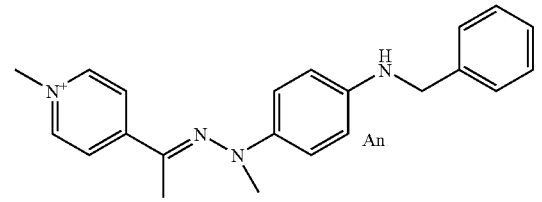
An
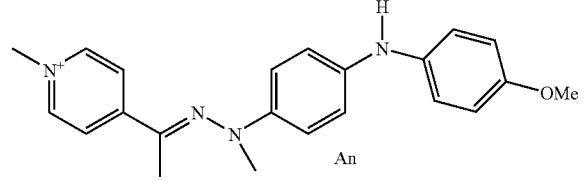
An
38
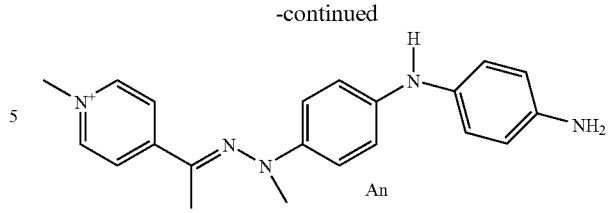
An
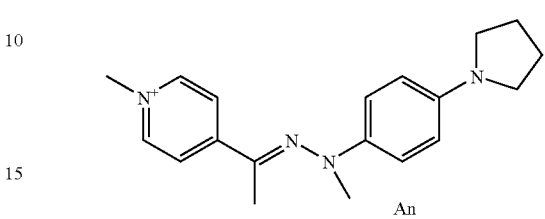
An
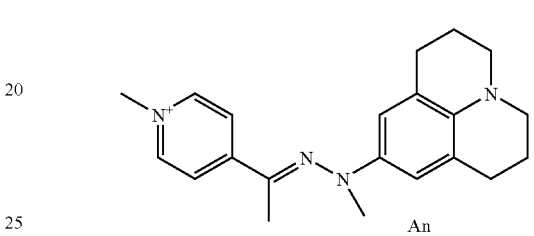
An
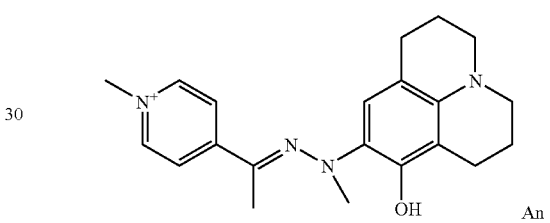
An
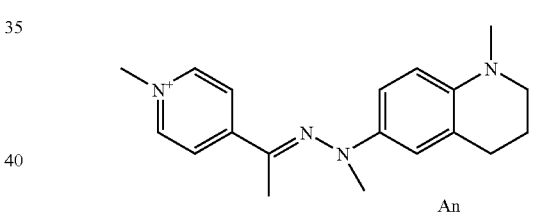
An
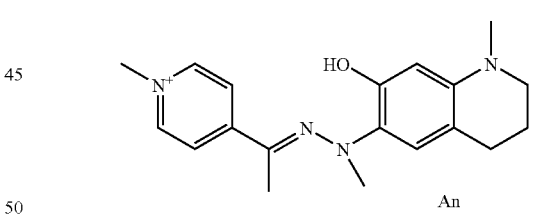
An
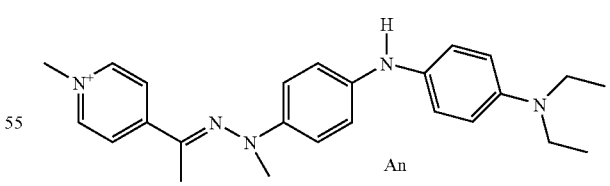
An
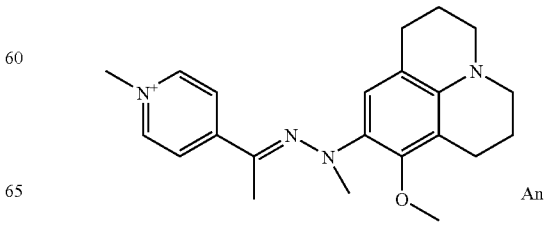
An

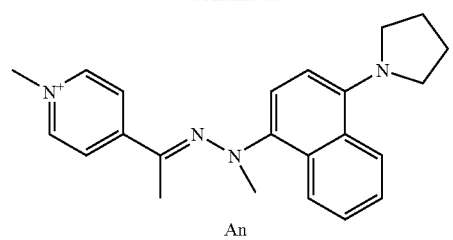
An
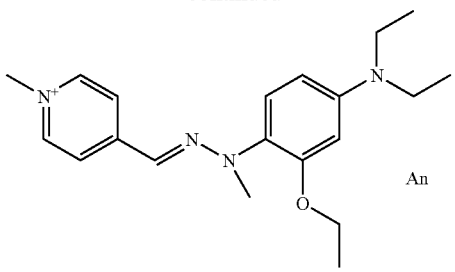
An
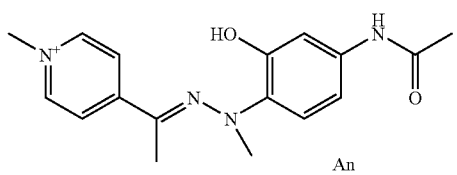
An
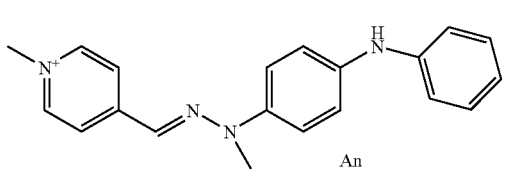
An
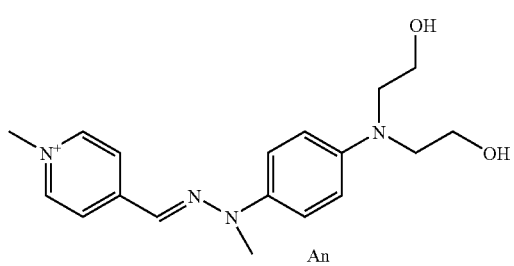
An
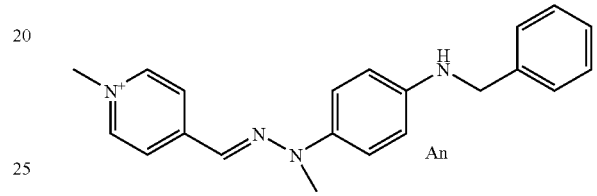
An
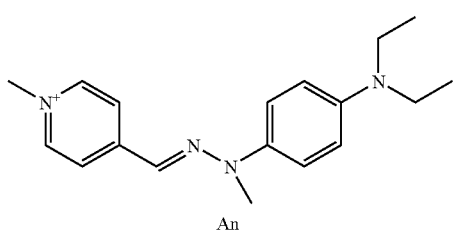
An
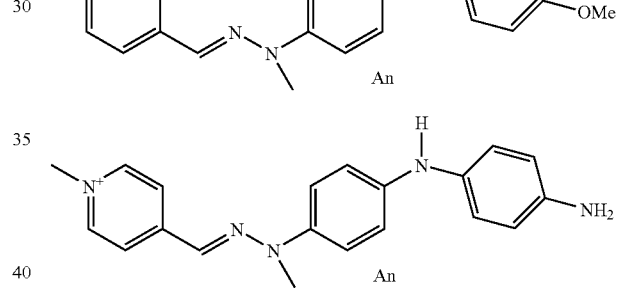
An
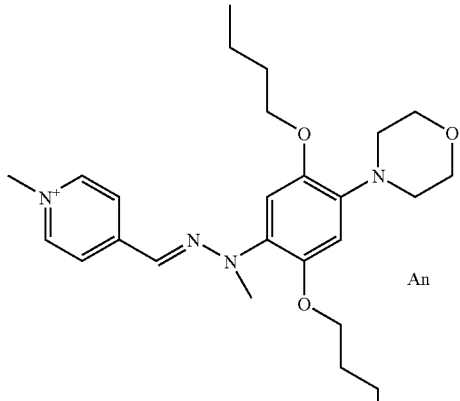
An
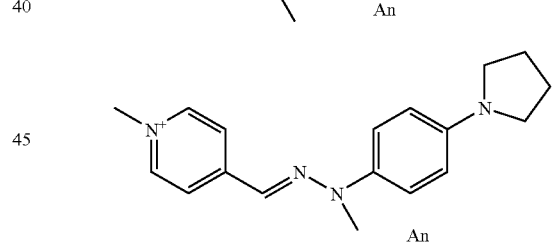
An
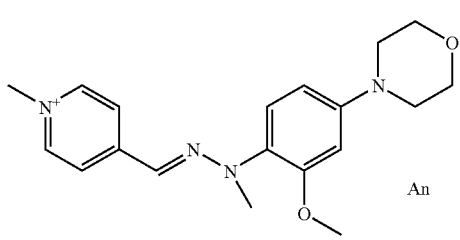
An
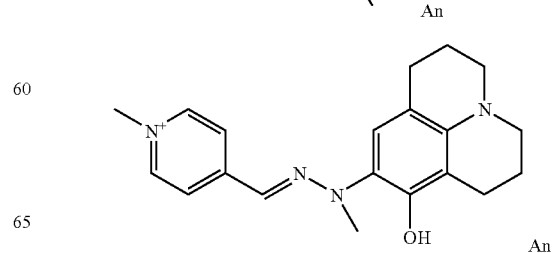
An 41
-continued
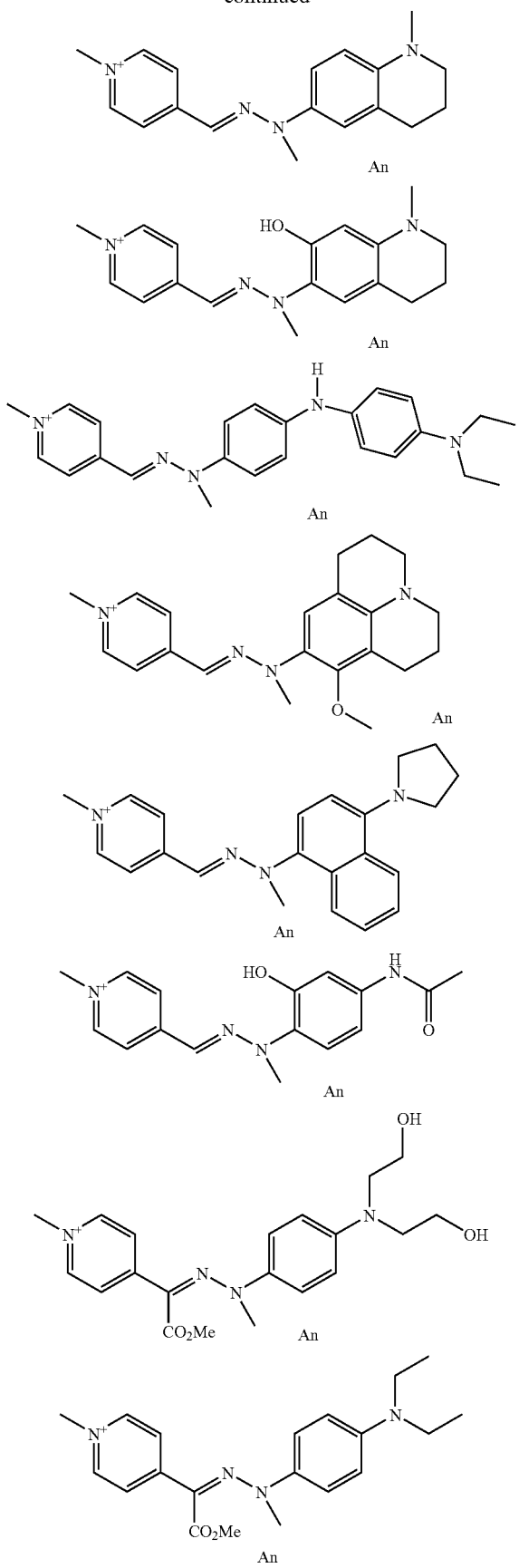
42
-continued
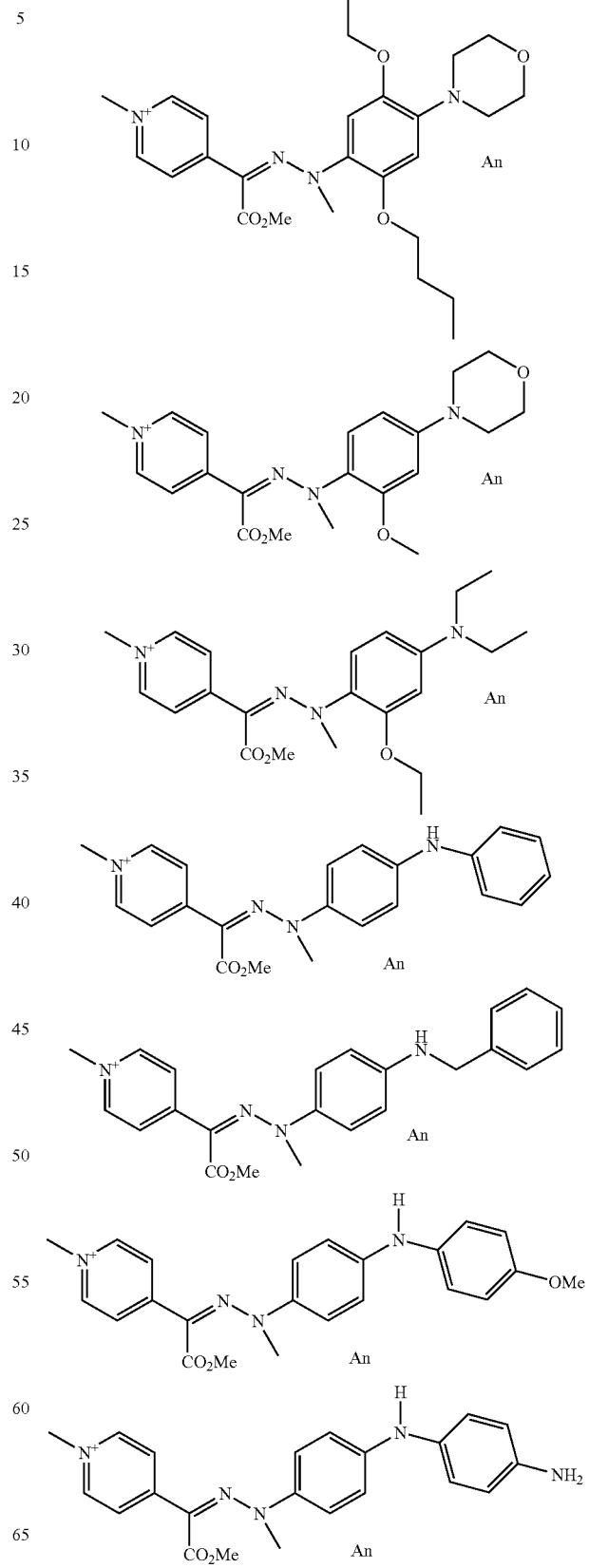

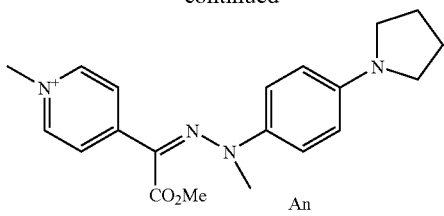
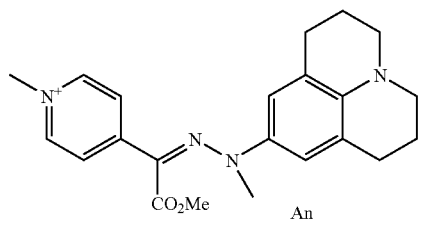
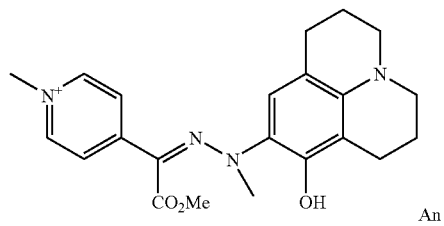
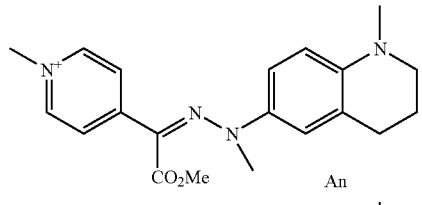
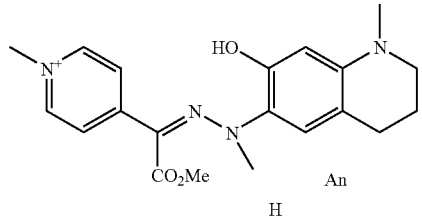
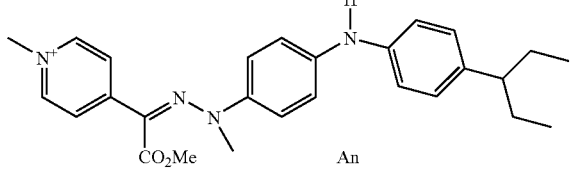
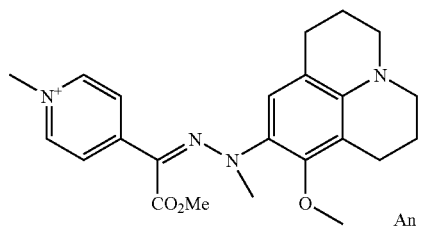
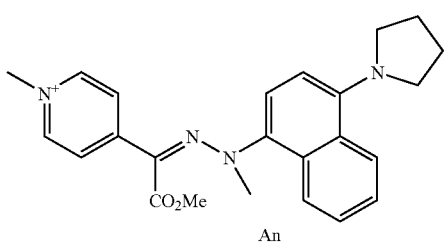
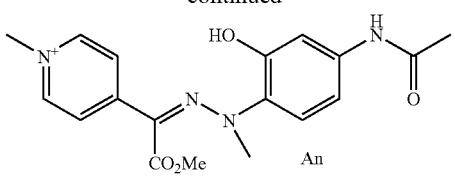
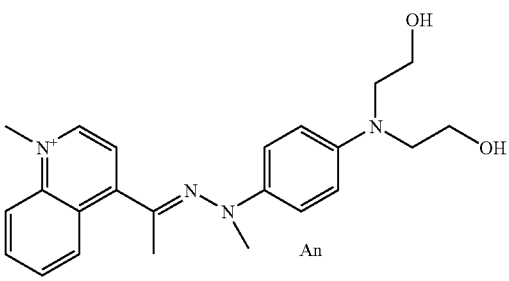
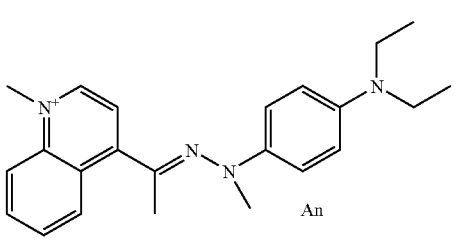
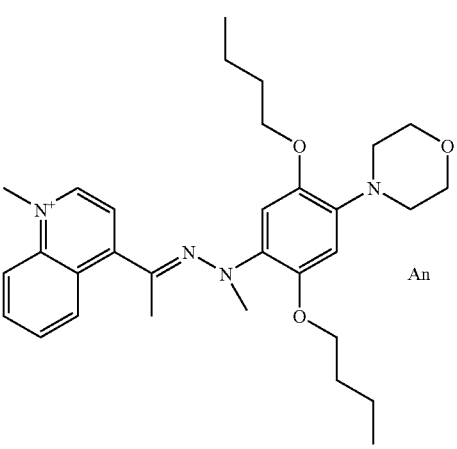
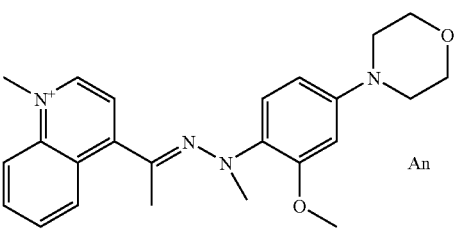
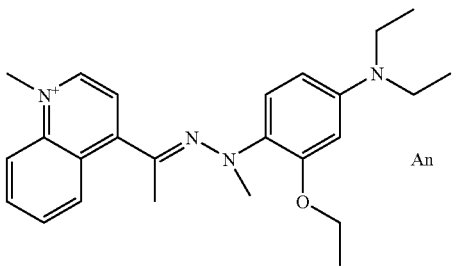

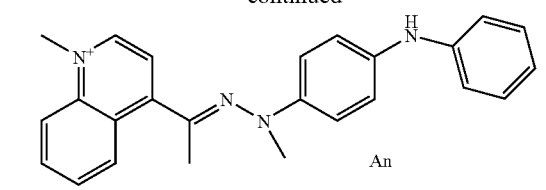
An
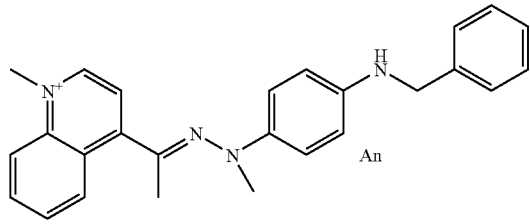
An
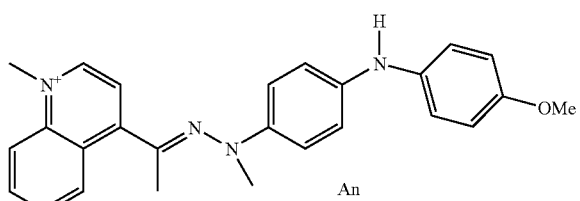
An
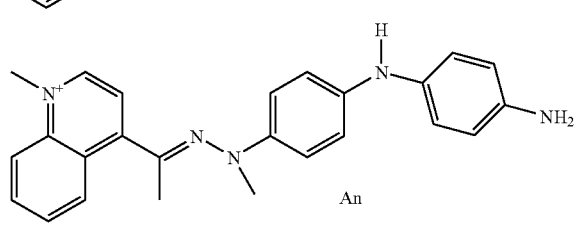
An
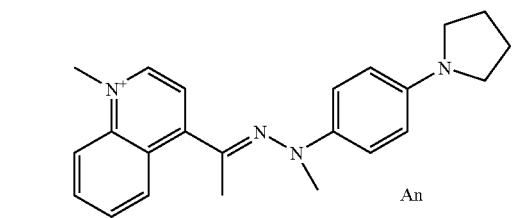
An
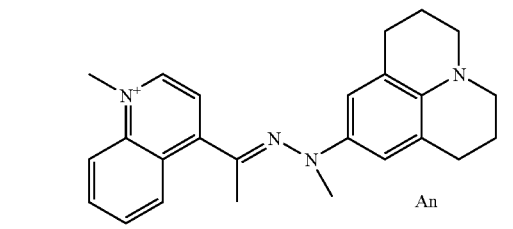
An
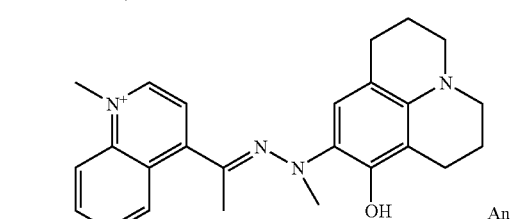
An
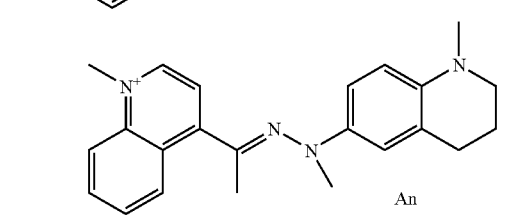
An
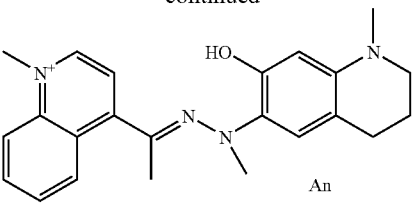
An
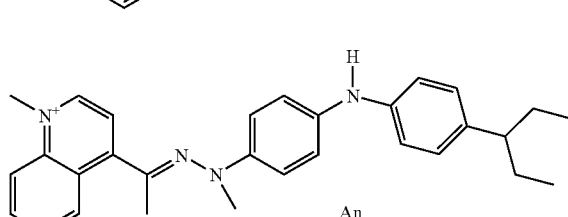
An
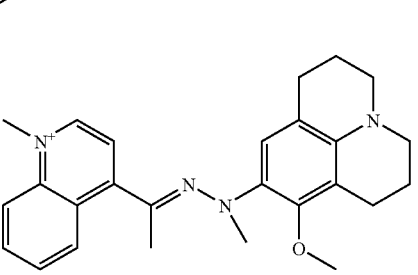
An
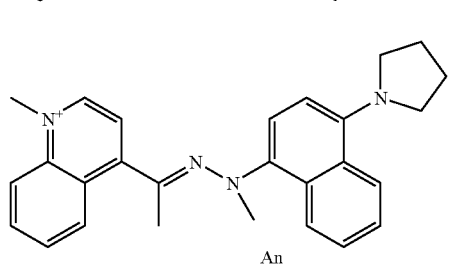
An
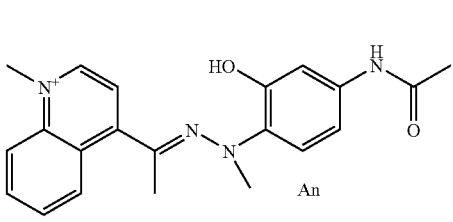
An
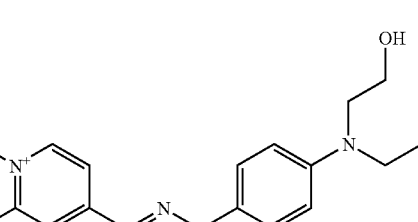
An
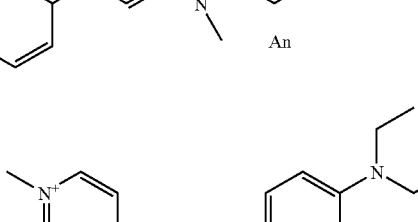
An
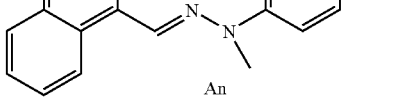
An

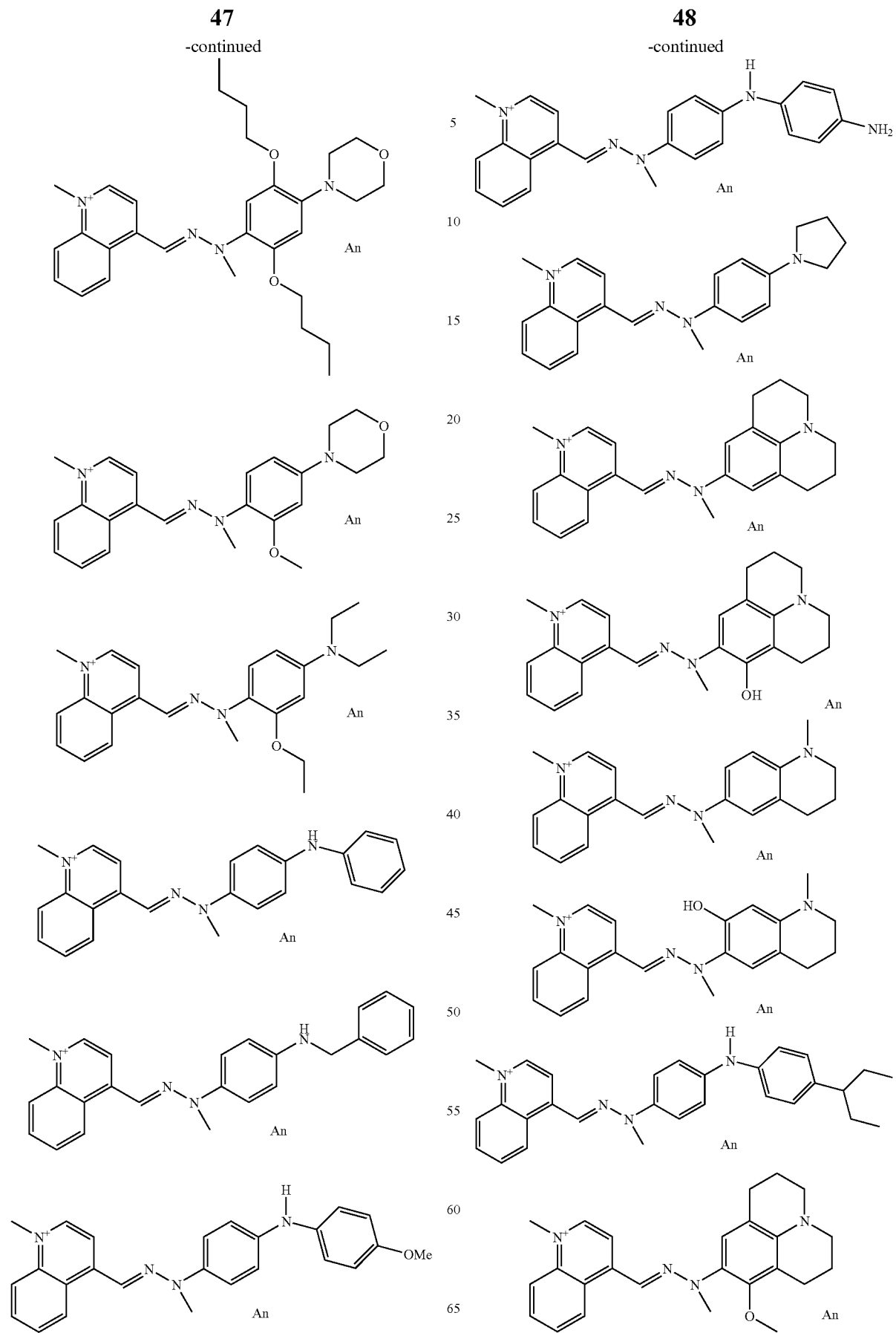

49
-continued
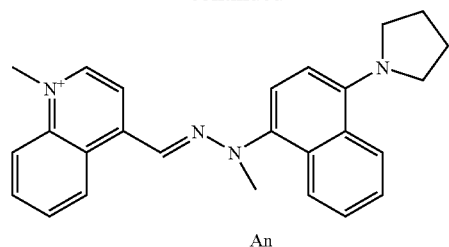
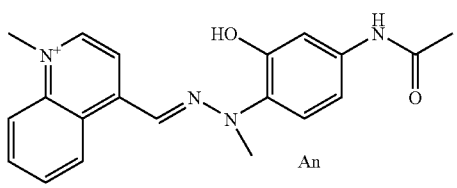
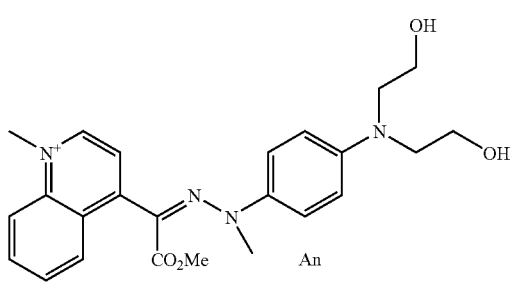
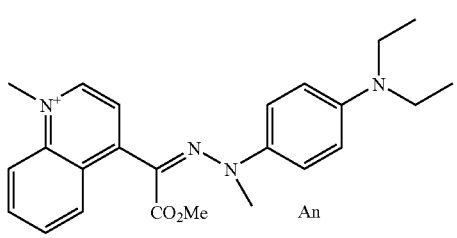
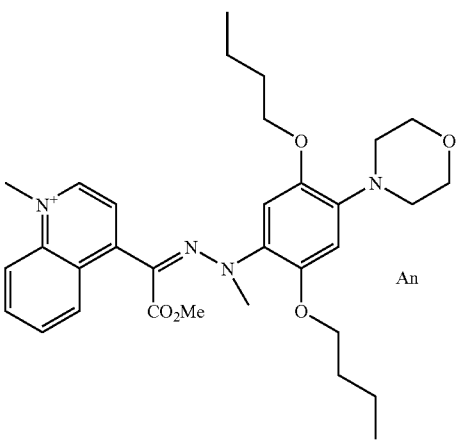
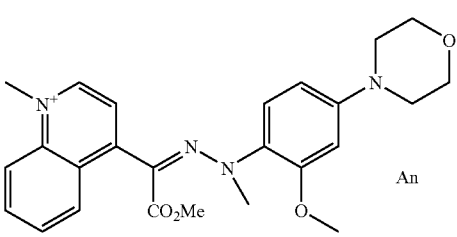
50
-continued
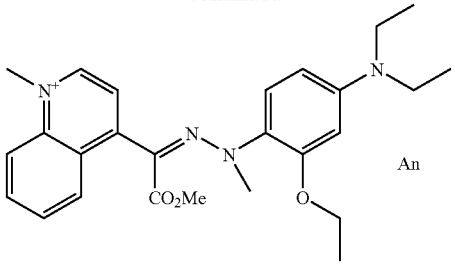
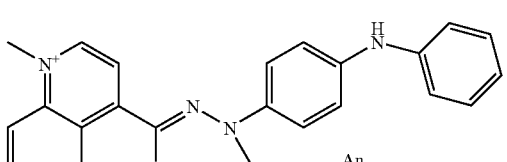
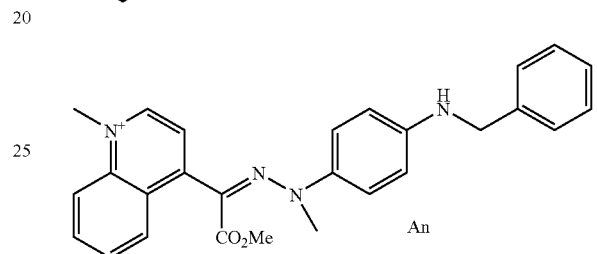
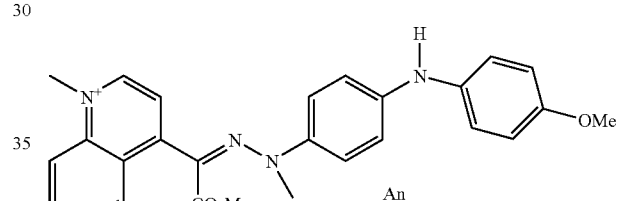
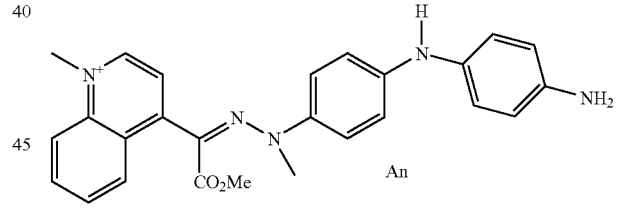
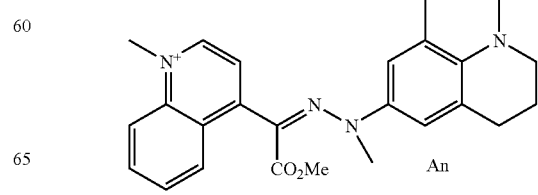

-continued

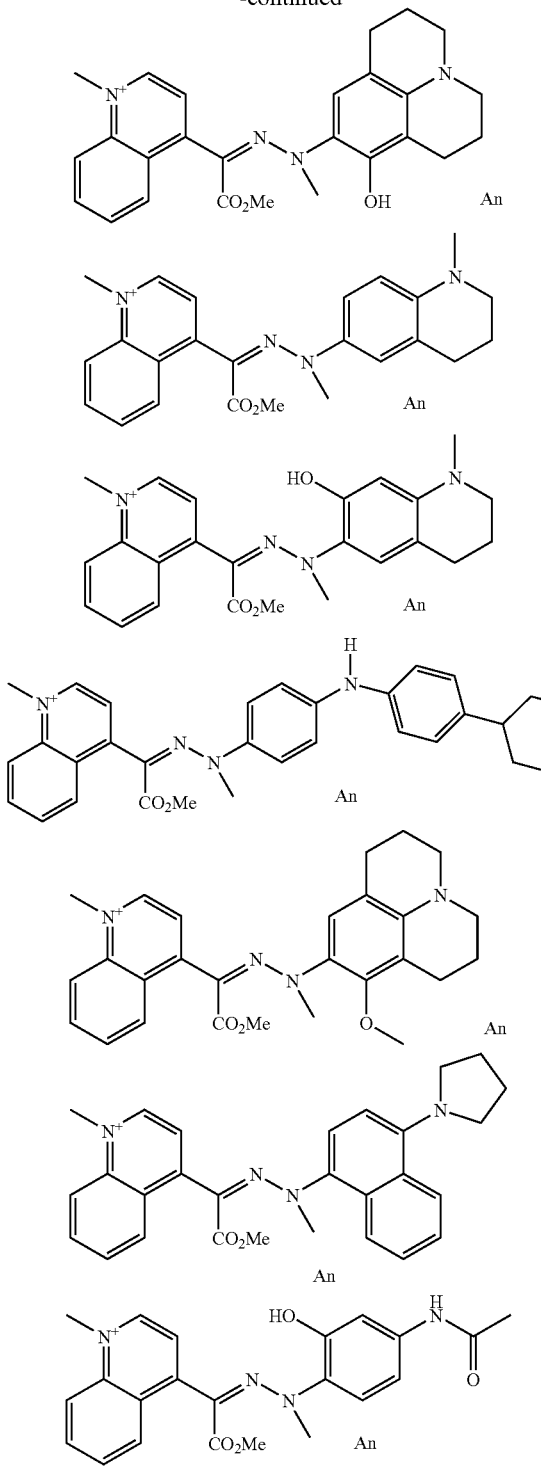

in which An is as defined previously.

Another subject of the invention relates to methods for preparing the compounds that have just been described.

According to a first embodiment, the compounds of formulae (I) and/or (II) can be obtained by carrying out the steps described below:

(a) Condensation of a heteroaromatic aldehyde or ketone with a hydrazine derivative:

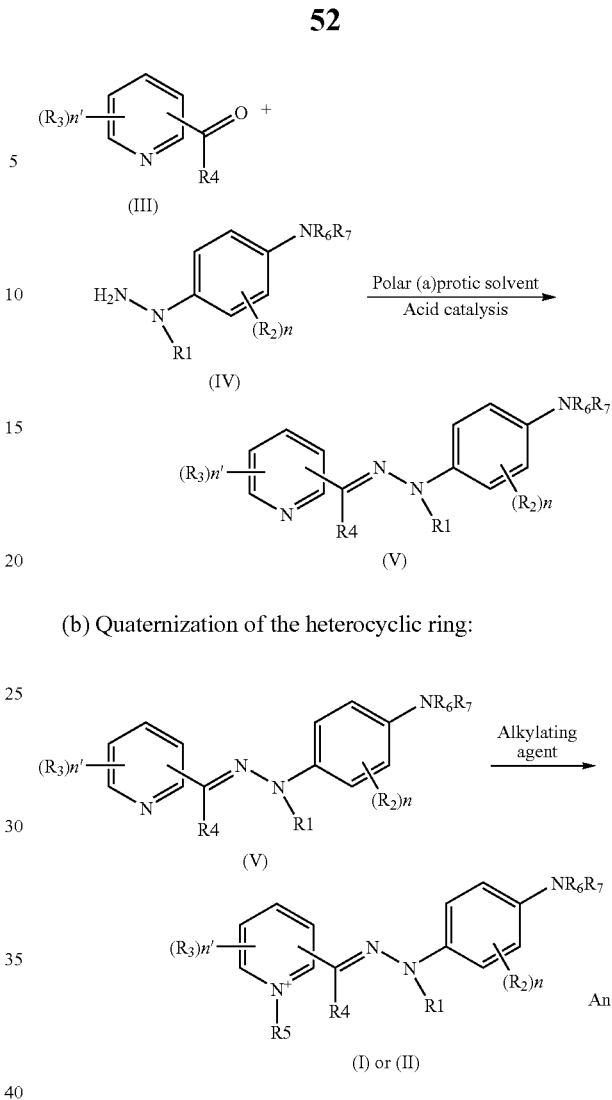

(b) Quaternization of the heterocyclic ring:

According to this method, a first step of condensation of a hydrazine derivative is carried out in the presence of a heteroaromatic aldehyde or ketone in a manner known to a person skilled in the art (for example, see Patent GB924601).

Usually, this reaction takes place at a temperature between −20° C. and 120° C., preferably between 0° C. and 70° C.

Conventionally, the reaction takes place in a suitable solvent such as, for example, water, alcohols such as methanol, ethanol or propanol; dimethylformamide, tetrahydrofuran, N-methylpyrrolidone, 1,3-dimethyl-2-oxohexahydropyrimidine or a mixture thereof.

The reaction usually takes place in the presence of a catalytic amount of acid chosen from organic acids such as acetic acid, propionic acid, para-toluenesulphonic acid or inorganic acids such as sulphuric acid or hydrochloric acid.

Once the reaction has been completed, a quaternization reaction is carried out in a second step.

Usually, this reaction is carried out in a solvent, which may be that from the preceding step or in another suitable organic solvent such as ethyl acetate, dichloromethane, 1,2-dichloroethane, toluene, etc.

The alkylating agent $R_5X$ may be an alkyl halide such as, for example, methyl iodide, 1-bromopropyl, 3-chlorohexane or else an alkyl or aryl sulphonate such as, for example, methyl 4-toluenesulphonate or benzyl 4-toluenesulphonate, or else a dialkylsulphate such as, for example, dimethylsulphate, diethylsulphate or dipropylsulphate.

The temperature is conventionally between 0 and 100° C., preferably between 20° C. and 70° C.

By way of example, this first method can be used for preparing the following compound:

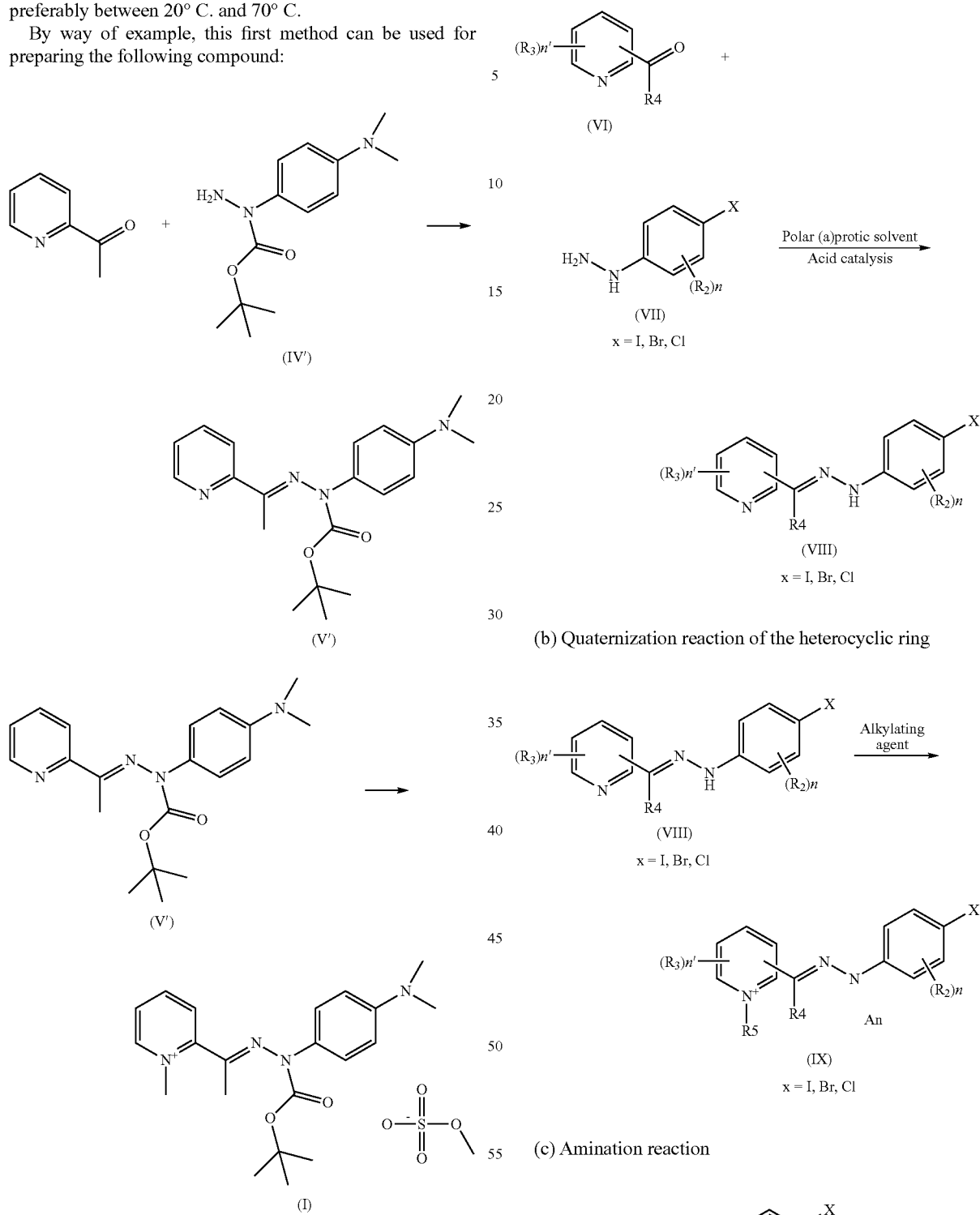

(b) Quaternization reaction of the heterocyclic ring (c) Amination reaction

It should be noted that the compound (IV') represented above may be obtained by using the procedure described in Org. Lett., 3, 23, 2001, 3803-3806 or WO99/43643.

According to a second embodiment, the compounds of formula (I) and/or (II) can be obtained by carrying out the steps described below:

(a) Condensation of a heteroaromatic aldehyde or ketone with a hydrazine derivative:

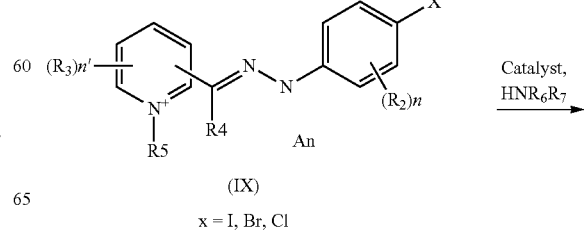

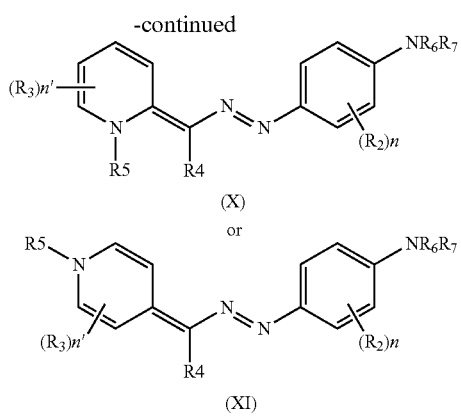

(d) Alkylation reaction

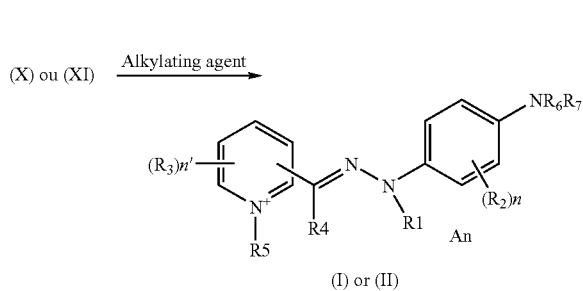

The conditions for carrying out steps (a) and (b) are the same as those described in the preceding synthesis variant and reference may be made thereto.

In a third step, an amination reaction is carried out between the aryl halide obtained previously and an aliphatic or aryl amine $HNR_6R_7$ in a manner known to a person skilled in the art.

When $HNR_6R_7$ is an aliphatic amine, the amination reaction can take place via catalysis with copper ($CuI$, $Cu_2O$, etc.). By way of example, this step could be carried out by taking inspiration from the procedures described in the following publications:

Org. Lett. 4, 4, 2002, 581-584;
Org. Lett. 5, 6, 2003, 793-796; and
Tetrahedron 61, 27, 2005, 6553-6560.

When $HNR_6R_7$ is an aliphatic or aromatic amine, the amination reaction can take place via catalysis with palladium ($Pd_2(dba)_3$, Pd $(OAc)_2$, etc.). By way of example, this step could be carried out by taking inspiration from the procedures described in the following publications:

J. Org. Chem. 69, 2004, 9135-9142; and
Ang. Chem. Int. Ed. Engl, 34, 12, 1995, 1348-1350.

Once the reaction has been completed, an alkylation reaction is carried out, in a fourth step, in the presence of an inorganic base (MgO, $K_2CO_3$, $Na_2CO_3$, etc.).

The alkylating agent $R_1X$ may be an alkyl halide such as, for example, methyl iodide, 1-bromopropyl, 3-chlorohexane or else an alkyl or aryl sulphonate such as, for example, methyl 4-toluenesulphonate or benzyl 4-toluenesulphonate, or else a dialkylsulphate such as, for example, dimethylsulphate, diethylsulphate or dipropylsulphate.

Usually, this reaction is carried out in another suitable organic solvent such as dichloromethane, isopropanol, ethyl acetate, 1,2-dichloroethane, toluene, etc.

The temperature is conventionally between 0 and 100° C., preferably between 20° C. and 70° C.

By way of example, this second method can be used for preparing the following compound:

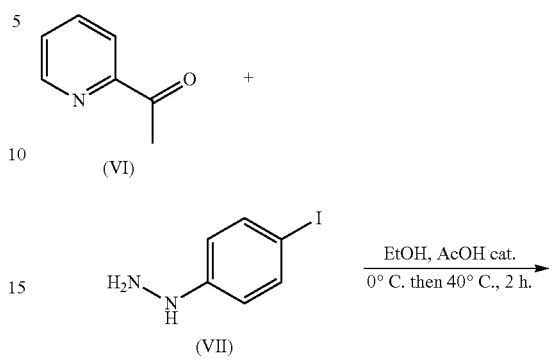

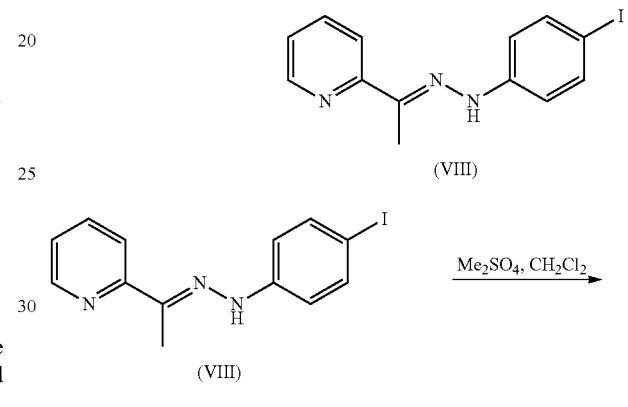

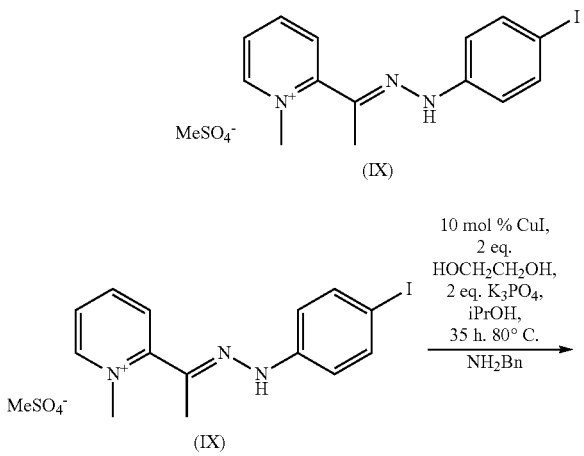

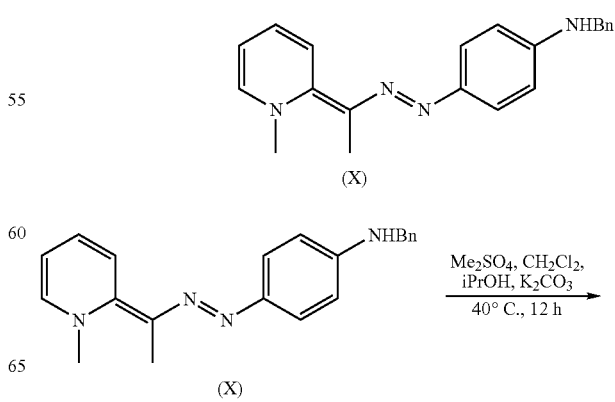

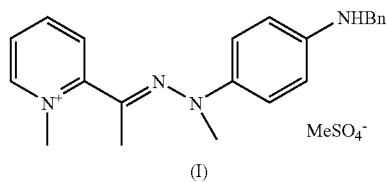

(I)

According to a third embodiment, the compounds of formula (I) and/or (II) can be obtained by carrying out the steps described below:

(a) Quaternization reaction

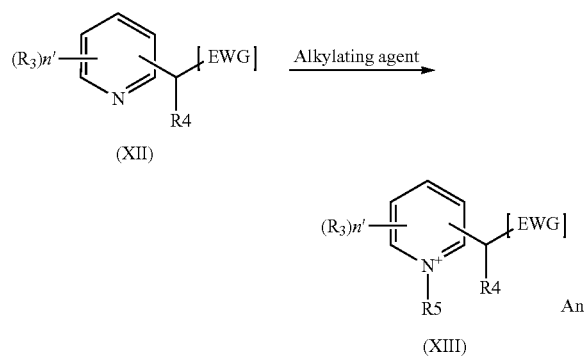

EWG = Electron-withdrawing group b) Coupling reaction of a diazonium salt to an activated system

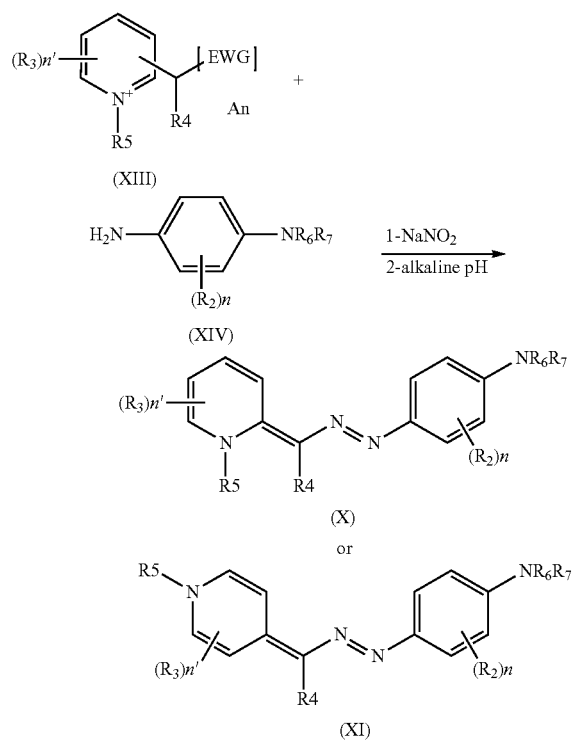

(c) Alkylation reaction

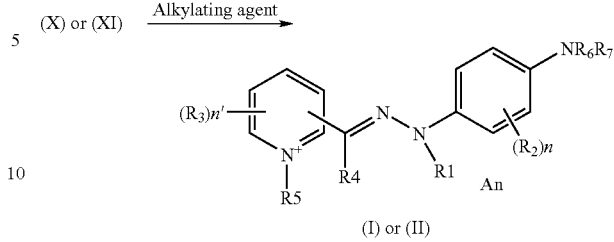

(I) or (II)

According to this method, a first step of quaternization of the compound (XII) is carried out. Usually, this reaction is carried out in a suitable solvent, amongst which mention may be made of alcohols such as methanol, ethanol, propanol or isopropanol; dimethylformamide, tetrahydrofuran, N-methylpyrrolidone, 1,3-dimethyl-2-oxohexahydropyrimidine, ethyl acetate, 1,2-dichloroethane, toluene, etc.

The alkylating agent $R_5X$ may be an alkyl halide such as, for example, methyl iodide, 1-bromopropyl, 3-chlorohexane or else an alkyl or aryl sulphonate such as, for example, methyl 4-toluenesulphonate or benzyl 4-toluenesulphonate, or else a dialkylsulphate such as, for example, dimethylsulphate, diethylsulphate or dipropylsulphate.

The temperature is conventionally between 0° C. and 100° C., preferably between 20° C. and 70° C.

The compounds (XII) are commercial or may be obtained, for example, from the procedures described in:
Chem. Pharm. Bull 30(5) 1680-1691, 1982; and
Tet. Lett. 27(49) 6005-8, 1986.

In a second step, a reaction for coupling a diazonium salt obtained from an aromatic amine (XIV) to the previously obtained compound (XIII) is carried out in a manner known to a person skilled in the art (see, by way of example, Patent FR2123267).

Usually, this reaction is carried out in a suitable solvent such as, for example, water or alcohols such as methanol, ethanol, propanol or isopropanol.

The temperature is conventionally between −20 and 40° C. preferably between −5° C. and 20° C.

The pH of the reaction is between 1 and 13 preferably between 3 and 12. The pH may be controlled using organic or inorganic acids such as acetic acid, propionic acid, hydrochloric acid, hydrobromic acid, hydroiodic acid or sulphuric acid, or using inorganic bases such as potassium, sodium and caesium carbonates, sodium, potassium, and lithium hydroxides, etc.

In this second step, it is also possible to use commercially available diazonium salts, such as:

Structures of commercial diazonium salts

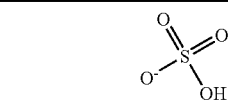

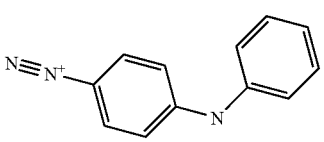

Structures of commercial diazonium salts
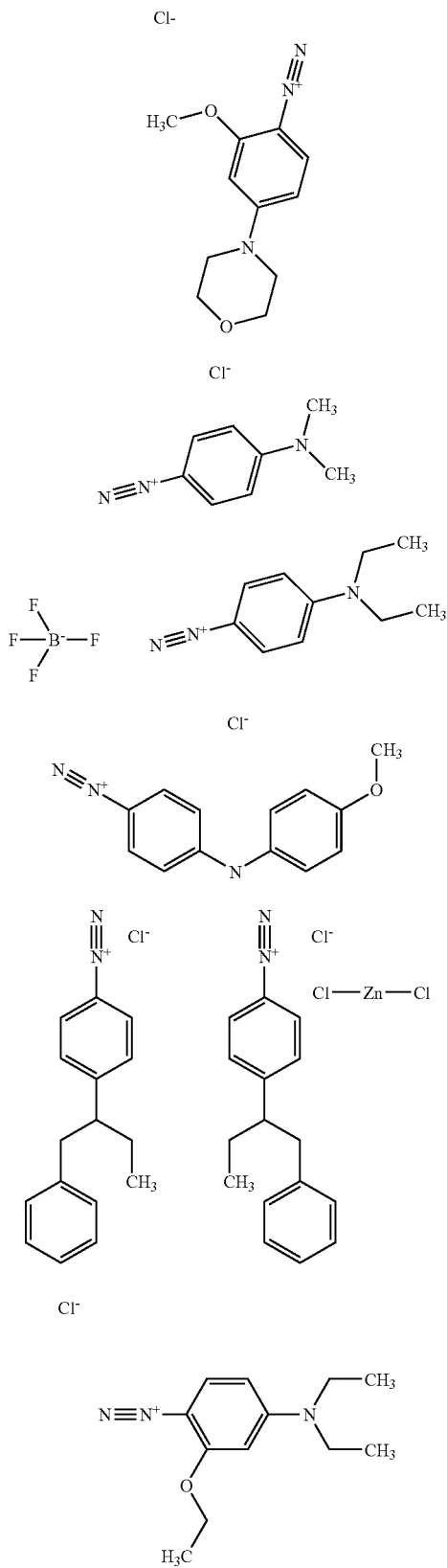
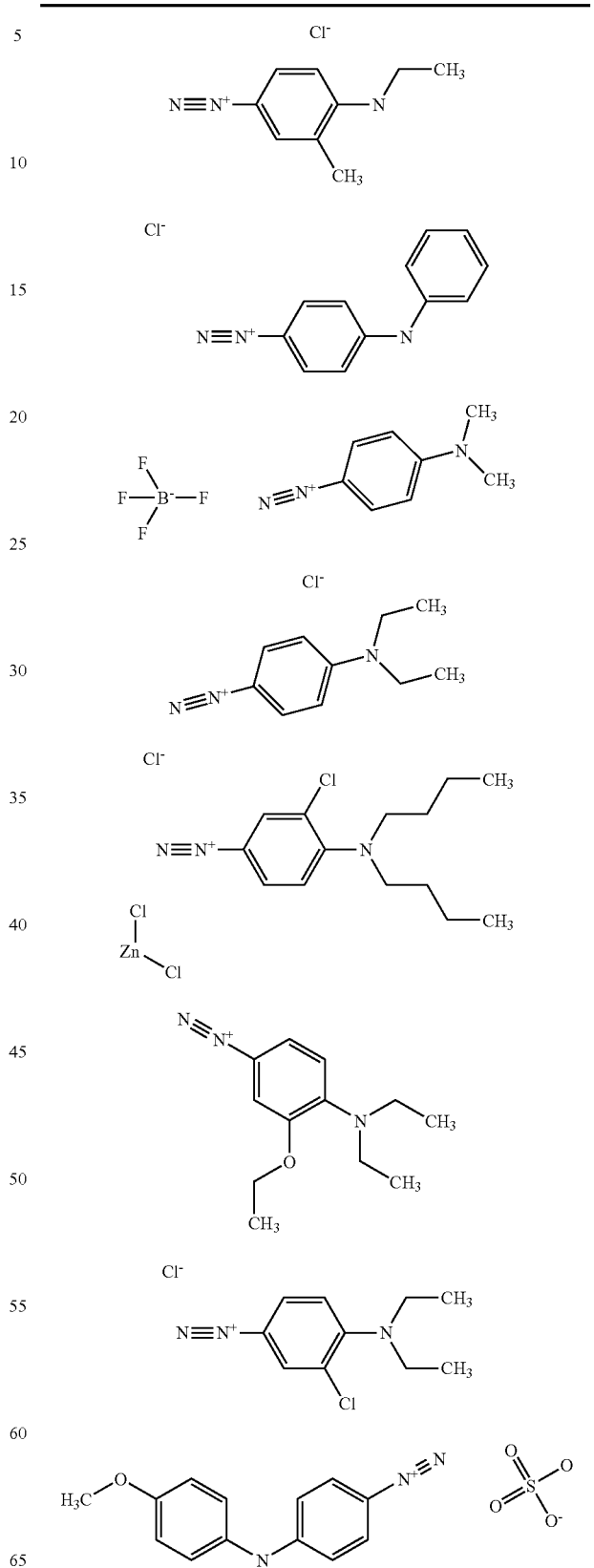

TABLE-continued
Structures of commercial diazonium salts
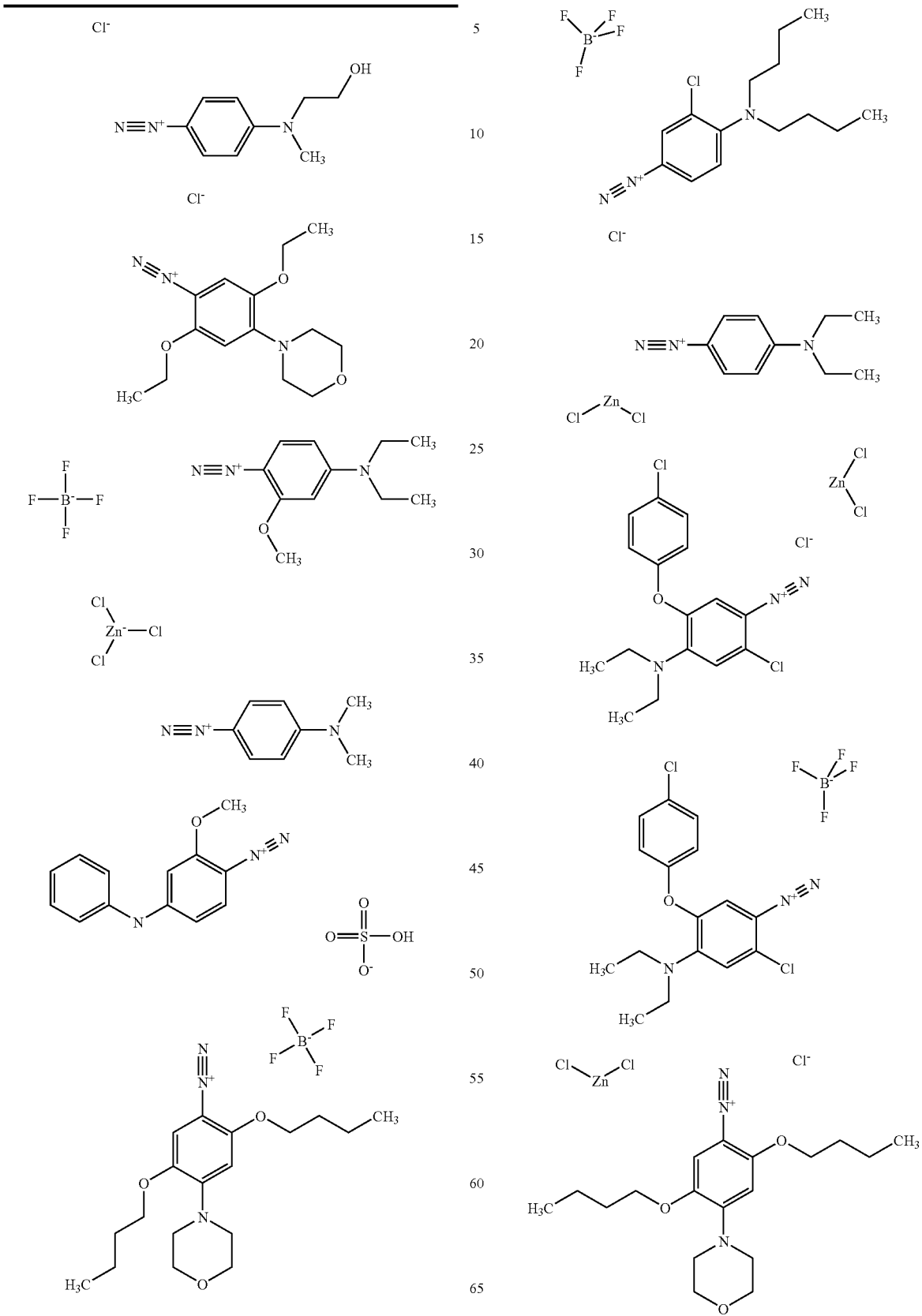

Structures of commercial diazonium salts

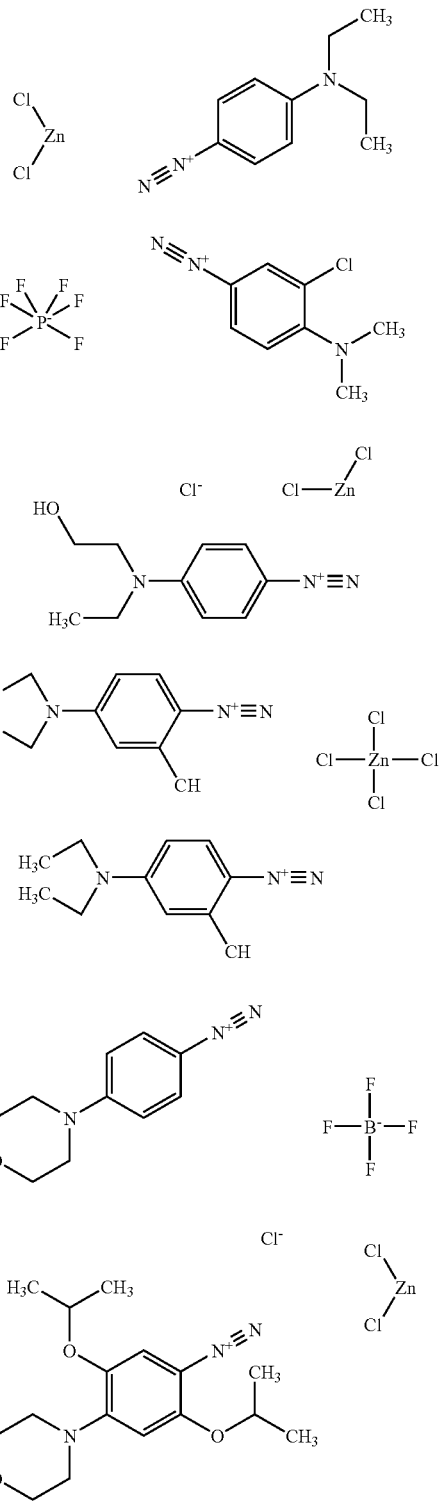

It could even be envisaged to produce them oneself from the corresponding aromatic amines (XIV) (see, by way of example, Patent FR2123267):

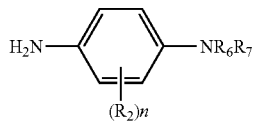

(XIV)

The aromatic amines (XIV) are themselves commercial or may be synthesized by taking inspiration from, for example, Patents FR2806299, FR2807650, DE3016216, DE3433594, EP911317.

Once the second step has been completed, an alkylation reaction is carried out, in a third step, in the presence of an inorganic base (MgO, $K_2CO_3$, $Na_2CO_3$, etc.).

The alkylating agent $R_1X$ and the solvent used have been described during a preceding synthesis variant and reference may be made thereto.

Another subject of the present invention is constituted by a composition comprising, as direct dye, in a medium suitable for dyeing keratin fibres, at least one compound of formula (I) and/or (II), or addition salts thereof with an acid.

The concentration of compound of formula (I) and/or (II) or of each of the compounds of formula (I) and/or (II) may vary between 0.001 and 20% by weight relative to the total weight of the dyeing composition, more particularly between 0.01 to 10% by weight, and preferably between 0.05 and 5% by weight.

The composition according to the invention may also comprise an oxidation base. This oxidation base may be chosen from the oxidation bases conventionally used in oxidation dyeing, for example para-phenylenediamines, bis-phenylalkylenediamines, para-aminophenols, orthoaminophenols and heterocyclic bases.

Among the para-phenylenediamines, mention may more particularly be made, by way of example, of: para-phenylenediamine, para-toluylenediamine, 2-chloro-para -phenylenediamine, 2,3-dimethyl-para-phenylenediamine, 2,6-dimethyl-para-phenylene -diamine, 2,6-diethyl-para-phenylenediamine, 2,5-dimethyl-para-phenylenediamine, N,N -dimethyl-para-phenylenediamine, N,N-diethyl-para-phenylenediamine, N,N-dipropyl-para -phenylenediamine, 4-amino-N,N-diethyl-3-methylaniline, N,N-bis-(β-hydroxyethyl) -para -phenylenediamine, 4-N,N-bis-(β-hydroxyethyl) amino-2-methylaniline, 4-N,N -bis-(β-hydroxy -ethyl) amino-2-chloroaniline, 2-β-hydroxyethyl-para-phenylenediamine, 2-fluoro-para -phenylenediamine, 2-isopropyl-para-phenylenediamine, N-(β-hydroxypropyl)-para -phenylenediamine, 2-hydroxymethyl-para-phenylenediamine, N,N-dimethyl-3-methyl-para -phenylenediamine, N,N-(ethyl,β-hydroxyethyl)-para-phenylenediamine, N-(β, γ-dihydroxy -propyl)-para-phenylenediamine, N-(4'-aminophenyl)-para-phenylenediamine, N-phenyl-para -phenylenediamine, 2-β-hydroxyethyloxy-para-phenylenediamine, 2-β-acetylaminoethyloxy, -para-phenylenediamine, N-(β-methoxyethyl)-para-phenylenediamine, 4-aminophenyl -pyrrolidine, 2-thienyl-para-phenylenediamine, 2-β-hydroxyethylamino-5-aminotoluene and addition salts thereof with an acid.

Among the para-phenylenediamines mentioned above, para-phenylenediamine, para -toluylenediamine, 2-isopropyl-para-phenylenediamine, 2-β-hydroxyethyl-para -phenylene -diamine, 2-β-hydroxyethyloxy-para-phenylenediamine, 2,6-dimethyl-para -phenylenediamine, 2,6-diethyl-para-phenylenediamine, 2,3-dimethyl-para-phenylenediamine, N,N-bis-(β-hydroxyethyl)-para-phenylenediamine, 2-chloro-para-phenylenediamine, 2-β- acetylamino-ethyloxy-para-phenylenediamine, and addition salts thereof with an acid are particularly preferred.

Among the bis-phenylalkylenediamines, mention may be made, by way of example, of: N,N'-bis-(β-hydroxyethyl)-N,N'-bis(4'-aminophenyl)-1,3-diaminopropanol, N,N'-bis(β-hydroxy-ethyl)-N,N'-bis(4'-aminophenyl)ethylenediamine, N,N'-bis(4-aminophenyl)tetramethylene-diamine, N,N'-bis(β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino,3'-methylphenyl)ethylenediamine, 1,8-bis(2,5-diaminophenoxy)-3,6-dioxaoctane, and addition salts thereof with an acid.

Among the para-aminophenols, mention may be made, by way of example, of: para-aminophenol, 4-amino-3-methylphenol, 4-amino-3-fluorophenol, 4-amino-3-hydroxymethyl-phenol, 4-amino-2-methylphenol, 4-amino-2-hydroxymethylphenol, 4-amino-2-methoxy-methylphenol, 4-amino-2-aminomethylphenol, 4-amino-2-(β-hydroxyethylaminomethyl)-phenol, 4-amino-2-fluorophenol, and addition salts thereof with an acid.

Among the ortho-aminophenols, mention may be made, by way of example, of: 2-aminophenol, 2-amino-5-methylphenol, 2-amino-6-methylphenol, 5-acetamido-2-aminophenol, and addition salts thereof with an acid.

Among the heterocyclic bases, mention may be made, by way of example, of: pyridine derivatives, pyrimidine derivatives and pyrazole derivatives.

Among the pyridine derivatives, mention may be made of the compounds described, for example, in Patents GB 1 026 978 and GB 1 153 196, such as 2,5-diaminopyridine, 2-(4-methoxyphenyl)amino-3-aminopyridine, 2,3-diamino-6-methoxypyridine, 2-(β-methoxyethyl)-amino-3-amino-6-methoxypyridine, 3,4-diaminopyridine, and addition salts thereof with an acid.

Among the pyrimidine derivatives, mention may be made of the compounds described, for example, in Patents DE 2 359 399; JP 88-169 571; JP 05 163 124; EP 0 770 375 or Patent Application WO 96/15765, such as 2,4,5,6-tetraminopyrimidine, 4-hydroxy-2,5,6-triaminopyrimidine, 2-hydroxy-4,5,6-triaminopyrimidine, 2,4-dihydroxy-5,6-diaminopyrimidine, 2,5,6-triaminopyrimidine, and pyrazolopyrimidine derivatives such as those mentioned in Patent Application FR-A-2 750 048 and among which mention may be made of: pyrazolo-[1,5-a]-pyrimidine-3,7-diamine; 2,5-dimethylpyrazolo-[1,5-a]-pyrimidine-3,7-diamine; pyrazolo-[1,5-a]-pyrimidine-3,5-diamine; 2,7-dimethylpyrazolo-[1,5-a]-pyrimidine-3,5-diamine; 3-aminopyrazolo-[1,5-a]-pyrimidin-7-ol; 3-aminopyrazolo-[1,5-a]-pyrimidin-5-ol; 2-(3-amino-pyrazolo-[1,5-a]-pyrimidin-7-ylamino)ethanol, 2-(7-aminopyrazolo-[1,5-a]-pyrimidin-3-ylamino)ethanol, 2-[(3-aminopyrazolo[1,5-a]pyrimidin-7-yl)-(2-hydroxyethyl)amino]ethanol, 2-[(7-aminopyrazolo[1,5-a]pyrimidin-3-yl)-(2-hydroxyethyl)amino]ethanol, 5,6-dimethylpyrazolo-[1,5-a]-pyrimidine-3,7-diamine, 2,6-dimethylpyrazolo-[1,5-a]-pyrimidine-3,7-diamine, 2,5,N7, N7-tetramethylpyrazolo-[1,5-a]-pyrimidine-3,7-diamine, 3-amino-5-methyl-7-imidazolylpropylaminopyrazolo-[1,5-a]-pyrimidine and addition salts thereof with an acid and tautomeric forms thereof, when a tautomeric equilibrium exists.

Among the pyrazole derivatives, mention may be made of the compounds described in Patents DE 3 843 892, DE 4 133 957 and Patent Applications WO 94/08969, WO 94/08970, FR-A-2 733 749 and DE 195 43 988 such as 4,5-diamino-1-methylpyrazole, 4,5-diamino-1-(β-hydroxyethyl)pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triaminopyrazole, 3,5-diamino-1-methyl-4-methylaminopyrazole, 3,5-diamino-4-(β-hydroxyethyl)amino-1-methylpyrazole, and addition salts thereof with an acid.

The composition according to the invention may contain one or more coupling agents conventionally used for dyeing keratin fibres. Among these coupling agents, mention may especially be made of meta-phenylenediamines, meta-aminophenols, meta-diphenols, naphthalene coupling agents and heterocyclic coupling agents.

By way of example, mention may be made of: 2-methyl-5-aminophenol, 5-N-(β-hydroxyethyl)amino-2-methylphenol, 6-chloro-2-methyl-5-aminophenol, 3-aminophenol, 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxy-benzene, 1,3-diaminobenzene, 1,3-bis(2,4-diaminophenoxy)propane, 3-ureidoaniline, 3-ureido-1-dimethylaminobenzene, sesamol, 1-β-hydroxyethylamino-3,4-methylenedioxy-benzene, α-naphthol, 2-methyl-1-naphthol, 6-hydroxyindole, 4-hydroxyindole, 4-hydroxy-N-methylindole, 2-amino-3-hydroxypyridine, 6-hydroxybenzomorpholine-3,5-diamino-2,6-dimethoxypyridine, 1-N-(β-hydroxyethyl)amino-3,4-methylenedioxybenzene, 2,6-bis(β-hydroxyethylamino)toluene and addition salts thereof with an acid.

In the composition of the present invention, the coupling agent(s) is (are) generally present in an amount between 0.001 and 10% by weight of the total weight of the dyeing composition and more preferably from 0.005 to 6% by weight. The oxidation base(s) is (are) present in an amount preferably between 0.001 and 10% by weight of the total weight of the dyeing composition and more preferably from 0.005 to 6% by weight.

Generally, the addition salts with an acid that can be used within the context of the dyeing compositions of the invention for the oxidation bases and coupling agents are chosen, in particular, from chlorohydrates, bromohydrates, sulphates, citrates, succinates, tartrates, lactates, tosylates, benzenesulphonates, phosphates and acetates.

The composition according to the invention may optionally comprise at least one additional direct dye different from the compounds of formula (I) and/or (II). This may be chosen from cationic or non-ionic species.

By way of non-limiting examples, mention may be made of: nitrobenzene dyes, azo, azomethine, methine, tetraazapentamethine, anthraquinone, naphthoquinone, benzoquinone, phenothiazine, indigoid, xanthene, phenanthridine and phthalocyanin dyes and those derived from triarylmethane, and natural dyes, alone or as mixtures.

It may, for example be chosen from the following red or orange nitrobenzene dyes:
  1-hydroxy-3-nitro-4-N-(β-hydroxypropyl)aminobenzene;
  N-(β-hydroxyethyl)amino-3-nitro-4-aminobenzene;
  1-amino-3-methyl-4-N-(β-hydroxyethyl)amino-6-nitrobenzene;

1-hydroxy-3-nitro-4-N-(β-hydroxyethyl)aminobenzene;
1,4-diamino-2-nitrobenzene;
1-amino-2-nitro-4-methylaminobenzene;
N-(β-hydroxyethyl)-2-nitro-para-phenylenediamine;
1-amino-2-nitro-4-(β-hydroxyethyl)amino-5-chlorobenzene;
2-nitro-4-amino-diphenylamine;
1-amino-3-nitro-6-hydroxybenzene;
1-(β-aminoethyl)amino-2-nitro-4-(β-hydroxyethyloxy) benzene;
1-(β, γ-dihydroxypropyl)oxy-3-nitro-4-(β-hydroxyethyl) aminobenzene;
1-hydroxy-3-nitro-4-aminobenzene;
1-hydroxy-2-amino-4,6-dinitrobenzene;
1-methoxy-3-nitro-4-(β-hydroxyethyl)aminobenzene;
2-nitro-4'-hydroxydiphenylamine; and
1-amino-2-nitro-4-hydroxy-5-methylbenzene.

The additional direct dye may also be chosen from yellow and yellowy-green nitrobenzene direct dyes, mention may, for example, be made of the compounds chosen from:
1-β-hydroxyethyloxy-3-methylamino-4-nitrobenzene;
1-methylamino-2-nitro-5-(β,γ-dihydroxypropyl)oxy benzene;
1-(β-hydroxyethyl)amino-2-methoxy-4-nitrobenzene;
1-(β-aminoethyl)amino-2-nitro-5-methoxybenzene;
1,3-di(β-hydroxyethyl)amino-4-nitro-6-chlorobenzene;
1-amino-2-nitro-6-methylbenzene;
1-(β-hydroxyethyl)amino-2-hydroxy-4-nitrobenzene;
N-(β-hydroxyethyl)-2-nitro-4-trifluoromethylaniline;
4-(β-hydroxyethyl)amino-3-nitrobenzenesulphonic acid;
4-ethylamino-3-nitrobenzoic acid;
4-(β-hydroxyethyl)amino-3-nitrochlorobenzene;
4-(β-hydroxyethyl)amino-3-nitromethylbenzene;
4-(β,γ-dihydroxypropyl)amino-3-nitrotrifluoromethylbenzene;
1-(β-ureidoethyl)amino-4-nitrobenzene;
1,3-diamino-4-nitrobenzene;
1-hydroxy-2-amino-5-nitrobenzene;
1-amino-2-[tris(hydroxymethyl)methyl]amino-5-nitrobenzene;
1-(β-hydroxyethyl)amino-2-nitrobenzene; and
4-(β-hydroxyethyl)amino-3-nitrobenzamide.

Mention may also be made of blue or violet nitrobenzene direct dyes, such as, for example:
1-(β-hydroxyethyl)amino-4-N,N-bis(β-hydroxyethyl) amino-2-nitrobenzene;
1-(γ-hydroxypropyl)amino-4-N,N-bis(β-hydroxyethyl) amino-2-nitrobenzene;
1-(β-hydroxyethyl)amino-4-(N-methyl, N-β-hydroxyethyl)amino-2-nitrobenzene;
1-(β-hydroxyethyl)amino-4-(N-ethyl, N-β-hydroxyethyl) amino-2-nitrobenzene;
1-(β,γ-dihydroxypropyl)amino-4-(N-ethyl, N-β-hydroxyethyl)amino-2-nitrobenzene; and
2-nitro-para-phenylenediamines of the following formula:

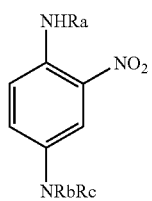

in which:
Rb represents a $C_1$-$C_4$ alkyl radical, or a β-hydroxyethyl or β-hydroxypropyl or γ-hydroxypropyl radical; and
Ra and Rc, which may be identical or different, represent a β-hydroxyethyl, β-hydroxypropyl, γ-hydroxypropyl, or β,γ-dihydroxypropyl radical, at least one of the Rb, Rc or Ra radicals representing a γ-hydroxypropyl radical and Rb and Rc not being able to simultaneously denote a β-hydroxyethyl radical when Rb is a γ-hydroxypropyl radical, such as those described in French Patent FR 2 692 572.

Among the azo direct dyes that can be used according to the invention, mention may be made of the cationic azo dyes described in Patent Applications WO 95/15144, WO 95/01772 and EP 714954.

Among these compounds, mention may most particularly be made of the following dyes:
1,3-dimethyl-2-[[4-(dimethylamino)phenyl]azo]-1H-imidazolium chloride;
1,3-dimethyl-2-[(4-aminophenyl)azo]-1H-imidazolium chloride; and
1-methyl-4-[(methylphenylhydrazono)methyl]pyridinium methylsulphate.

Among the azo direct dyes, mention may also be made of the following dyes, described in the COLOUR INDEX INTERNATIONAL, 3rd edition:
Disperse Red 17;
Acid Yellow 9;
Acid Black 1;
Basic Red 22;
Basic Red 76;
Basic Yellow 57;
Basic Brown 16;
Acid Yellow 36;
Acid Orange 7;
Acid Red 33;
Acid Red 35;
Basic Brown 17;
Acid Yellow 23;
Acid Orange 24; and
Disperse Black 9.

Mention may also be made of 1-(4'-aminodiphenylazo)-2-methyl-4-bis(β-hydroxyethyl) -aminobenzene and 4-hydroxy-3-(2-methoxyphenylazo)-1-naphthalenesulphonic acid.

Among the quinone direct dyes, mention may be made of the following dyes:
Disperse Red 15;
Solvent Violet 13;
Acid Violet 43;
Disperse Violet 1;
Disperse Violet 4;
Disperse Blue 1;
Disperse Violet 8;
Disperse Blue 3;
Disperse Red 11;
Acid Blue 62;
Disperse Blue 7;
Basic Blue 22;
Disperse Violet 15;
Basic Blue 99;
and also the following compounds:
1-N-methylmorpholiniumpropylamino-4-hydroxyanthraquinone;
1-aminopropylamino-4-methylaminoanthraquinone;
1-aminopropylaminoanthraquinone;
5-β-hydroxyethyl-1,4-diaminoanthraquinone;

2-aminoethylaminoanthraquinone; and 1,4-bis(β,γ-dihydroxypropylamino)anthraquinone.

Among the azine dyes, mention may be made of the following compounds:

Basic Blue 17; and

Basic Red 2.

Among the triarylmethane dyes that can be used according to the invention, mention may be made of the following compounds:

Basic Green 1;

Acid blue 9;

Basic Violet 3;

Basic Violet 14;

Basic Blue 7;

Acid Violet 49;

Basic Blue 26; and

Acid Blue 7.

Among the indoamine dyes that can be used according to the invention, mention may be made of the following compounds:

2-β-hydroxyethylamino-5-[bis(β-4'-hydroxyethyl)amino] anilino -1,4-benzoquinone;

2-β-hydroxyethylamino-5-(2'-methoxy-4'-amino)anilino -1,4-benzoquinone;

3-N-(2'-chloro-4'-hydroxy)phenylacetylamino-6-methoxy-1,4-benzoquinoneimine;

3-N-(3'-chloro-4'-methylamino)phenylureido-6-methyl-1,4-benzoquinoneimine;

3-[4'-N-(ethyl,carbamylmethyl)amino]phenylureido-6-methyl-1,4-benzoquinoneimine.

Among the tetraazapentamethine-type dyes that can be used according to the invention, mention may be made of the following compounds: 2-((E)-{(E)-[(1,3-dimethyl-1,3-dihydro-2H-imidazol-2-ylidene)hydrazono]methyl}diazenyl)-1, 3-dimethyl -1H-imidazol-3-ium chloride, 2-{(E)-[(1Z)-N-(1, 3-dimethyl-1,3-dihydro-2H-imidazol-2-ylidene) ethanehydrazonoyl]diazenyl}-1,3-dimethyl-1H-imidazol-3-ium chloride, 4-methoxy-2-((E)-{(1E)-1-[(2E)-(4-methoxy-1-methylpyridin-2(1H)-ylidene)hydrazono]ethyl}diazenyl)-1-methylpyridinium chloride, 1-methyl-2-((E)-{(1E)-1-[(2E)-(1-methylpyridin-2(1H)-ylidene]hydrazono}methyl) -diazenyl)pyridinium chloride, 1-(2-hydroxyethyl)-2-[(E)-((1E)-1-{(2E)-[1-(2-hydroxyethyl) -pyridin-2(1H)-ylidene] hydrazono}ethyl)diazenyl]pyridinium chloride, 1-methyl-2-((E)-{(E)       -[(2Z)-(1-methylpyridin-2(1H)-ylidene) hydrazono]methyl}diazenyl)pyridinium chloride, 1-(2-hydroxyethyl)-2-[(E)-((E)-{(2E)-[1-(2-hydroxyethyl) pyridin-2(1H)-ylidene]hydrazono}methyl)      -diazenyl] pyridinium acetate.

Among the natural direct dyes that can be used according to the invention, mention may be made of lawsone, juglone, alizarin, purpurin, carminic acid, kermesic acid, purpurogallin, protocatechaldehyde, indigo, isatin, curcumin, spinulosin and apigenidin. It is also possible to use extracts or decoctions containing these naturel dyes, especially henna-based poultices or extracts.

When they are present, the content of additional direct dye(s) in the composition generally varies from 0.001 to 20% by weight relative to the weight of the composition, and preferably from 0.01 to 10% by weight relative to the weight of the composition.

The medium suitable for dyeing, also known as a dye support, is generally constituted of water or of a mixture of water and at least one organic solvent to dissolve the compounds that might not be sufficiently water-soluble.

More particularly, the organic solvents are chosen from linear or branched, preferably saturated monoalcohols or diols comprising 2 to 10 carbon atoms such as ethyl alcohol, isopropyl alcohol, hexylene glycol (2-methyl-2,4-pentanediol), neopentyl glycol and 3-methyl-1,5-pentanediol; aromatic alcohols such as benzyl alcohol and phenyl ethyl alcohol; glycols or glycol ethers such as, for example, ethylene glycol monomethyl, monoethyl and monobutyl ethers, propylene glycol or ethers thereof such as, for example, propylene glycol monomethyl ether, butylene glycol, dipropylene glycol; and also diethylene glycol alkyl ethers, especially the $C_1$-$C_4$ alkyl ethers such as, for example, diethylene glycol monoethyl ether or monobutyl ether, alone, or as mixtures.

The customary solvents described above, when they are presents, usually represent from 1 to 40% by weight, more preferably from 5 to 30% by weight, relative to the total weight of the composition.

The dyeing composition according to the invention may also contain various adjuvants conventionally used in hair-dyeing compositions, such as anionic, cationic, non-ionic, amphoteric or zwitterionic surfactants, or mixtures thereof, anionic, cationic, non-ionic, amphoteric or zwitterionic polymers, or mixtures thereof, mineral or organic thickeners, and in particular anionic, cationic, non-ionic and amphoteric polymeric associative thickeners, antioxidants, penetrating agents, sequestering agents, fragrances, buffers, dispersants, conditioning agents such as, for example, volatile or non-volatile, modified or unmodified silicones, film-forming agents, ceramides, preservatives and opacifiers.

These adjuvants above are generally present in an amount between, for each of them, 0.01 and 20% by weight relative to the weight of the composition.

Of course, a person skilled in the art will be sure to choose this or these optional complementary compounds so that the advantageous properties intrinsically linked to the oxidation-dyeing composition according to the invention are not, or are not substantially, impaired by the envisaged addition or additions.

The pH of the dyeing composition according to the invention is generally between around 3 and 12, and preferably between around 5 and 11. It may be adjusted to the desired value using acidifying or basifying agents commonly used in dyeing keratin fibers or else using conventional buffer systems.

Among the acidifying agents, mention may be made, by way of example, of mineral or organic acids such as hydrochloric acid, orthophosphoric acid, sulphuric acid, carboxylic acids such as acetic acid, tartaric acid, citric acid, lactic acid, and sulphonic acids.

Among the basifying agents, mention may be made, by way of example, of ammonia, alkali metal carbonates, alkanolamines such as mono-, di- and triethanolamines and also derivatives thereof, sodium or potassium hydroxides and compounds of the following formula:

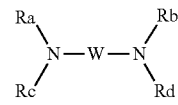

in which W is a propylene residue optionally substituted by a hydroxyl group or a $C_1$-$C_4$ alkyl radical; $R_a$, $R_b$, $R_c$ and $R_d$, which may be identical or different, represent a hydrogen atom, a $C_1$-$C_4$ alkyl radical or a hydroxy($C_1$-$C_4$)alkyl radical.

The dyeing composition according to the invention may be in various forms, such as in the form of liquids, creams, gels, pastes or any other appropriate form for carrying out dyeing of keratin fibers, and especially of human hair.

The composition according to the invention may additionally comprise at least one oxidizer. In this case it is referred to as a ready-to-use composition.

The expression "ready-to-use composition" is understood to mean, in the sense of the present invention, a composition intended to be applied immediately to the keratin fibres, that is to say that it can be stored as is before use or result from the extemporaneous mixing of two or more compositions.

According to this variant, the composition of the invention comprises at least one oxidizer in order to obtain, in particular, a lightening of the fibres. The oxidizers conventionally used for dyeing keratin fibres are, for example, hydrogen peroxide, urea peroxide, alkali metal bromates, persalts such as perborates and persulphates, peracids and oxidase enzymes, among which mention may be made of peroxidases, 2-electron oxidoreductases such as uricases and 4-electron oxygenases such as laccases. According to one particular embodiment the composition contains an oxidizer of peroxide type and/or an oxidizer of persalt type, for example a mixture of hydrogen peroxide and persulphates, the hydrogen peroxide alone or the persulphate alone.

The oxidizer content is generally between 1 and 40% by weight, relative to the weight of the ready-to-use composition, preferably between 1 and 20% by weight relative to the weight of the ready-to-use composition.

Generally, the oxidizing composition used is an aqueous composition and may be in the form of a solution or else of an emulsion.

Usually, the oxidizer-free composition is mixed with around 0.5 to 10 equivalents by weight of the oxidizing composition.

It should be noted that the pH of the ready-to-use composition is more particularly between 4 and 12, preferably between 7 and 11.5.

The pH of the composition may be adjusted by means of an acidifying or basifying agent, especially chosen from those mentioned previously, in the context of the description according to the invention.

Another subject of the invention is a dyeing method that comprises the application of a dyeing composition according to the invention to dry or wet keratin fibres.

The application, to the fibres, of the dyeing composition comprising the compound or compounds of formula (I) and/or (II) or addition salts thereof with an acid, optionally at least one oxidation base optionally combined with at least one coupling agent, and optionally at least one additional direct dye, may be carried out in the presence of an oxidizer.

This oxidizer may be added to the composition comprising the compound or compounds of formula (I) and/or (II) and also the optional oxidation bases, coupling agents and/or additional direct dyes, either at the moment of use, or directly to the keratin fibre.

The oxidizing composition may also contain various adjuvants conventionally used in hair-dyeing compositions and such as defined previously.

The pH of the oxidizing composition containing the oxidizer is such that after mixing with the dyeing composition, the pH of the resulting composition applied to the keratin fibres varies preferably between 4 and 12 approximately, and even more preferably between 7 and 11.5. It may be adjusted to the desired value by means of acidifying or basifying agents, customarily used in dyeing keratin fibres and such as defined previously.

The composition that is finally applied to the keratin fibres may be in various forms, such as in the form of liquids, creams, gels or any other appropriate form for carrying out dyeing of keratin fibers, and especially of human hair.

According to one particular embodiment, the composition according to the invention is free of oxidation base and coupling agent.

The composition applied may optionally comprise at least one oxidizer.

The composition is therefore applied to dry or wet keratin fibres, then left for a sufficient leave-in time to obtain the desired colouring.

Whichever variant is used (with or without oxidizer), the leave-in time is generally between a few seconds and an hour, preferably between 3 and 30 minutes.

The temperature at which the composition is left to act is generally between 15 and 220° C., more particularly between 15 and 80° C., preferably between 15 and 40° C.

At the end of the leave-in time, the composition is removed by rinsing with water, optionally followed by washing with shampoo, then optionally by drying.

Another subject of the invention is a dyeing multicompartment device or "kit" in which a first compartment contains the dyeing composition of the invention and a second compartment contains the oxidizing composition. This device may be equipped with a means that enables the desired mixture to be delivered to the hair, such as the devices described in Patent FR-2 586 913.

The following examples are used to illustrate the invention without however being limiting.

EXAMPLE

Example 1

Synthesis of the 2-{(E)-[{4-[(4-methoxyphenyl)amino]phenyl}(methyl)hydrazono]-methyl}-1-methylpyridinium methosulphate salt

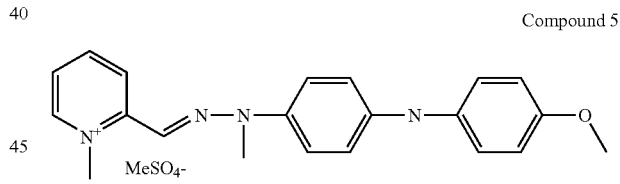

Compound 5

Step 1:

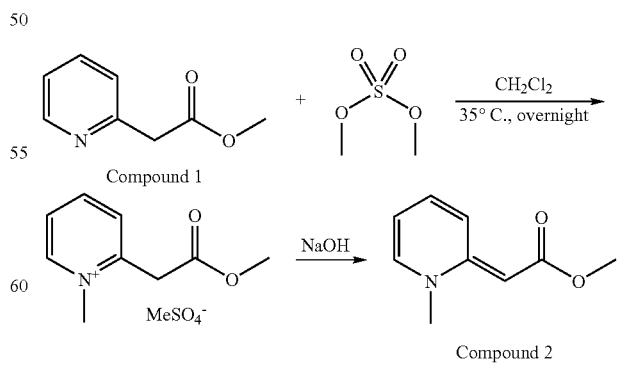

Compound 1 is commercial and compound 2 may also be obtained by taking inspiration from the procedure described in J.A.C.S., 126(48), 15777-15783, 2004.

In a 100 ml round-bottomed flask topped with a condenser, compound 1 (36 g; 1 eq.) dissolved in 25 ml of dichloromethane was stirred at ambient temperature. Next, dimethylsulphate (36 g; 1.2 eq.) was added. The reaction medium was heated at 35° C. overnight.

After reacting, the dichloromethane was removed under vacuum, then the reaction medium was poured over a mixture composed of water, ice and sodium hydroxide (pH 11-12). A yellow product precipitated. This was filtered through a frit, washed several times with water, then dried under vacuum. 32.6 g of a yellow powder corresponding to compound 2 were obtained.

The NMR spectra and the mass spectra conformed to the expected product 2.

Step 2:

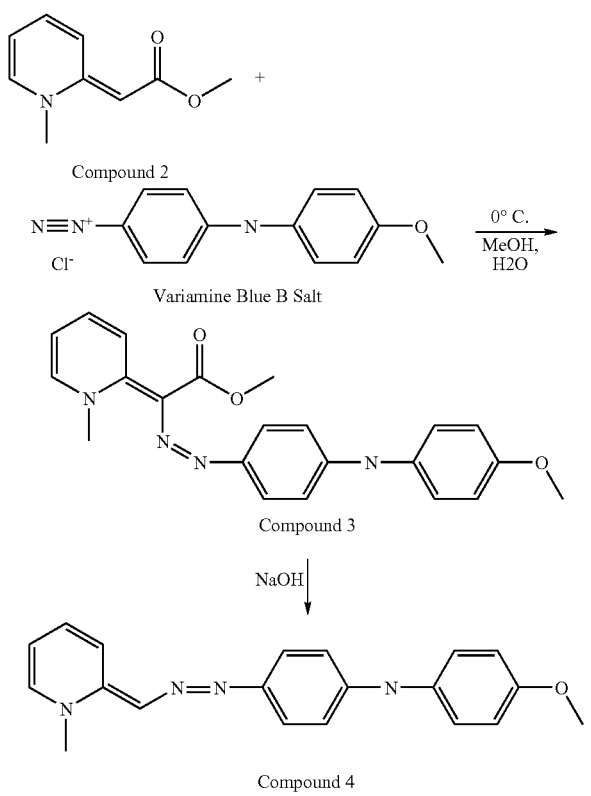

Compound 2 (4 g), in solution in a water/methanol (50 ml/50 ml) mixture, was introduced into a three-necked flask equipped with a thermometer and a pH meter. The solution was cooled to 5° C. using a bath of iced water. Variamine Blue (6.3 g, commercial product), dissolved in 50 ml of methanol was added dropwise at 5° C. to the preceding reaction mixture.

The whole mixture was stirred for 4 h while subsequently allowing the temperature of the reaction medium to return to ambient temperature.

After reacting, the reaction medium was poured over a mixture of iced water and sodium hydroxide (pH 12-13); a precipitate appeared. An analysis carried out on the precipitate indicated that it was compound 3. This basic heterogeneous solution was left stirring for 2 days at ambient temperature.

A solid having a different colour to compound 3 was obtained. This solid was filtered and then dried under vacuum.

The product obtained was purified on a silica column (eluent: $CH_2Cl_2$/MeOH/AcOH 8/2/1).

417 mg of a dark violet powder corresponding to the compound 4 were obtained.

The NMR spectra and the mass spectra conformed to the expected product 4.

Step 3:

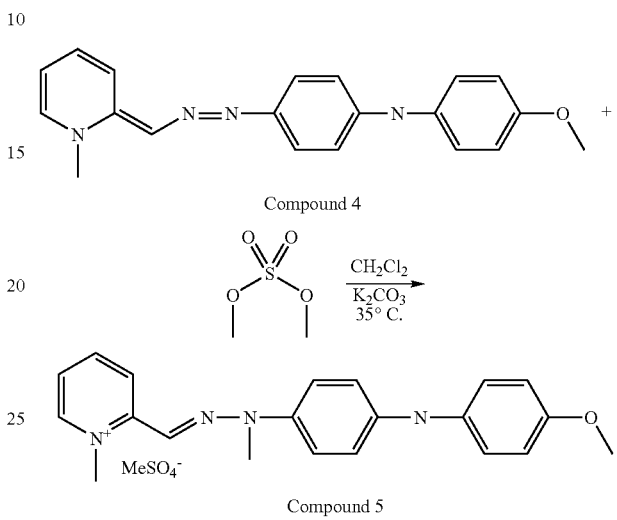

In a round-bottomed flask topped with a bubbler, compound 4 (200 mg) dissolved in 5 ml of dichloromethane was stirred at 35° C. and three spatula tip-fulls of $K_2CO_3$ were added.

Next, dimethylsulphate (0.082 g; 1.1 eq.) was introduced at 35° C. and the reaction medium was stirred overnight at 35° C.

After reacting, a product precipitated. It was filtered and reslurried in dichloromethane.

Compound 5 was obtained in the form of an orange powder (500 mg).

The NMR spectra and the mass spectra conformed to the expected product 5.

Example 2

Synthesis of the 2-((1Z)-2-methoxy-N-{4-[(4-methoxyphenyl)amino]phenyl}-N-methyl-2-oxoethanehydrazonoyl)-1-methylpyridinium methosulphate salt (6)

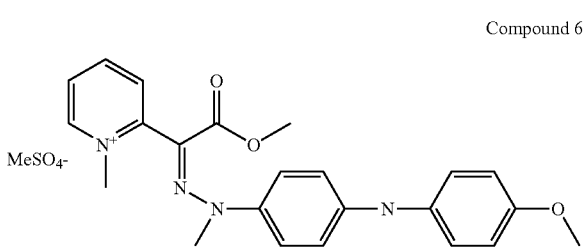

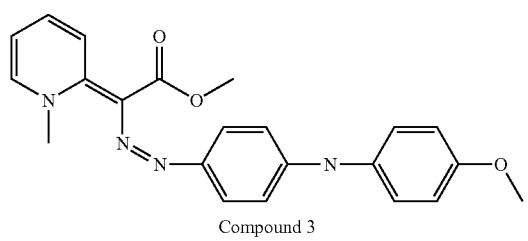

Compound 3

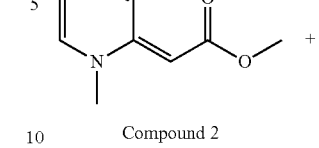

Compound 2

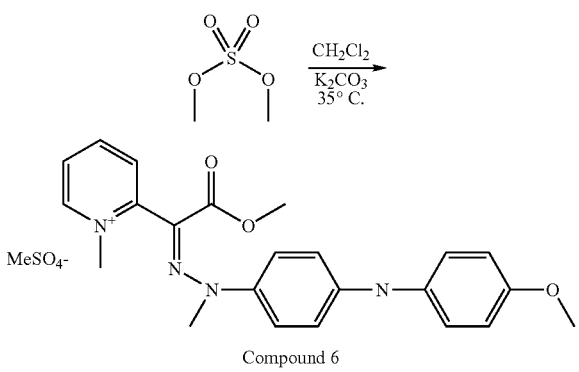

Compound 6

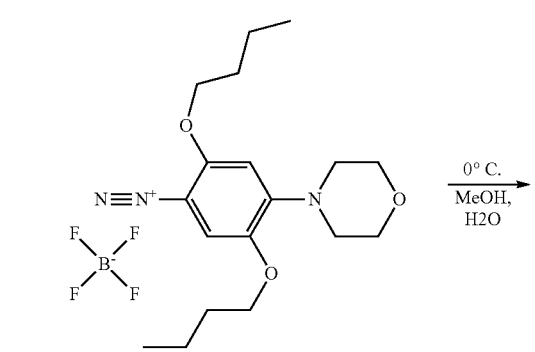

In a 10 ml round-bottomed flask topped with a bubbler, the previously obtained compound 3 (200 mg; 1 eq.) dissolved in 5 ml of dichloromethane was stirred at 35° C. Two spatula tip-fulls of K$_2$CO$_3$ were added.

Next, dimethylsulphate (0.082 g; 1.1 eq.) was introduced at 35° C. and the reaction medium was stirred overnight at 35° C. After reacting, the product was precipitated with 100 ml of diisopropyl ether.

It was filtered and taken back up in 20 ml of methanol, then the solvent was evaporated to dryness.

420 mg of a yellow-orange solid corresponding to compound 6 were obtained.

The NMR spectra and the mass spectra conformed to the expected product 6.

Example 3

Synthesis of the 2-{(E)-[(2,5-dibutoxy-4-morpholin-4-ylphenyl)(methyl)hydrazono]-methyl}-1-methylpyridinium methosulphate salt (9)

Compound 9

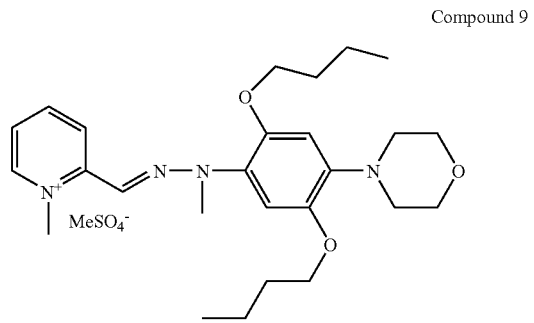

Step 1:

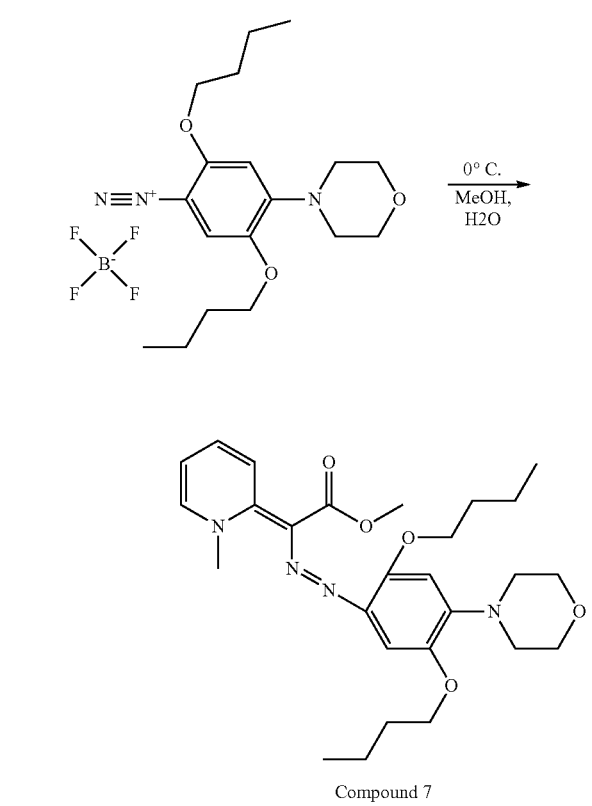

Compound 7

Compound 2 (0.8 g), in solution in a water/methanol (10 ml/15 ml) mixture, was introduced into a three-necked flask topped with a thermometer and a pH meter. The solution was cooled to 5° C. using a bath of iced water. 2,5-dibutoxy-4-(4-morpholinyl)benzenediazonium tetrafluoroborate (2.04 g, commercial product), dissolved in 10 ml of methanol was added dropwise to the preceding reaction mixture. The whole mixture was stirred for 3 h while allowing the temperature of the reaction medium to return to ambient temperature. After reacting, the reaction medium was poured over a mixture of iced water and sodium hydroxide (pH 12-13).

The aqueous phase obtained was then extracted with dichloromethane. The organic phase was dried over Na$_2$SO$_4$ then concentrated under vacuum. The product obtained was taken back up in diisopropyl ether, filtered, then dried under vacuum. A dark violet powder (1.73 g) corresponding to compound 7 was obtained.

The NMR spectra and the mass spectra conformed to the expected product 7.

Step 2:

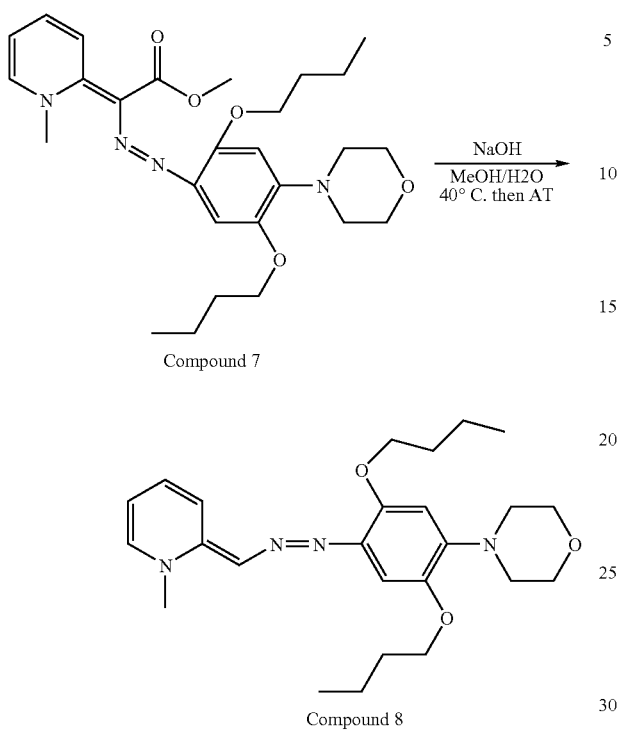

Compound 7 (1.5 g), in solution in 25 ml of methanol and 5 ml of water was introduced into a three-necked flask equipped with a pH meter.

Added to the preceding reaction medium was a concentrated aqueous solution of sodium hydroxide in order to attain a pH of 12-13.

It was left stirring at 40° C. for 3 hours then at ambient temperature overnight.

After reacting, the reaction medium was poured over 200 ml of iced water; a dark powder precipitated. This was filtered through a frit, then dried under vacuum. 350 mg of a dark violet powder corresponding to compound 8 were obtained.

The NMR spectra and the mass spectra conformed to the expected product 8.

Step 3:

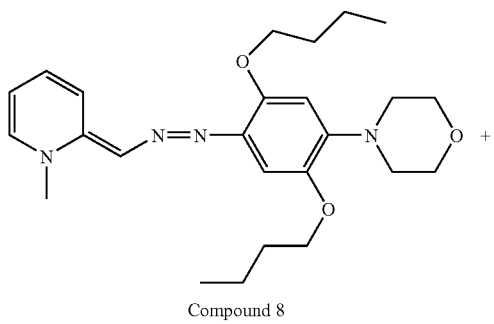 +

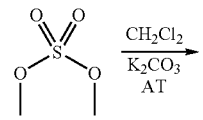

-continued

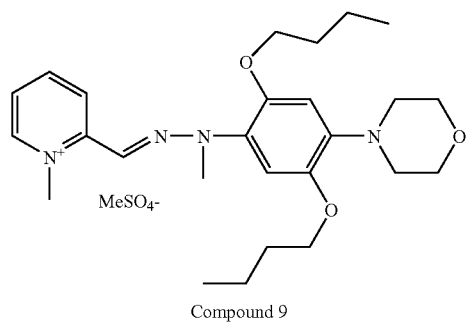

In a round-bottomed flask topped with a bubbler, the previously obtained compound 8 (306 mg) dissolved in 5 ml of dichloromethane was stirred at 35° C. Three spatula tip-fulls of $K_2CO_3$ were added to the preceding reaction medium.

Next, dimethylsulphate (0.1 g; 1.1 eq.) was introduced into the reaction medium and the latter was stirred overnight.

After reacting, the product was precipitated by adding 100 ml of ethyl acetate to the reaction medium, then filtered and finally dried under vacuum. 320 mg of a dark orange powder corresponding to compound 9 were obtained.

The NMR spectra and the mass spectra conformed to the expected product 9.

Example 4

Synthesis of the 2-{(E)-[[4-(diethylamino)phenyl](methyl)hydrazono]methyl}-1-methyl-pyridinium methosulphate salt (12)

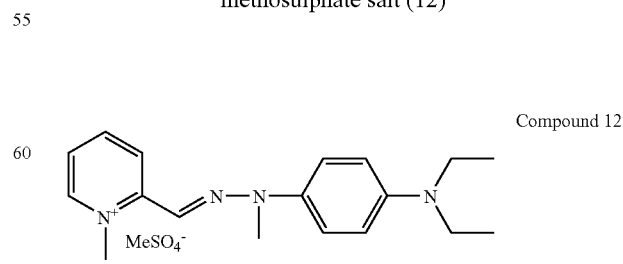

Step 1:

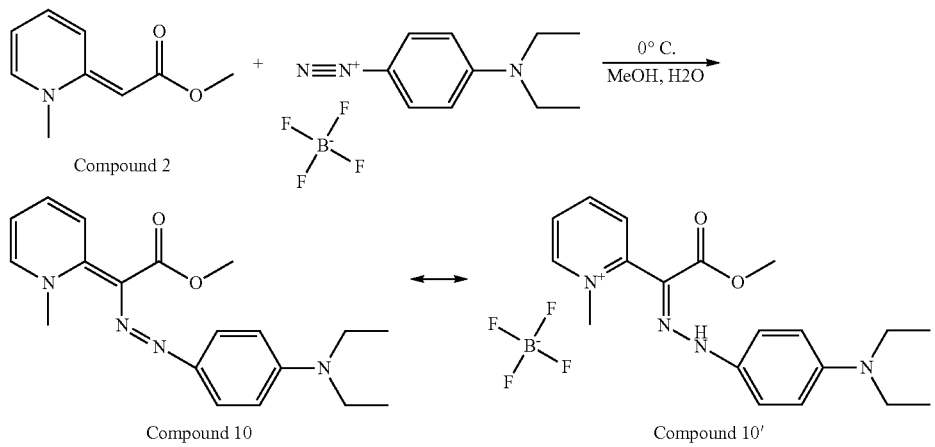

Compound 2 (1 g), in solution in a water/methanol (10 ml/15 ml) mixture, was introduced into a three-necked flask equipped with a thermometer and a pH meter. The solution was first cooled to 5° C. using a bath of iced water. 4-(diethylamino)-benzenediazonium tetrafluoroborate (1.6 g, commercial compound), dissolved in 10 ml of methanol and 10 ml of water, was first added dropwise to the preceding reaction mixture.

The reaction medium was stirred for 2 h while allowing its temperature to return to ambient temperature.

After reacting, the reaction medium was poured over a mixture composed of water, ice and sodium hydroxide (pH 12-13).

A solid precipitated. This solid was filtered and then dried under vacuum. A dark powder corresponding to the compound 10/10' was obtained (1.63 g). The NMR spectra and the mass spectra conformed to the expected product (mixture of forms 10 and 10').

Step 2:

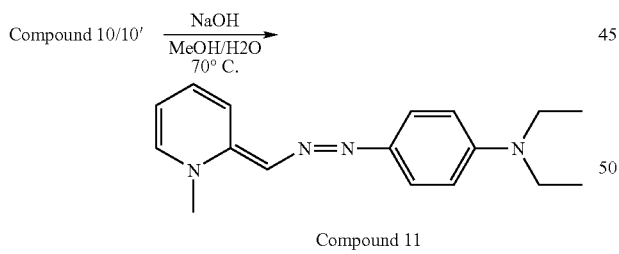

Compound 10/10' (750 mg), in solution in 12 ml of methanol and 2 ml of water was introduced at ambient temperature into a round-bottomed flask equipped with a bubbler. 4 ml of a concentrated aqueous solution of sodium hydroxide were added to the preceding reaction medium (pH 12-13). The reaction medium was stirred at 70° C. for 2 hours.

After reacting, the reaction medium was poured over 200 ml of iced water and the aqueous phase obtained was extracted with dichloromethane. The organic phase was dried over Na$_2$SO$_4$, filtered then concentrated under vacuum. A dark red powder corresponding to compound 11 was obtained (441 mg).

The NMR spectra and the mass spectra conformed to the expected product 11.

Step 3:

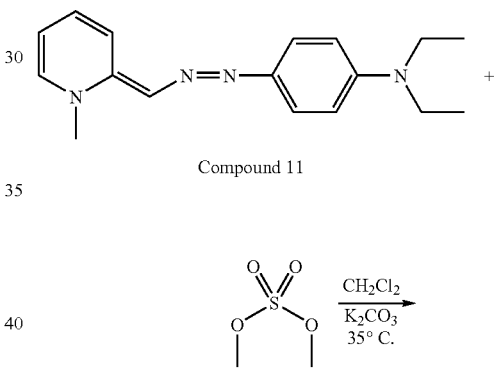

In a round-bottomed flask equipped with a bubbler, compound 11 (291 mg) dissolved in 5 ml of dichloromethane was stirred at 35° C. Three spatula tip-fulls of K$_2$CO$_3$ were added to the preceding reaction medium.

Next, dimethylsulphate (1.146 g; 1.1 eq.) was introduced at 35° C. and left stirring for 1 hour.

After reacting, the product was precipitated by adding 100 ml of ethyl acetate to the reaction medium obtained previously. A shiny dark red powder corresponding to compound 12 was obtained (191 mg).

The NMR spectra and the mass spectra conformed to the expected product 12.

Example 5

Synthesis of the 4-{(Z)-[{4-[(4-methoxyphenyl)amino]phenyl}(methyl)hydrazono]-methyl}-1-methylquinolinium methosulphate salt (17)

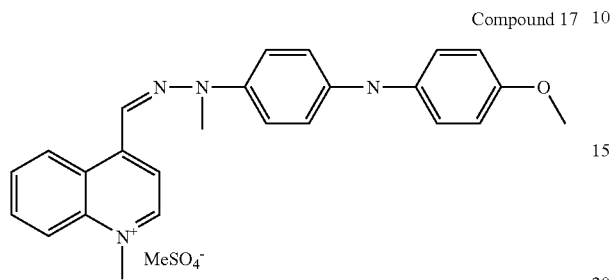

Compound 17

Step 1:

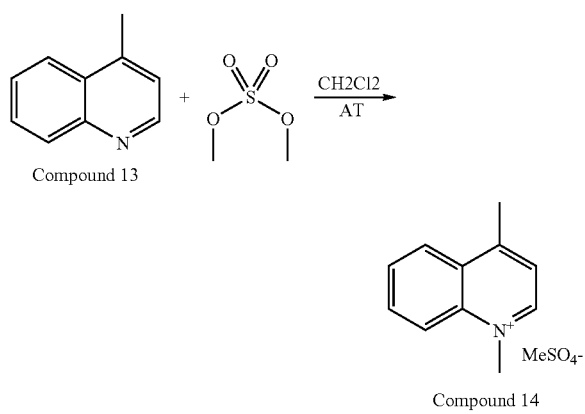

Compound 13 (10 g—commercial product) dissolved in 50 ml of dichloromethane was stirred in a round-bottomed flask equipped with a bubbler. Dimethylsulphate (8.91 g; 1 eq.) was then introduced into the preceding reaction medium.

The reaction medium was left stirring at ambient temperature overnight.

After reacting, the formation of a precipitate was observed. This was filtered and then dried under vacuum. A white powder corresponding to compound 14 (15 g) was obtained.

The NMR spectra and the mass spectra conformed to the expected product.

Step 2:

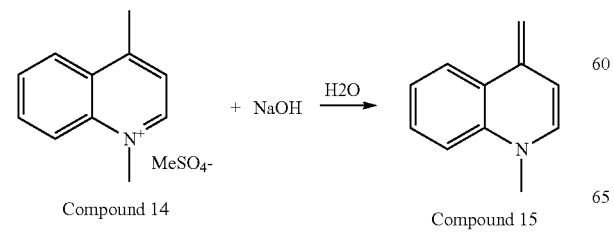

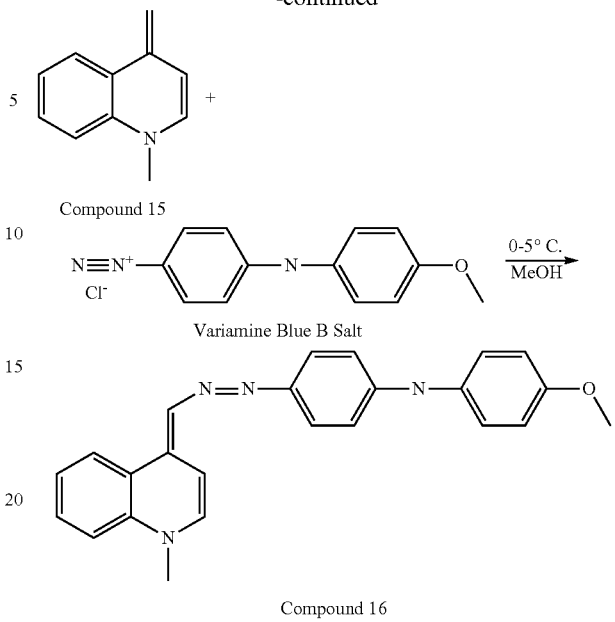

Compound 14 (3.1 g) in solution in 50 ml of iced water was introduced into an Erlenmeyer flask.

A 35% sodium hydroxide solution was added dropwise to the preceding reaction medium. A precipitate then appeared; this was filtered, then dried under vacuum. A pinkish powder corresponding to compound 15 was obtained.

In a beaker, 2 g of variamine blue was dissolved in 30 ml of methanol. The solution was cooled to 0-5° C. using a bath of iced water and a suspension of 1.81 g of compound 15 in 20 ml of methanol was added slowly.

The whole mixture was stirred for 2 h while allowing the temperature of the reaction medium to return to ambient temperature.

After reacting, the reaction medium was poured over a mixture constituted of water, ice and sodium hydroxide (pH 12-13). A precipitate appeared; this was filtered through a frit, then dried under vacuum.

2.46 g of a dark blue powder corresponding to compound 16 were obtained.

The NMR spectra and the mass spectra conformed to the expected product 16.

Step 3:

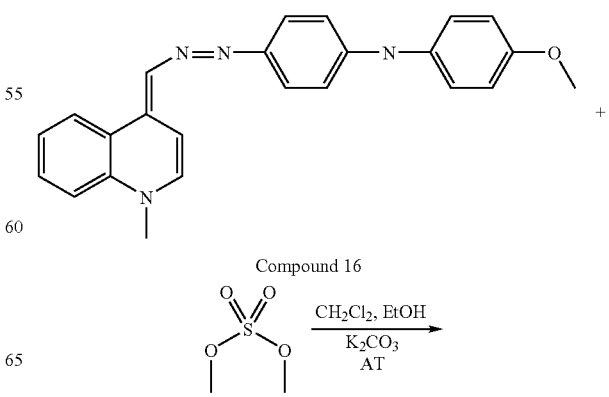

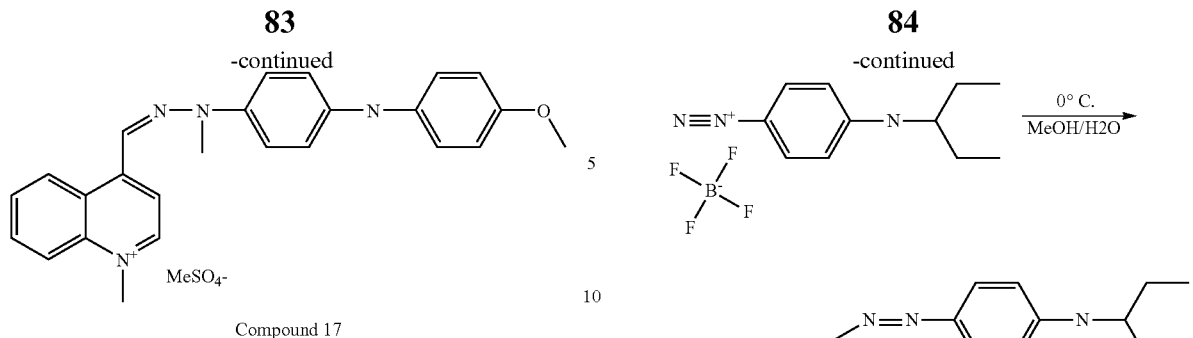

Compound 17

In a round-bottomed flask equipped with a bubbler, compound 16 (200 mg) dissolved in 10 ml of dichloromethane and 1 ml of ethanol was stirred at 35° C. Two spatula tip-fulls of K₂CO₃ were added to the preceding reaction medium.

Next, dimethylsulphate (0.0665 g; 1.1 eq.) was introduced into the reaction medium, which was left stirring for 3 hours.

After reacting, the product was precipitated by adding 300 ml of ethyl acetate to the reaction medium.

A dark blue powder corresponding to compound 17 was obtained (146 mg).

The NMR spectra and the mass spectra conformed to the expected product 17.

Example 6

Synthesis of the 4-{(Z)-[[4-(diethylamino)phenyl](methyl)hydrazono]methyl}1-methyl-quinolinium methosulphate salt (19)

Compound 19

Step 1:

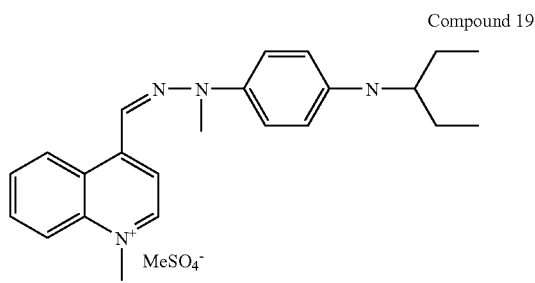

Compound 14   Compound 15

Compound 15

Compound 14 (5 g) in solution in 50 ml of iced water was introduced into an Erlenmeyer flask.

A 35% sodium hydroxide solution was added dropwise to the preceding reaction medium. A precipitate then appeared; this was filtered, then dried under vacuum. A pinkish powder corresponding to compound 15 was obtained.

In a beaker, 4-(diethylamino)benzenediazonium tetrafluoroborate (4.06 g—commercial product), dissolved in 40 ml of methanol and 10 ml of water, was cooled to 0° C. using a bath of iced water.

The pinkish compound 15 (2.92 g) obtained previously, in suspension in 30 ml of methanol, was added slowly thereto.

The whole mixture was stirred for 2 h while allowing the temperature of the reaction medium to return to ambient temperature.

After reacting, the reaction medium was poured over a mixture constituted of water, ice and sodium hydroxide (pH 12-13). A dark precipitate appeared. This was filtered through a frit, then dried under vacuum. 4.6 g of a black powder corresponding to compound 18 were obtained.

The NMR spectra and the mass spectra conformed to the expected product 18.

Step 3:

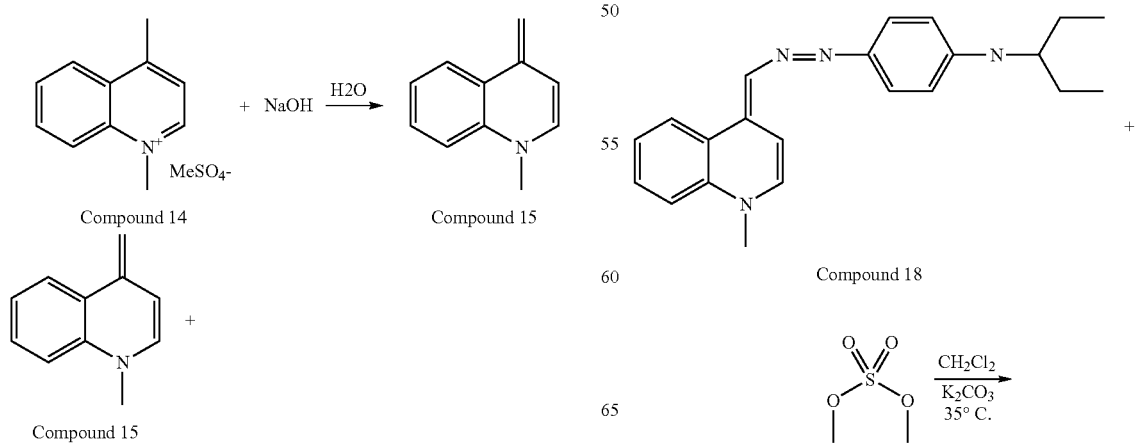

Compound 18

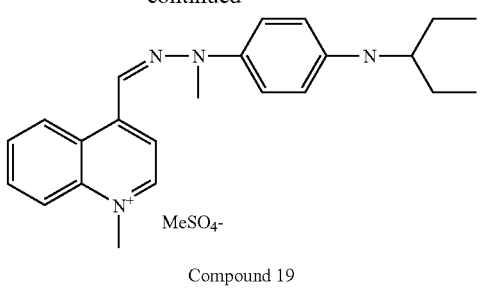

Compound 19

In a round-bottomed flask equipped with a bubbler, compound 18 (1.97 g) dissolved in 10 ml of dichloromethane and 3 ml of ethanol was stirred at 35° C. Two spatula tip-fulls of K$_2$CO$_3$ were added to the preceding reaction medium.

Next, dimethylsulphate (1.622 g; 2.2 eq.) was introduced into the preceding reaction medium and left stirring for 8 h at 35° C., then overnight at ambient temperature.

After reacting, the product was precipitated by adding 300 ml of ethyl acetate to the reaction medium. This was filtered, then dried under vacuum. After purification on a flash silica column (eluent: CH$_2$Cl$_2$/MeOH/AcOH 8/2/1), 0.5 g of a powder corresponding to compound 19 was obtained.

The NMR spectra and the mass spectra conformed to the expected product 19.

Example 7

Synthesis of the 4-{(Z)-[(4-anilino-2-methoxyphenyl)(methyl)hydrazono]methyl}-1-methylquinolinium methosulphate salt (21)

Compound 21

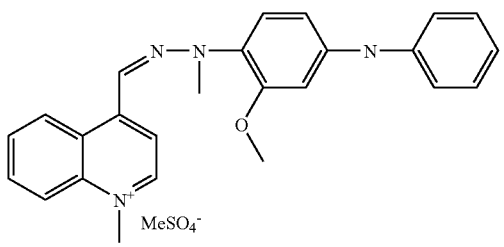

Step 1:

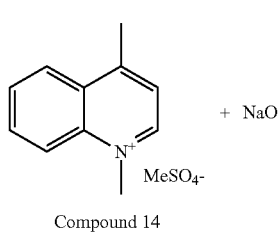

Compound 14       Compound 15

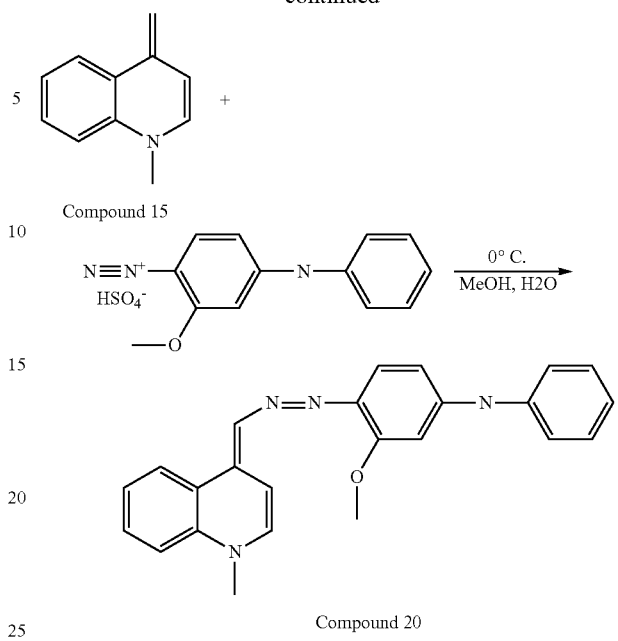

Compound 20

Compound 14 (3.07 g) in solution in 50 ml of iced water was introduced into an Erlenmeyer flask.

A 35% sodium hydroxide solution was added dropwise to the preceding reaction medium. A precipitate then appeared; this was filtered, then dried under vacuum. A pinkish powder corresponding to compound 15 was obtained.

In a beaker, 2-methoxy-4-(phenylamino)benzenediazonium hydrogensulphate (3.34 g—commercial product), dissolved in 30 ml of methanol and 30 ml of water, was cooled to 0° C. using a bath of iced water. The pinkish compound 15 (1.81 g), in suspension in 50 ml of methanol, was added slowly thereto.

The whole mixture was stirred for 2 h while allowing the temperature of the reaction medium to return to ambient temperature.

After reacting, the reaction medium was poured over a mixture constituted of water, ice and sodium hydroxide (pH 12-13). A precipitate appeared. This was filtered through a frit, then dried under vacuum. After purification on a silica column (eluent: CH$_2$Cl$_2$/MeOH/AcOH 8/2/1), 1.19 g of a black powder corresponding to compound 20 were obtained.

The NMR spectra and the mass spectra conformed to the expected product 20.

Step 2:

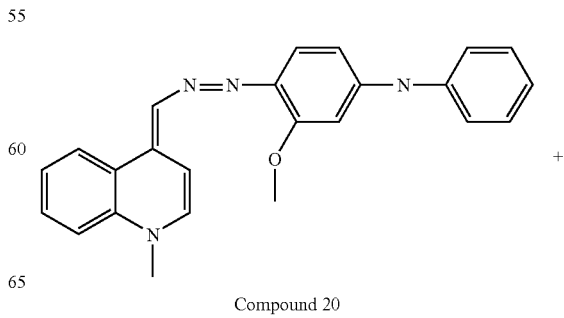

Compound 20

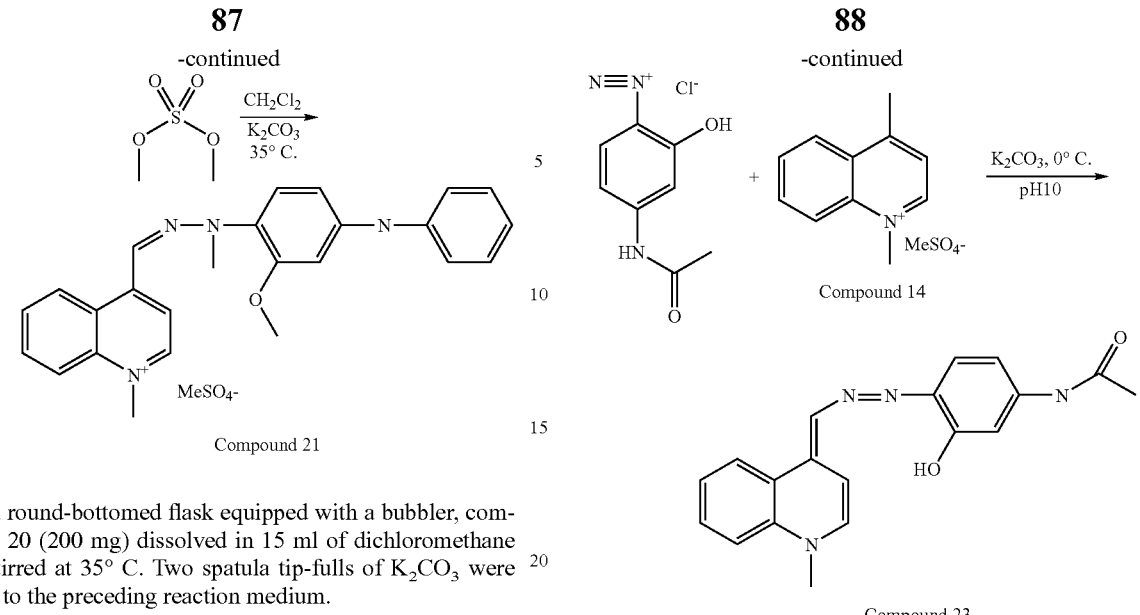

Compound 21

In a round-bottomed flask equipped with a bubbler, compound 20 (200 mg) dissolved in 15 ml of dichloromethane was stirred at 35° C. Two spatula tip-fulls of K₂CO₃ were added to the preceding reaction medium.

Next, dimethylsulphate (0.0665 g; 1.1 eq.) was introduced and left stirring for 4 h at 35° C.

After reacting, the product was precipitated by adding 300 ml of ethyl acetate to the reaction medium. The precipitate was subsequently filtered through a frit, then dried under vacuum. After purification on a silica column (eluent: CH₂Cl₂/MeOH/AcOH 8/2/1), 51 mg of a black powder corresponding to compound 21 were obtained.

The NMR spectra and the mass spectra conformed to the expected product 21.

Example 8

Synthesis of the 4-{(Z)-[[4-(acetylamino)-2-hydroxyphenyl](methyl) hydrazono]methyl}-1-methylquinolinium methyl sulphate methosulphate salt (24)

Compound 24

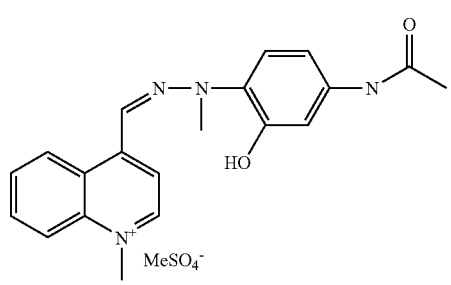

Step 1:

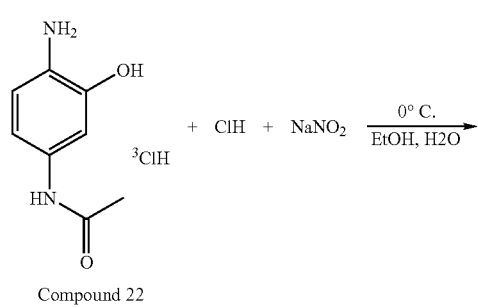

Compound 22

Compound 22 (200 mg), in solution in 1 ml of water, 3 ml of ethanol and 2 ml of concentrated (12N)HCl, was introduced into a three-necked flask equipped with a thermometer. The solution was first cooled to 0° C. using a bath of iced water, then a solution of sodium nitrite (68 mg in 2 ml of water) was added dropwise.

After stirring for 5 min at 0° C., a solution of urea (65 mg in 2 ml of water) was introduced.

In a three-necked flask equipped with a thermometer and a pH meter, compound 14 (197 mg), dissolved in 5 ml of ethanol and 2 ml of water, was cooled to 0° C. The pH of the solution was brought back to 10.5 using a solution of potassium carbonate (13 g in 75 ml of water). The diazonium salt from compound 22 was added slowly thereto while maintaining the temperature of the reaction mixture at 0° C. and a reaction pH between 8 and 10.5.

The whole mixture was stirred for 2 h while allowing the temperature of the reaction medium to return to ambient temperature.

After reacting, the reaction medium was poured over a mixture of iced water and sodium hydroxide (pH 12-13). A precipitate appeared. This was filtered through a frit and then dried under vacuum. 95.5 mg of a dark blue powder corresponding to compound 23 were obtained.

The NMR spectra and the mass spectra conformed to the expected product 23.

Step 2:

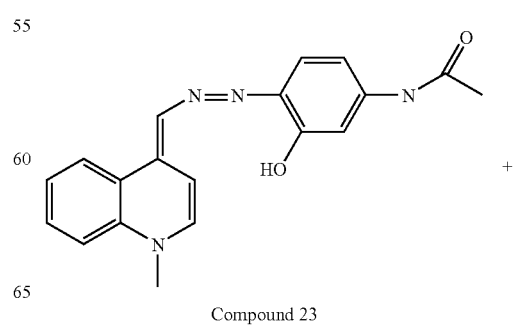

Compound 23

-continued

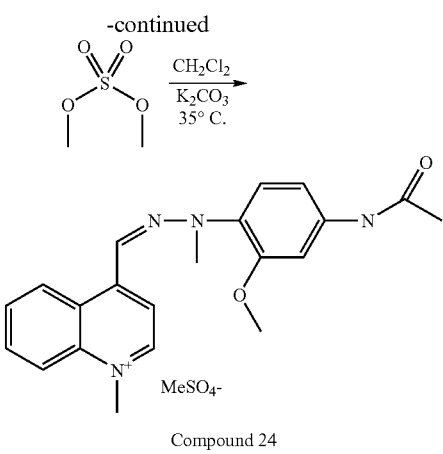

Compound 24

In a round-bottomed flask equipped with a bubbler, compound 23 (200 mg) dissolved in 3 ml of dichloromethane and 2 ml of a saturated aqueous solution of $K_2CO_3$ was stirred at 35° C.

Next, dimethylsulphate (0.133 g; 1.5 eq.) was introduced and left stirring for 4 h at 35° C., then 2 days at ambient temperature.

After reacting, the product was precipitated by adding 100 ml of diisopropyl ether to the reaction medium. This was filtered through a frit, then dried under vacuum. The product obtained was then purified by dissolving in a minimum amount of ethanol, then by precipitating in AcOEt.

168 mg of a brown-orange powder corresponding to compound 24 were obtained.

The NMR spectra and the mass spectra conformed to the expected product 24.

Examples of Dyes:

Dyeing compositions were prepared in the following proportions:

Solution 1:

| | |
|---|---|
| 60% aqueous solution of alkyl (C8/C10 50/50) polyglucoside (2) | 120 g |
| Pure absolute ethanol | 200 g |
| Polyethylene glycol (8 EO) 400 | 60 g |
| Pure benzyl alcohol | 40 g |
| Demineralized water | qs for 1000 g |

Solution 2: pH 9.5 Buffer

| | |
|---|---|
| Ammonium chloride (NH$_4$Cl) | 54 g |
| 20% aqueous ammonia solution | qs for pH = 9.5 (approx. 40 ml) |
| Demineralized water | qs for 1000 ml |

Solution 3: pH 7 Buffer

| | |
|---|---|
| KH$_2$PO$_4$ | 0.026 mol/l |
| Na$_2$PO$_4$ | 0.041 mol/l |
| Demineralized water | qs for 500 ml |

At pH 7, the dyeing compositions were obtained by dissolving the dye indicated below ($5 \times 10^{-3}$ mol/l) in solution 1 then by adding an equivalent volume of buffer solution 3.

Under alkaline lightening conditions, the dyeing compositions were obtained by dissolving the dye indicated below ($5 \times 10^{-3}$ mol/l) in solution 1 then by adding an equivalent volume of buffer solution 2 and a volume of 40-volume hydrogen peroxide.

Each composition was applied to grey hair containing 90% white hair, (1 g lock of hair per 6 g of solution). After a leave-in period of 30 min, the locks were rinsed, washed with a standard shampoo, rinsed again and then dried.

The following dyeing results were obtained.

| | After dyeing | |
|---|---|---|
| | pH 7 | Alkaline lightening conditions |
| | Chromatic yellow | Chromatic yellow |
| C. 1 Basic Yellow 87: compound I not in accordance with the invention | | |
| Compound 5 | Deep mahogany | Deep mahogany |
| Compound 12 | Deep red | Deep red |
| Compound 17 | Matt violet | Matt violet |

Example 9

Synthesis of the 1-methyl-4-{(E)-[methyl(4-pyrrolidin-1-yl -1-naphthyl)hydrazono]-methyl}quinolinium methosulphate salt (30)

Compound 30

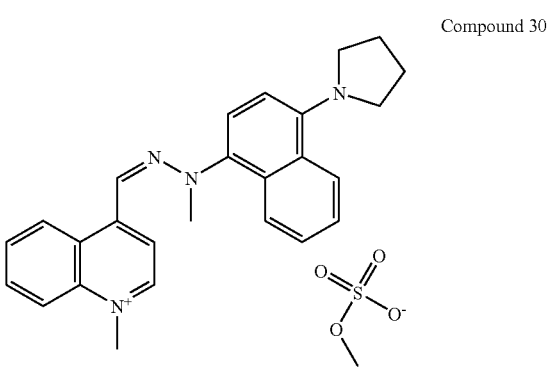

Step 1:

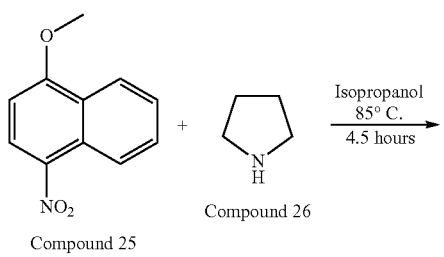

Compound 25      Compound 26

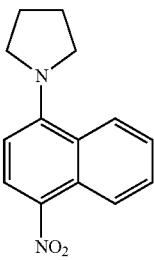

Compound 27

In a 50 ml three-necked flask equipped with a condenser, compound 25 (1 g; 1 eq.) and compound 26 (2 ml; 5 eq.), in solution in 1 ml of isopropanol, were stirred.

The reaction medium was then heated at 85° C. for 4.5 hours.

After reacting, the reaction medium was cooled, then evaporated to dryness.

The heterogeneous medium was then poured over 200 ml of a mixture constituted of water and ice. The precipitate formed was then filtered, washed several times with water, then dried under an active vacuum in the presence of $P_2O_5$.

1.13 g of a yellow powder corresponding to compound 27 were obtained.

The NMR spectra and the mass spectra conformed to the expected product 27.

Step 2

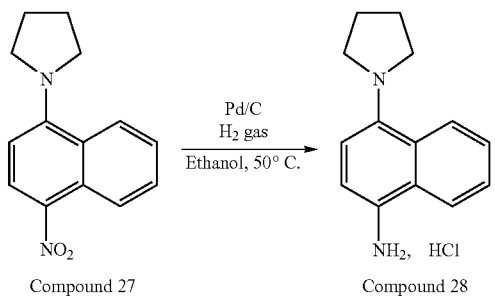

Compound 27      Compound 28

Compound 27 (10.5 g) and (10-30%) palladium on carbon (1.1 g) in solution in 500 ml of ethanol were stirred in a 1-litre reactor. The reaction medium was then heated at 50° C. Hydrogen was then introduced (22 bar) to the preceding mixture. The reaction medium was left under hydrogen at 50° C. for 1 hour.

After reacting, the reaction medium was cooled, then filtered. The homogeneous solution obtained was then poured over a dilute solution of hydrochloric acid (5N isopropanol) then stirred for a further hour.

A precipitate was gradually formed. This was filtered, washed with diisopropyl ether then dried under vacuum.

11.8 g of a light pink powder corresponding to compound 28 were obtained.

The NMR spectra and the mass spectra conformed to the expected product 28.

Step 3

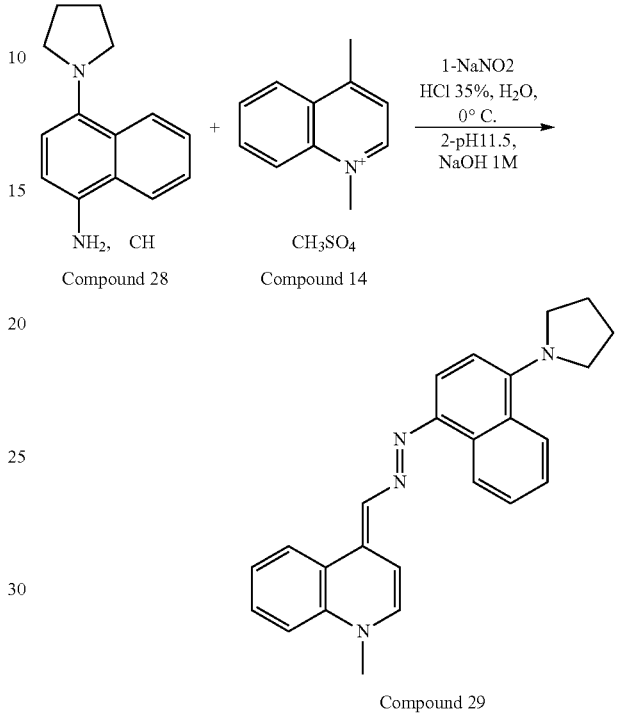

Compound 28      Compound 14

Compound 29

Compound 28 (0.5 g; 1 eq.), in solution in 5 ml of water and 5 ml of concentrated (35%) HCl, was introduced into a three-necked flask equipped with a thermometer. The solution was first cooled to 0° C. using a bath of iced water, then a solution of sodium nitrite (0.128 g; 1 eq.) dissolved in 2 ml of water previously cooled to 0° C., was added slowly dropwise to the preceding reaction medium.

After stirring for 20 min at 0° C., a solution of urea (120 mg in 2 ml of water) was introduced.

In a three-necked flask equipped with a thermometer and a pH meter, compound 14 (0.495 g, 1 eq.), dissolved in 5 ml of water, was cooled to 0° C. The diazonium salt from compound 28 was added slowly thereto while maintaining the temperature of the reaction medium at 0° C. Next, the pH of the solution was brought back to 10.5 using a 1N aqueous sodium hydroxide solution (10 ml).

The solution gradually darkened and a precipitate appeared.

The whole mixture was stirred for 2 h while allowing the temperature of the reaction medium to return to ambient temperature.

After reacting, the reaction medium was poured over a mixture of water and ice. The precipitate obtained was filtered through a frit and then dried under an active vacuum in the presence of $P_2O_5$.

0.5 g of a dark blue powder corresponding to compound 29 were obtained.

The NMR spectra and the mass spectra conformed to the expected product 29.

Step 4:

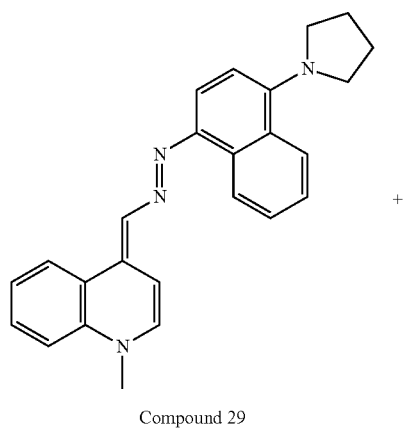

Compound 29

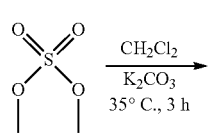
CH₂Cl₂
K₂CO₃
35° C., 3 h →

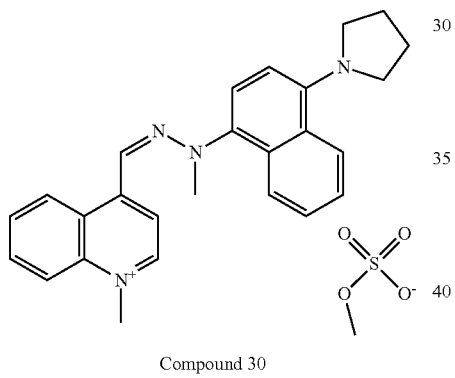

Compound 30

In a 50 ml round-bottomed flask equipped with a bubbler and a condenser, compound 29 (0.1 g) and 20 mg of potassium carbonate, dissolved in 4 ml of dichloromethane, were stirred at 35° C.

Next, dimethylsulphate (0.08 ml; 3 eq.) was introduced and left stirring for 3 hours at 35° C.

After reacting, the temperature of the reaction medium was left to return to ambient temperature. The expected product was precipitated by adding 100 ml of diisopropyl ether to the reaction medium.

This was filtered through a frit.

The product obtained was then purified by dissolving in a minimum amount of ethanol, then by precipitating in diisopropyl ether.

96 mg of a brown-black powder corresponding to compound 30 were obtained.

The NMR spectra and the mass spectra conformed to the expected product 30.

Example 10

Synthesis of the 1-methyl-2-{(E)-[methyl(4-pyrrolidin-1-yl-1-naphthyl)hydrazono]-methyl}quinolinium methosulphate salt (35)

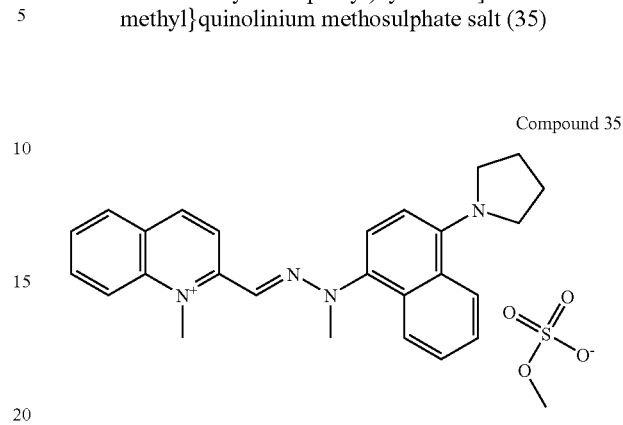

Compound 35

Step 1:

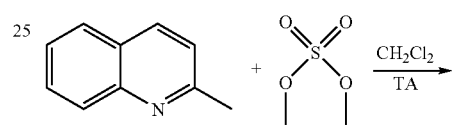
CH₂Cl₂
TA →

Compound 31

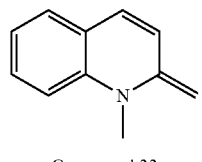

Compound 32

Compound 31 (10 g—commercial product) dissolved in 50 ml of dichloromethane was stirred in a round-bottomed flask equipped with a bubbler. Dimethylsulphate (8.91 g; 1 eq.) was then introduced into the preceding reaction medium.

The reaction medium was left stirring at ambient temperature overnight.

After reacting, the formation of a precipitate was observed. This was filtered and then dried under vacuum.

A white powder corresponding to compound 32 (15 g) was obtained.

The NMR spectra and the mass spectra conformed to the expected product 32.

Step 2:

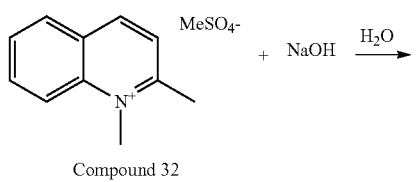

Compound 32

+ NaOH $\xrightarrow{H_2O}$

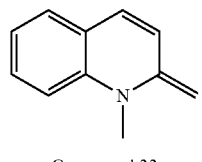

Compound 33

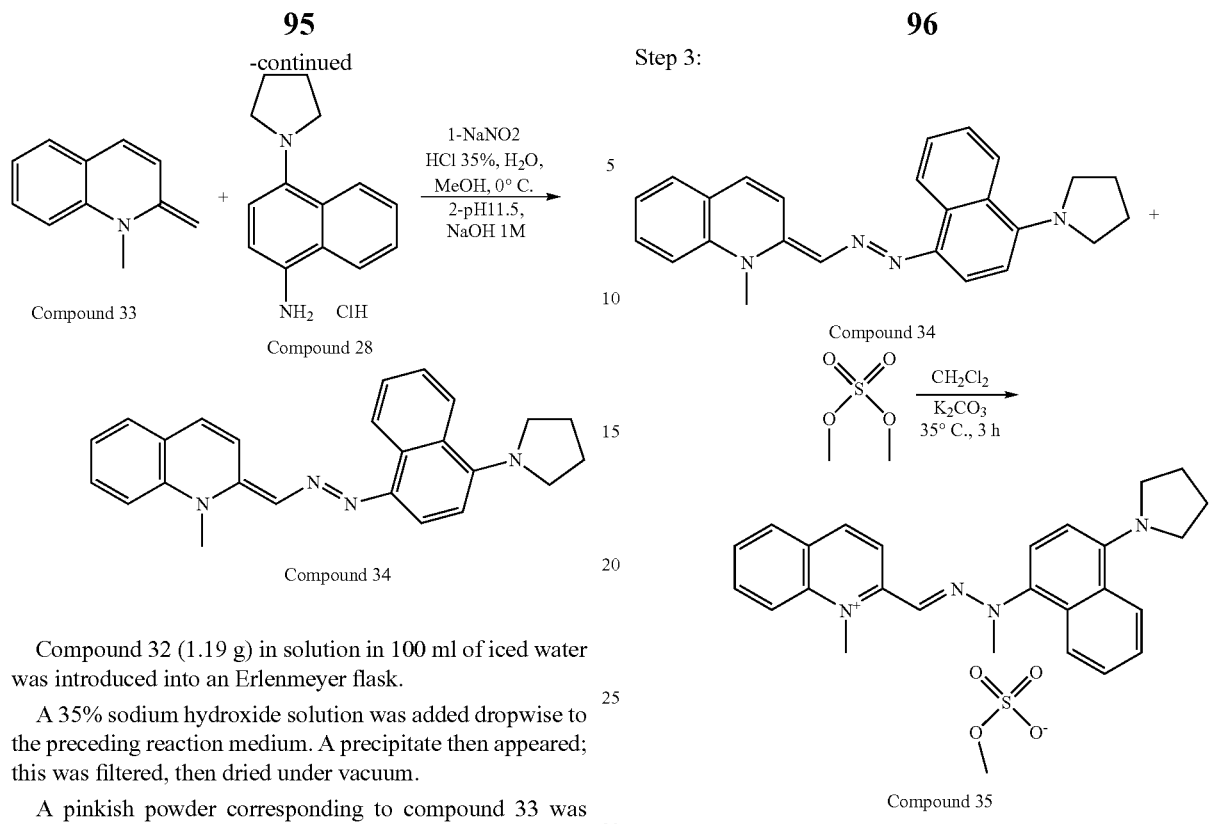

Compound 32 (1.19 g) in solution in 100 ml of iced water was introduced into an Erlenmeyer flask.

A 35% sodium hydroxide solution was added dropwise to the preceding reaction medium. A precipitate then appeared; this was filtered, then dried under vacuum.

A pinkish powder corresponding to compound 33 was obtained.

The NMR spectra and the mass spectra conformed to the expected product 33.

In a beaker, compound 28 (1 g; 1 eq.), in solution in 10 ml of water and 10 ml of concentrated (35%) HCl, was cooled to 0° C. using a bath of iced water. The solution was first cooled to 0° C. using a bath of iced water, then a solution of sodium nitrite (0.255 g; 1 eq.) dissolved in 2 ml of water previously cooled to 0° C., was added slowly dropwise to the preceding reaction medium.

After stirring for 20 min at 0° C., a solution of urea (225 mg in 2 ml of water) was introduced.

In a three-necked flask equipped with a thermometer and a pH meter, compound 33 obtained previously, dissolved in 20 ml of methanol, was cooled to 0° C. The diazonium salt from compound 28 was added slowly thereto while maintaining the temperature of the reaction mixture at 0° C. Next, the pH of the solution was brought back to 10.5 using a 1N aqueous sodium hydroxide solution (10 ml).

The solution gradually darkened and a precipitate appeared.

The whole mixture was stirred for 2 h while allowing the temperature of the reaction medium to return to ambient temperature.

After reacting, the reaction medium was poured over a mixture of water and ice. The precipitate obtained was filtered through a frit and then dried under an active vacuum in the presence of $P_2O_5$.

1.1 g of a dark blue powder corresponding to compound 34 were obtained.

The NMR spectra and the mass spectra conformed to the expected product 34.

Step 3:

In a 50 ml round-bottomed flask equipped with a bubbler and a condenser, compound 34 (0.1 g) and 20 mg of potassium carbonate, dissolved in 4 ml of dichloromethane, were stirred at 35° C.

Next, dimethylsulphate (0.08 ml; 3 eq.) was introduced and left stirring for 3 hours at 35° C.

After reacting, the temperature of the reaction medium was left to return to ambient temperature. The expected product was precipitated by adding 100 ml of diisopropyl ether to the reaction medium.

This was filtered through a frit. The product obtained was then purified by dissolving in a minimum amount of ethanol, then by precipitating in diisopropyl ether.

96 mg of a brown-black powder corresponding to compound 35 were obtained.

The NMR spectra and the mass spectra conformed to the expected product 35.

Examples of Dyes:

Dyeing compositions were prepared in the following proportions:

Solution 1:

| | |
|---|---|
| 60% aqueous solution of alkyl (C8/C10 50/50) polyglucoside (2) | 120 g |
| Pure absolute ethanol | 200 g |
| Polyethylene glycol (8 EO) 400 | 60 g |
| Pure benzyl alcohol | 40 g |
| Demineralized water | qs for 1000 g |

Solution 2: pH 9.5 Buffer

| | |
|---|---|
| Ammonium chloride ($NH_4Cl$) | 54 g |
| 20% aqueous ammonia solution | qs for pH = 9.5 (approx. 40 ml) |
| Demineralized water | qs for 1000 ml |

Solution 3: pH 7 Buffer

| KH$_2$PO$_4$ | 0.026 mol/l |
|---|---|
| Na$_2$PO$_4$ | 0.041 mol/l |
| Demineralized water | qs for 500 ml |

At pH 7, the dyeing compositions were obtained by dissolving the dye indicated below ($5\times10^{-3}$ mol/l) in solution 1 then by adding an equivalent volume of buffer solution 3.

Under alkaline lightening conditions, the dyeing compositions were obtained by dissolving the dye indicated below ($5\times10^{-3}$ mol/l) in solution 1 then by adding an equivalent volume of buffer solution 2 and a volume of 40-volume hydrogen peroxide.

Each composition was applied to grey hair containing 90% white hair, (1 g lock of hair per 6 g of solution). After a leave-in period of 30 min, the locks were rinsed, washed with a standard shampoo, rinsed again and then dried.

The following dyeing results were obtained.

| | After dyeing | |
|---|---|---|
| | pH 7 | Alkaline lightening conditions |
| Compound 30 | yellow | yellow |
| Compound 35 | yellow | yellow |

The invention claimed is:

1. At least one monocationic monochromophoric entity comprising one hydrazone entity, wherein the at least one monocationic monocromophoric entity comprising one hydrazone entity is chosen from those of formulae (I) and (II):

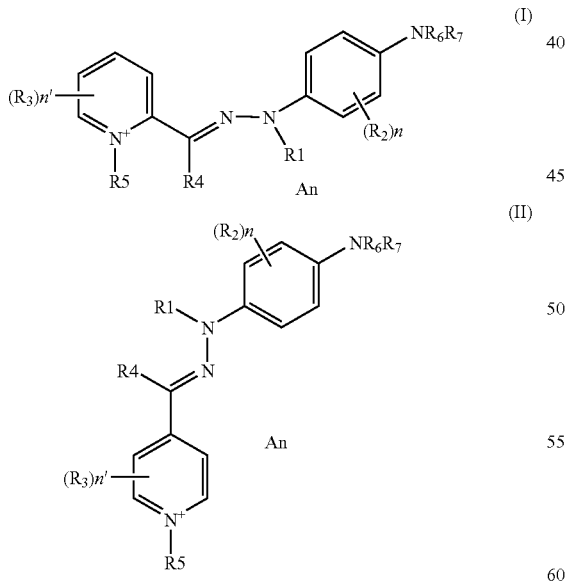

the mesomeric forms, addition salts with an acid, and solvates thereof:
wherein:
the $R_1$ radicals, which may be identical or different, represent, independently of one another:
a hydrogen;
an optionally substituted $C_1$-$C_{20}$ alkyl radical optionally interrupted by at least one heteroatom and/or by at least one group comprising at least one heteroatom; with the proviso that the alkyl radical does not comprise any nitro, nitroso, peroxo or diazo functional groups;
an optionally substituted phenyl radical;
an optionally substituted benzyl radical;
an alkylcarbonyl radical (R—CO—) wherein R represents a $C_1$-$C_4$ alkyl radical;
an alkylsulphonyl radical (RSO$_2$—)wherein R represents a $C_1$-$C_4$ alkyl radical;
an arylsulphonyl radical (R'SO$_2$—) wherein R' represents an optionally substituted phenyl or benzyl radical;
a (di)(alkyl) aminosulphonyl radical ((R$_2$N—SO$_2$—) wherein the R radicals independently represent a hydrogen or a $C_1$-$C_4$ alkyl radical; or
a (di)(alkyl)aminocarbonyl radical ((R)$_2$N—CO—) wherein the R radicals independently represent a hydrogen or a $C_1$-$C_4$ alkyl radical;
the $R_5$ radicals, which may be identical or different, represent, independently of one another:
an optionally substituted $C_1$-$C_{20}$ alkyl radical, optionally interrupted by at least one heteroatom and/or by at least one group comprising at least one heteroatom; with the proviso that the alkyl radical does not comprise any nitro, nitroso, peroxo or diazo functional groups;
a trimethylsilyl ($C_1$-$C_4$)alkyl radical;
an optionally substituted phenyl radical; or
an optionally substituted benzyl radical;
wherein the $R_2$, $R_3$ radicals, which may be identical or different, represent, independently of one another:
a halogen atom chosen from chlorine and fluorine;
a $C_1$-$C_8$ alkyl radical optionally substituted by at least one group chosen from hydroxyl, ((di)alkyl)amino, and sulphonylamino groups, optionally interrupted by at least one heteroatom and/or by at least one group comprising at least one heteroatom;
a hydroxyl radical;
a $C_1$-$C_4$ alkoxy radical;
a ($C_1$-$C_4$)alkoxycarbonyl radical;
an optionally substituted aryloxy radical;
an amino radical optionally substituted:
by one or two $C_1$-$C_4$ alkyl radicals, which may be identical or different, optionally bearing at least one hydroxyl or $C_1$-$C_2$ alkoxy group; or
by one or two phenyl, aminophenyl or methoxyphenyl radicals;
a ($C_1$-$C_4$)alkylcarbonylamino radical wherein the amino functional group may or may not be substituted by a $C_1$-$C_4$ alkyl radical;
an aminocarbonyl radical;
an aminosulphonyl, (di)($C_1$-$C_4$)alkylaminosulphonyl radical;
a ($C_1$-$C_4$)alkylthio radical;
a phenyl radical;
a trifluoromethyl radical; or
a thio radical;
wherein $R_1$ can form with an $R_2$ radical located in the ortho position with respect to the $NR_1$ group and with the nitrogen atom substituted by $R_1$, a substituted or unsubstituted, saturated or unsaturated heterocycle comprising 5 or 6 ring members;
wherein two adjacent $R_2$ radicals can form, with one another and with the carbon atoms to which they are attached, a substituted or unsubstituted, aromatic or non-aromatic (hetero)cyclic radical comprising 5 or 6 ring members;
wherein two adjacent $R_3$ radicals can form, with one another and with the carbon atoms to which they are attached, a substituted or unsubstituted aromatic ring comprising 5 or 6 ring members;
the $R_4$ radicals, which may be identical or different, represent, independently of one another:
  a hydrogen atom;
  an optionally substituted $C_1$-$C_{16}$ alkyl radical, optionally interrupted by at least one heteroatom and/or by at least one group comprising at least one heteroatom; with the proviso that the alkyl radical does not comprise any nitro, nitroso, peroxo or diazo functional groups;
  an amino radical optionally substituted by one or two $C_1$-$C_4$ alkyl radicals, which may be identical or different, optionally bearing at least one hydroxyl or $C_1$-$C_2$ alkoxy group, it being possible for said alkyl radicals to optionally form, with the nitrogen atom to which they are attached, a saturated or unsaturated or aromatic, optionally substituted heterocycle having 5 or 6 ring members, optionally comprising at least one other heteroatom which may be identical to or different from nitrogen;
  an alkylcarbonylamino radical (RCO—NR'—) wherein the R radical represents a $C_1$-$C_4$ alkyl radical and R' represents a hydrogen or a $C_1$-$C_4$ alkyl radical;
  a ureido radical (N(R)$_2$—CO—NR'—) wherein the R radicals, independently of one another, represent a $C_1$-$C_4$ alkyl radical, and R' represents a hydrogen or a $C_1$-$C_4$ alkyl radical;
  an alkylsulphonylamino radical (RSO$_2$—NR'—) wherein the R radical represents a $C_1$-$C_4$ alkyl radical, and R' represents a hydrogen or a $C_1$-$C_4$ alkyl radical;
  a hydroxycarbonyl radical;
  a $C_1$-$C_4$ alkoxycarbonyl radical;
  a cyano radical;
  an optionally substituted phenyl radical; or
  an optionally substituted benzyl radical;
the $R_6$ and $R_7$ radicals, which may be identical or different, represent, independently of one another:
  a hydrogen atom;
  an optionally substituted $C_1$-$C_{16}$ alkyl radical, optionally interrupted by at least one heteroatoms and/or by at least one group comprising at least one heteroatom; with the proviso that the alkyl radical does not comprise any nitro, nitroso, peroxo or diazo functional groups;
  an (alkoxy)aryl radical (-Ph-OR) wherein the R radical represents a hydrogen or a $C_1$-$C_4$ alkyl radical;
  a (di)(alkyl)aminoaryl radical (-Ph-N(R)$_2$) wherein the R radicals, independently of one another, represent a hydrogen or a $C_1$-$C_4$ alkyl radical optionall substituted by a hydroxyl;
  an alkylsulphonyl radical (RSO$_2$—) wherein the R radical represents a $C_1$-$C_4$ alkyl radical;
  an aminocarbonyl radical, a (di)($C_1$-$C_4$)alkylaminocarbonyl radical;
  a $CH_3CO$— radical;
  a phenyl; or
  a benzyl optionally substituted by at least one hydroxyl and/or amino group;
wherein the $R_6$ and $R_7$ radicals can optionally form with the nitrogen atom to which they are attached, a saturated or unsaturated, optionally substituted heterocycle comprising from 5 to 7 ring members, optionally comprising another heteroatom which may be identical to or different from nitrogen;
wherein one of the $R_6$ or $R_7$ radicals can also form with the nitrogen atom to which it is attached and with an $R_2$ radical located in the ortho position with respect to the $NR_6R_7$ group, a substituted or unsubstituted, saturated or unsaturated heterocycle comprising 5 or 6 ring members;
wherein the $R_6$ and $R_7$ radicals can form with the nitrogen atom to which the are attached and each with an $R_2$ radical located in the ortho position with respect to the $NR_6R_7$ group, a substituted or unsubstituted, saturated or unsaturated heterocycle comprising 5 or 6 ring members;
n is an integer ranging from 1 to 4, wherein when n is below 4, the unsubstituted carbon atom or atoms bear(s) a hydrogen atom;
n' is an integer ranging from 1 to 4, wherein when n' is below 4, the unsubstituted carbon atom or atoms bear(s) a hydrogen atom;
the electroneutrality of the compounds of formulae (I) and/or (II) being ensured by at least one cosmetically acceptable anion An, which may be identical or different.

2. A dyeing composition comprising, as direct dye, in a medium suitable for dyeing keratin fibers, at least one monocationic monochromophoric entity comprising one hydrazone entity, wherein the at least one monocationic monochromophoric entity comprising one hydrazone entity is chosen from those of formulae (I) and (II):

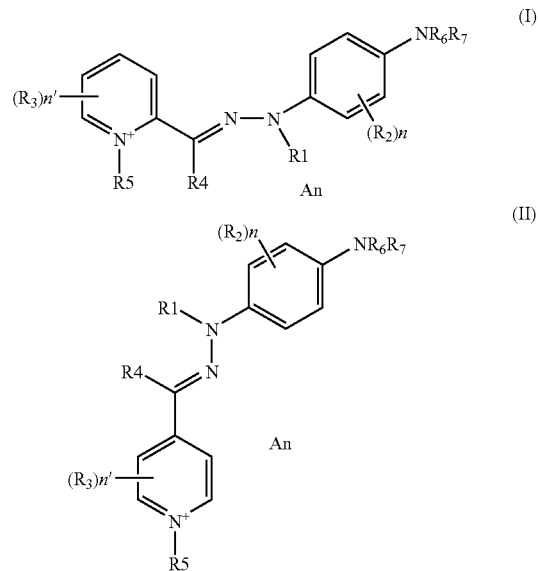

the mesomeric forms, addition salts with an acid, and solvates thereof:
  wherein:
  the $R_1$ radicals, which may be identical or different, represent, independently of one another:
    a hydrogen;
    an optionally substituted $C_1$-$C_{20}$ alkyl radical, optionally interrupted by at least one heteroatom and/or by at least one group comprising at least one heteroatom; with the proviso that the alkyl radical does not comprise any nitro, nitroso, peroxo or diazo functional groups;

an optionally substituted phenyl radical;
an optionally substituted benzyl radical;
an alkylcarbonyl radical (R—CO—) wherein R represents a $C_1$-$C_4$ alkyl radical;
an alkylsulphonyl radical ($RSO_2$—) wherein R represents a $C_1$-$C_4$ alkyl radical;
an arylsulphonyl radical ($R'SO_2$—) wherein R' represents an optionally substituted phenyl or benzyl radical;
a (di)(alkyl)aminosulphonyl radical (($R)_2N$—$SO_2$—) wherein the R radicals independently represent a hydrogen or a $C_1$-$C_4$ alkyl radical; or
a (di)(alkyl)aminocarbonyl radical (($R)_2N$—CO—) wherein the R radicals independently represent a hydrogen or a $C_1$-$C_4$ alkyl radical;
the $R_5$ radicals, which may be identical or different, represent, independently of one another:
an optionally substituted $C_1$-$C_{20}$ alkyl radical, optionally interrupted by at least one heteroatom and/or by at least one group comprising at least one heteroatom; with the proviso that the alkyl radical does not comprise any nitro, nitroso, peroxo or diazo functional groups;
a trimethylsilyl($C_1$-$C_4$)alkyl radical;
an optionally substituted phenyl radical; or
an optionally substituted benzyl radical;
the $R_2$ and $R_3$ radicals, which may be identical or different, represent, independently of one another:
a halogen atom;
an optionally substituted $C_1$-$C_{16}$ alkyl radical, optionally interrupted by at least one heteroatom and/or by at least one groups comprising at least one heteroatom; with the proviso that the alkyl radical does not comprise any nitro, nitroso, peroxo or diazo functional groups;
a hydroxyl radical;
a $C_1$-$C_4$ alkoxy radical; a $C_2$-$C_4$ (poly)hydroxyalkoxy group;
an alkoxycarbonyl radical (RO—CO—) wherein R represents a $C_1$-$C_4$ alkyl radical;
an alkylcarbonyloxy radical (RCO—O) wherein R represents a $C_1$-$C_4$ alkyl radical;
an optionally substituted aryloxy radical;
an optionally substituted (di)arylamino radical;
an amino radical optionally substituted by one or two $C_1$-$C_4$ alkyl radicals, which may be identical or different, optionally bearing at least one hydroxyl or $C_1$-$C_2$ alkoxy group, it being possible for said alkyl radicals to optionally form, with the nitrogen atom to which they are attached, a saturated or unsaturated, optionally substituted, optionally aromatic heterocycle having 5 or 7 ring members, optionally comprising another heteroatom which may be identical to or different from nitrogen;
an alkylcarbonylamino radical (RCO—NR'—) wherein the R radical represents a $C_1$-$C_4$ alkyl radical and R' represents a hydrogen or a $C_1$-$C_4$ alkyl radical;
a (di)(alkyl)aminocarbonyl group (($R)_2N$—CO—) wherein the R radicals, independently of one another, represent a hydrogen or a $C_1$-$C_4$ alkyl radical;
a ureido radical ($N(R)_2$—CO—NR'—) wherein the R radicals, independently of one another, represent a $C_1$-$C_4$ alkyl radical, and R' represents a hydrogen or a $C_1$-$C_4$ alkyl radical;
a (di)(alkyl)aminosulphonyl radical (($R)_2N$—$SO_2$—) wherein the R radicals, independently of one another represent a hydrogen atom or a $C_1$-$C_4$ alkyl radical;
an alkylthio radical (R—S—) wherein the R radical represents a $C_1$-$C_4$ alkyl radical;
an alkylsulphonylamino radical ($RSO_2$—NR'—) wherein the R radical represents a $C_1$-$C_4$ alkyl radical, and the R' radical represents a hydrogen atom or a $C_1$-$C_4$ alkyl radical;
a cyano radical (—C≡N);
a phenyl radical;
a trifluoromethyl radical (—$CF_3$);
a thio (—SH) radical;
an alkylsulphinyl radical (RSO—) wherein the R radical represents a $C_1$-$C_4$ alkyl radical; or
an alkylsulphonyl radical ($RSO_2$—) wherein the R radical represents a $C_1$-$C_4$ alkyl radical;
wherein $R_1$ can form with an $R_2$ radical located in the ortho position with respect to the $NR_1$ group and with the nitrogen atom substituted by a substituted or unsubstituted, saturated or unsaturated heterocycle comprising 5 or 6 ring members;
wherein two adjacent $R_2$ radicals can form, with one another and with the carbon atoms to which they are attached, a substituted or unsubstituted, aromatic or non-aromatic(hetero)cyclic radical comprising 5 or 6 ring members;
wherein two adjacent $R_3$ radicals can form, with one another and with the carbon atoms to which they are attached, a substituted or unsubstituted aromatic ring comprising 5 or 6 ring members;
the $R_4$ radicals, which may be identical or different, represent, independently of one another:
a hydrogen atom;
an optionally substituted $C_1$-$C_{16}$ alkyl radical, optionally interrupted by at least one heteroatoms and/or by at least one group comprising at least one heteroatom; with the proviso that the alkyl radical does not comprise any nitro, nitroso, peroxo or diazo functional groups;
an amino radical optionally substituted by one or two $C_1$-$C_4$ alkyl radicals, which may be identical or different, optionally bearing at least one hydroxyl or $C_1$-$C_2$ alkoxy group, it being possible for said alkyl radicals to optionally form, with the nitrogen atom to which they are attached, a saturated or unsaturated or aromatic, optionally substituted heterocycle having 5 or 6 ring members, optionally comprising at least one other heteroatom which may be identical to or different from nitrogen;
an alkylcarbonylamino radical (RCO—NR'—) wherein the R radical represents a $C_1$-$C_4$ alkyl radical and R' represents a hydrogen or a $C_1$-$C_4$ alkyl radical;
a ureido radical ($N(R)_2$—CO—NR'—) wherein the R radicals, independently of one another, represent a $C_1$-$C_4$ alkyl radical, and R' represents a hydrogen or a $C_1$-$C_4$ alkyl radical;
an alkylsulphonylamino radical ($RSO_2$—NR'—) wherein the R radical represents a $C_1$-$C_4$ alkyl radical, and R' represents a hydrogen or a $C_1$-$C_4$ alkyl radical;
a hydroxycarbonyl radical;
a $C_1$-$C_4$ alkoxycarbonyl radical;
a cyano radical;
an optionally substituted phenyl radical; or
an optionally substituted benzyl radical;
the $R_6$ and $R_7$ radicals, which may be identical or different, represent, independently of one another:
a hydrogen atom;
an optionally substituted $C_1$-$C_{16}$ alkyl radical, optionally interrupted by at least one heteroatoms and/or by at least one group comprising at least one heteroatom; with the proviso that the alkyl radical does not comprise any nitro, nitroso, peroxo or diazo functional groups;

an (alkoxy)aryl radical (-Ph-OR) wherein the R radical represents a hydrogen or a $C_1$-$C_4$ alkyl radical;

a (di)(alkyl)aminoaryl radical (-Ph-N(R)$_2$) wherein the R radicals, independently of one another, represent a hydrogen or a $C_1$-$C_4$ alkyl radical optionally substituted by a hydroxyl;

an alkylsulphonyl radical (RSO$_2$—) wherein the R radical represents a $C_1$-$C_4$ alkyl radical;

an aminocarbonyl radical, a (di)($C_1$-$C_4$)alkylaminocarbonyl radical;

a CH$_3$CO— radical;

a phenyl; or a benzyl optionally substituted by at least one hydroxyl and/or amino group;

wherein the $R_6$ and $R_7$ radicals can optionally form with the nitrogen atom to which they are attached, a saturated or unsaturated, optionally substituted heterocycle comprising from 5 to 7 ring members, optionally comprising another heteroatom which may be identical to or different from nitrogen;

wherein one of the $R_6$ or $R_7$ radicals can also form with the nitrogen atom to which it is attached and with an $R_2$ radical located in the ortho position with respect to the $NR_6R_7$ group, a substituted or unsubstituted, saturated or unsaturated heterocycle comprising 5 or 6 ring members;

wherein the $R_6$ and $R_7$ radicals can form with the nitrogen atom to which they are attached and each with an $R_2$ radical located in the ortho position with respect to the $NR_6R_7$ group, a substituted or unsubstituted, saturated or unsaturated heterocycle comprising 5 or 6 ring members;

n is an integer ranging from 0 to 4, wherein when n is below 4, the unsubstituted carbon atom or atoms bear(s) a hydrogen atom;

n' is an integer ranging from 0 to 4, wherein when n' is below 4, the unsubstituted carbon atom or atoms bear(s) a hydrogen atom;

the electroneutrality of the compounds of formulae (I) and/or (II) being ensured by at least one cosmetically acceptable anion An, which may be identical or different.

3. The dyeing composition according to claim 2, wherein of the at least one monocationic monochromophoric entity comprising one hydrazone entity chosen from those of formulae (I) and (II) is present in an amount ranging from 0.001 to 20% by weight relative to the total weight of the dyeing composition.

4. The dyeing composition according to claim 2, further comprising at least one additional direct dye, at least one oxidation base optionally combined with at least one coupler, or mixtures thereof.

5. The dyeing composition according to claim 2, further comprising at least one oxidizing agent.

6. A method for dyeing keratin fibres comprising:
applying to the keratin fibers, at least one composition comprising at least one monocationic monochromophoric entity comprising one hydrazone entity, wherein the monocationic monochromophoric entity comprising one hydrazone entity is chosen from those of formulae (I) and (II):

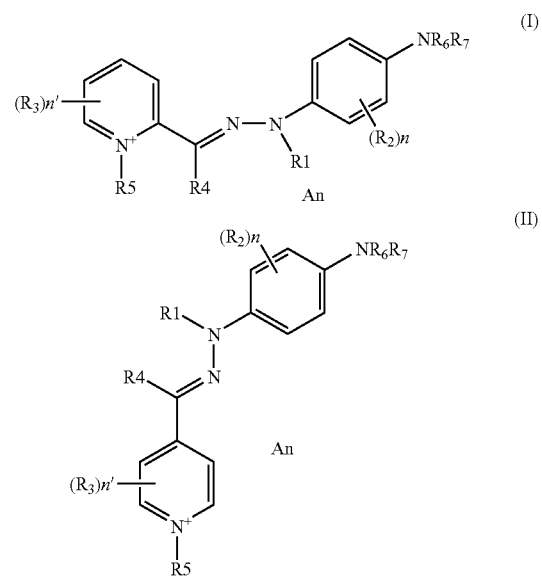

the mesomeric forms, addition salts with an acid, and solvates thereof:

wherein:

the $R_1$ radicals, which may be identical or different, represent, independently of one another:
a hydrogen;
an optionally substituted $C_1$-$C_{20}$ alkyl radical, optionally interrupted by at least one heteroatom and/or by at least one group comprising at least one heteroatom; with the proviso that the alkyl radical does not comprise any nitro, nitroso, peroxo or diazo functional groups;
an optionally substituted phenyl radical;
an optionally substituted benzyl radical;
an alkylcarbonyl radical (R—CO—) wherein R represents a $C_1$-$C_4$ alkyl radical;
an alkylsulphonyl radical (RSO$_2$—) wherein R represents a $C_1$-$C_4$ alkyl radical;
an arylsulphonyl radical (R'SO$_2$—) wherein R' represents an optionally substituted phenyl or benzyl radical;
a (di)(alkyl)aminosulphonyl radical ((R)$_2$N—SO$_2$—) wherein the R radicals independently represent a hydrogen or a $C_1$-$C_4$ alkyl radical; or
a (di)(alkyl)aminocarbonyl radical ((R)$_2$N—CO—) wherein the R radicals independently represent a hydrogen or a $C_1$-$C_4$ alkyl radical;

the $R_5$ radicals, which may be identical or different, represent, independently of one another:
an optionally substituted $C_1$-$C_{20}$ alkyl radical, optionally interrupted by at least one heteroatom and/or by at least one group comprising at least one heteroatom; with the proviso that the alkyl radical does not comprise any nitro, nitroso, peroxo or diazo functional groups;
a trimethylsilyl($C_1$-$C_4$)alkyl radical;
an optionally substituted phenyl radical; or
an optionally substituted benzyl radical;

the $R_2$ and $R_3$ radicals, which may be identical or different, represent, independently of one another:
a halogen atom;
an optionally substituted $C_1$-$C_{16}$ alkyl radical, optionally interrupted by at least one heteroatom and/or by at least one groups comprising at least one heteroatom; with the proviso that the alkyl radical does not comprise any nitro, nitroso, peroxo or diazo functional groups;
a hydroxyl radical;
a $C_1$-$C_4$ alkoxy radical; a $C_2$-$C_4$ (poly)hydroxyalkoxy group;
an alkoxycarbonyl radical (RO—CO—) wherein R represents a $C_1$-$C_4$ alkyl radical; an alkylcarbonyloxy radical (RCO—O) wherein R represents a $C_1$-$C_4$ alkyl radical;
an optionally substituted aryloxy radical;
an optionally substituted (di)arylamino radical;
an amino radical optionally substituted by one or two $C_1$-$C_4$ alkyl radicals, which may be identical or different, optionally bearing at least one hydroxyl or $C_1$-$C_2$ alkoxy group, it being possible for said alkyl radicals to optionally form, with the nitrogen atom to which they are attached, a saturated or unsaturated, optionally substituted, optionally aromatic heterocycle having 5 or 7 ring members, optionally comprising another heteroatom which may be identical to or different from nitrogen;
an alkylcarbonylamino radical (RCO—NR'—) wherein the R radical represents a $C_1$-$C_4$ alkyl radical and R' represents a hydrogen or a $C_1$-$C_4$ alkyl radical;
a (di)(alkyl)aminocarbonyl group (($R)_2$N—CO—) wherein the R radicals, independently of one another, represent a hydrogen or a $C_1$-$C_4$ alkyl radical;
a ureido radical (N$(R)_2$—CO—NR'—) wherein the R radicals, independently of one another, represent a $C_1$-$C_4$ alkyl radical, and R' represents a hydrogen or a $C_1$-$C_4$ alkyl radical;
a (di)(alkyl)aminosulphonyl radical (($R)_2$N—$SO_2$—) wherein the R radicals, independently of one another represent a hydrogen atom or a $C_1$-$C_4$ alkyl radical;
an alkylthio radical (R—S—) wherein the R radical represents a $C_1$-$C_4$ alkyl radical;
an alkylsulphonylamino radical ($RSO_2$—NR'—) wherein the R radical represents a $C_1$-$C_4$ alkyl radical, and the R' radical represents a hydrogen atom or a $C_1$-$C_4$ alkyl radical;
a cyano radical (—C≡N);
a phenyl radical;
a trifluoromethyl radical (—$CF_3$);
a thio (—SH) radical;
an alkylsulphinyl radical (RSO—) wherein the R radical represents a $C_1$-$C_4$ alkyl radical; or
an alkylsulphonyl radical ($RSO_2$—) wherein the R radical represents a $C_1$-$C_4$ alkyl radical;
wherein $R_1$ can form with an $R_2$ radical located in the ortho position with respect to the $NR_1$ group and with the nitrogen atom substituted by $R_1$, a substituted or unsubstituted, saturated or unsaturated heterocycle comprising 5 or 6 ring members;
wherein two adjacent $R_2$ radicals can form, with one another and with the carbon atoms to which they are attached, a substituted or unsubstituted, aromatic or non-aromatic (hetero)cyclic radical comprising 5 or 6 ring members;
wherein two adjacent $R_3$ radicals can form, with one another and with the carbon atoms to which they are attached, a substituted or unsubstituted aromatic ring comprising 5 or 6 ring members;
the $R_4$ radicals, which may be identical or different, represent, independently of one another:
a hydrogen atom;
an optionally substituted $C_1$-$C_{16}$ alkyl radical, optionally interrupted by at least one heteroatoms and/or by at least one group comprising at least one heteroatom; with the proviso that the alkyl radical does not comprise any nitro, nitroso, peroxo or diazo functional groups;
an amino radical optionally substituted by one or two $C_1$-$C_4$ alkyl radicals, which may be identical or different, optionally bearing at least one hydroxyl or $C_1$-$C_2$ alkoxy group, it being possible for said alkyl radicals to optionally form, with the nitrogen atom to which they are attached, a saturated or unsaturated or aromatic, optionally substituted heterocycle having 5 or 6 ring members, optionally comprising at least one other heteroatom which may be identical to or different from nitrogen;
an alkylcarbonylamino radical (RCO—NR'—) wherein the R radical represents a $C_1$-$C_4$ alkyl radical and R' represents a hydrogen or a $C_1$-$C_4$ alkyl radical;
a ureido radical (N$(R)_2$—CO—NR'—) wherein the R radicals, independently of one another, represent a $C_1$-$C_4$ alkyl radical, and R' represents a hydrogen or a $C_1$-$C_4$ alkyl radical;
an alkylsulphonylamino radical ($RSO_2$—NR'—) wherein the R radical represents a $C_1$-$C_4$ alkyl radical, and R' represents a hydrogen or a $C_1$-$C_4$ alkyl radical;
a hydroxycarbonyl radical;
a $C_1$-$C_4$ alkoxycarbonyl radical;
a cyano radical;
an optionally substituted phenyl radical; or
an optionally substituted benzyl radical;
the $R_6$ and $R_7$ radicals, which may be identical or different, represent, independently of one another:
a hydrogen atom;
an optionally substituted $C_1$-$C_{16}$ alkyl radical, optionally interrupted by at least one heteroatoms and/or by at least one group comprising at least one heteroatom; with the proviso that the alkyl radical does not comprise any nitro, nitroso, peroxo or diazo functional groups;
an (alkoxy)aryl radical (-Ph-OR) wherein the R radical represents a hydrogen or a $C_1$-$C_4$ alkyl radical;
a (di)(alkyl)aminoaryl radical (-Ph-N$(R)_2$) wherein the R radicals, independently of one another, represent a hydrogen or a $C_1$-$C_4$ alkyl radical optionally substituted by a hydroxyl;
an alkylsulphonyl radical ($RSO_2$—) wherein the R radical represents a $C_1$-$C_4$ alkyl radical;
an aminocarbonyl radical, a (di)($C_1$-$C_4$)alkylaminocarbonyl radical;
a $CH_3CO$— radical;
a phenyl; or
a benzyl optionally substituted by at least one hydroxyl and/or amino group;
wherein the $R_6$ and $R_7$ radicals can optionally form with the nitrogen atom to which they are attached, a saturated or unsaturated, optionally substituted heterocycle comprising from 5 to 7 ring members, optionally comprising another heteroatom which may be identical to or different from nitrogen;
wherein one of the $R_6$ or $R_7$ radicals can also form with the nitrogen atom to which it is attached and with an $R_2$ radical located in the ortho position with respect to the NR$_6$R$_7$ group, a substituted or unsubstituted, saturated or unsaturated heterocycle comprising 5 or 6 ring members;

wherein the R$_6$ and R$_7$ radicals can form with the nitrogen atom to which they are attached and each with an R$_2$ radical located in the ortho position with respect to the NR$_6$R$_7$ group, a substituted or unsubstituted, saturated or unsaturated heterocycle comprising 5 or 6 ring members;

n is an integer ranging from 0 to 4, wherein when n is below 4, the unsubstituted carbon atom or atoms bear(s) a hydrogen atom;

n' is an integer ranging from 0 to 4, wherein when n' is below 4, the unsubstituted carbon atom or atoms bear(s) a hydrogen atom;

the electroneutrality of the compounds of formulae (I) and/or (II) being ensured by at least one cosmetically acceptable anion An, which may be identical or different, wherein the keratin fibers can be either dry or wet fibers, and leaving the at least one composition on the keratin fibers for a sufficient time to obtain the desired effect.

7. A multicompartment device comprising at least one first compartment comprising at least one monocationic monochromophoric entity comprising one hydrazone entity, wherein the monocationic monochromophoric entity comprising one hydrazone entity is chosen from those of formulae (I) and (II):

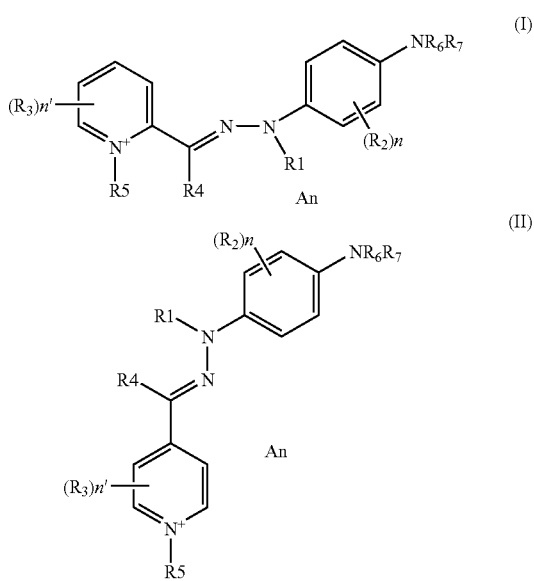

the mesomeric forms, addition salts with an acid, and solvates thereof:

wherein:

the R$_1$ radicals, which may be identical or different, represent, independently of one another:
a hydrogen;
an optionally substituted C$_1$-C$_{20}$ alkyl radical, optionally interrupted by at least one heteroatom and/or by at least one group comprising at least one heteroatom; with the proviso that the alkyl radical does not comprise any nitro, nitroso, peroxo or diazo functional groups;
an optionally substituted phenyl radical;
an optionally substituted benzyl radical;
an alkylcarbonyl radical (R—CO—) wherein R represents a C$_1$-C$_4$ alkyl radical;
an alkylsulphonyl radical (RSO$_2$—) wherein R represents a C$_1$-C$_4$ alkyl radical;
an arylsulphonyl radical (R'SO$_2$—) wherein R' represents an optionally substituted phenyl or benzyl radical;
a (di)(alkyl)aminosulphonyl radical ((R)$_2$N—SO$_2$—) wherein the R radicals independently represent a hydrogen or a C$_1$-C$_4$ alkyl radical; or
a (di)(alkyl)aminocarbonyl radical ((R)$_2$N—CO—) wherein the R radicals independently represent a hydrogen or a C$_1$-C$_4$ alkyl radical;

the R$_5$ radicals, which may be identical or different, represent, independently of one another:
an optionally substituted C$_1$-C$_{20}$ alkyl radical, optionally interrupted by at least one heteroatom and/or by at least one group comprising at least one heteroatom; with the proviso that the alkyl radical does not comprise any nitro, nitroso, peroxo or diazo functional groups;
a trimethylsilyl(C$_1$-C$_4$)alkyl radical;
an optionally substituted phenyl radical; or
an optionally substituted benzyl radical;

the R$_2$ and R$_3$ radicals, which may be identical or different, represent, independently of one another:
a halogen atom;
an optionally substituted C$_1$-C$_{16}$ alkyl radical, optionally interrupted by at least one heteroatom and/or by at least one groups comprising at least one heteroatom; with the proviso that the alkyl radical does not comprise any nitro, nitroso, peroxo or diazo functional groups;
a hydroxyl radical;
a C$_1$-C$_4$ alkoxy radical; a C$_2$-C$_4$ (poly)hydroxyalkoxy group;
an alkoxycarbonyl radical (RO—CO—) wherein R represents a C$_1$-C$_4$ alkyl radical;
an alkylcarbonyloxy radical (RCO—O) wherein R represents a C$_1$-C$_4$ alkyl radical;
an optionally substituted aryloxy radical;
an optionally substituted (di)arylamino radical;
an amino radical optionally substituted by one or two C$_1$-C$_4$ alkyl radicals, which may be identical or different, optionally bearing at least one hydroxyl or C$_1$-C$_2$ alkoxy group, it being possible for said alkyl radicals to optionally form, with the nitrogen atom to which they are attached, a saturated or unsaturated, optionally substituted, optionally aromatic heterocycle having 5 or 7 ring members, optionally comprising another heteroatom which may be identical to or different from nitrogen;
an alkylcarbonylamino radical (RCO—NR'—) wherein the R radical represents a C$_1$-C$_4$ alkyl radical and R' represents a hydrogen or a C$_1$-C$_4$ alkyl radical;
a (di)(alkyl)aminocarbonyl group ((R)$_2$N—CO—) wherein the R radicals, independently of one another, represent a hydrogen or a C$_1$-C$_4$ alkyl radical;
a ureido radical (N(R)$_2$—CO—NR'—) wherein the R radicals, independently of one another, represent a C$_1$-C$_4$ alkyl radical, and R' represents a hydrogen or a C$_1$-C$_4$ alkyl radical;
a (di)(alkyl)aminosulphonyl radical ((R)$_2$N—SO$_2$—) wherein the R radicals, independently of one another represent a hydrogen atom or a C$_1$-C$_4$ alkyl radical;
an alkylthio radical (R—S—) wherein the R radical represents a C$_1$-C$_4$ alkyl radical;

an alkylsulphonylamino radical ($RSO_2$—NR'—) wherein the R radical represents a $C_1$-$C_4$ alkyl radical, and the R' radical represents a hydrogen atom or a $C_1$-$C_4$ alkyl radical;

a cyano radical (—C≡N);

a phenyl radical;

a trifluoromethyl radical (—$CF_3$);

a thio (—SH) radical;

an alkylsulphinyl radical (RSO—) wherein the R radical represents a $C_1$-$C_4$ alkyl radical; or an alkylsulphonyl radical ($RSO_2$—) wherein the R radical represents a $C_1$-$C_4$ alkyl radical;

wherein $R_1$ can form with an $R_2$ radical located in the ortho position with respect to the $NR_1$ group and with the nitrogen atom substituted by $R_1$, a substituted or unsubstituted, saturated or unsaturated heterocycle comprising 5 or 6 ring members;

wherein two adjacent $R_2$ radicals can form, with one another and with the carbon atoms to which they are attached, a substituted or unsubstituted, aromatic or non-aromatic (hetero)cyclic radical comprising 5 or 6 ring members;

wherein two adjacent $R_3$ radicals can form, with one another and with the carbon atoms to which they are attached, a substituted or unsubstituted aromatic ring comprising 5 or 6 ring members;

the $R_4$ radicals, which may be identical or different, represent, independently of one another:

a hydrogen atom;

an optionally substituted $C_1$-$C_{16}$ alkyl radical, optionally interrupted by at least one heteroatoms and/or by at least one group comprising at least one heteroatom; with the proviso that the alkyl radical does not comprise any nitro, nitroso, peroxo or diazo functional groups;

an amino radical optionally substituted by one or two $C_1$-$C_4$ alkyl radicals, which may be identical or different, optionally bearing at least one hydroxyl or $C_1$-$C_2$ alkoxy group, it being possible for said alkyl radicals to optionally form, with the nitrogen atom to which they are attached, a saturated or unsaturated or aromatic, optionally substituted heterocycle having 5 or 6 ring members, optionally comprising at least one other heteroatom which may be identical to or different from nitrogen;

an alkylcarbonylamino radical (RCO—NR'—) wherein the R radical represents a $C_1$-$C_4$ alkyl radical and R' represents a hydrogen or a $C_1$-$C_4$ alkyl radical;

a ureido radical (N(R)$_2$—CO—NR'—) wherein the R radicals, independently of one another, represent a $C_1$-$C_4$ alkyl radical, and R' represents a hydrogen or a $C_1$-$C_4$ alkyl radical;

an alkylsulphonylamino radical ($RSO_2$—NR'—) wherein the R radical represents a $C_1$-$C_4$ alkyl radical, and R' represents a hydrogen or a $C_1$-$C_4$ alkyl radical;

a hydroxycarbonyl radical;

a $C_1$-$C_4$ alkoxycarbonyl radical;

a cyano radical;

an optionally substituted phenyl radical; or an optionally substituted benzyl radical;

the $R_6$ and $R_7$ radicals, which may be identical or different, represent, independently of one another:

a hydrogen atom;

an optionally substituted $C_1$-$C_{16}$ alkyl radical, optionally interrupted by at least one heteroatoms and/or by at least one group comprising at least one heteroatom; with the proviso that the alkyl radical does not comprise any nitro, nitroso, peroxo or diazo functional groups;

an (alkoxy)aryl radical (-Ph-OR) wherein the R radical represents a hydrogen or a $C_1$-$C_4$ alkyl radical;

a (di)(alkyl)aminoaryl radical (-Ph-N(R)$_2$) wherein the R radicals, independently of one another, represent a hydrogen or a $C_1$-$C_4$ alkyl radical optionally substituted by a hydroxyl;

an alkylsulphonyl radical ($RSO_2$—) wherein the R radical represents a $C_1$-$C_4$ alkyl radical;

an aminocarbonyl radical, a (di)($C_1$-$C_4$)alkylaminocarbonyl radical;

a $CH_3CO$— radical;

a phenyl; or a benzyl optionally substituted by at least one hydroxyl and/or amino group;

wherein the $R_6$ and $R_7$ radicals can optionally form with the nitrogen atom to which they are attached, a saturated or unsaturated, optionally substituted heterocycle comprising from 5 to 7 ring members, optionally comprising another heteroatom which may be identical to or different from nitrogen;

wherein one of the $R_6$ or $R_7$ radicals can also form with the nitrogen atom to which it is attached and with an $R_2$ radical located in the ortho position with respect to the $NR_6R_7$ group, a substituted or unsubstituted, saturated or unsaturated heterocycle comprising 5 or 6 ring members;

wherein the $R_6$ and $R_7$ radicals can form with the nitrogen atom to which they are attached and each with an $R_2$ radical located in the ortho position with respect to the $NR_6R_7$ group, a substituted or unsubstituted, saturated or unsaturated heterocycle comprising 5 or 6 ring members;

n is an integer ranging from 0 to 4, wherein when n is below 4, the unsubstituted carbon atom or atoms bear(s) a hydrogen atom;

n' is an integer ranging from 0 to 4, wherein when n' is below 4, the unsubstituted carbon atom or atoms bear(s) a hydrogen atom;

the electroneutrality of the compounds of formulae (I) and/or (II) being ensured by at least one cosmetically acceptable anion An, which may be identical or different;

and at least one second compartment comprising at least one oxidizing agent.

8. A method for preparing at least one monocationic monochromophoric entity comprising one hydrazone entity, wherein the at least one monocationic monochromophoric entity comprising one hydrazone entity is chosen from those of formulae (I) and (II)

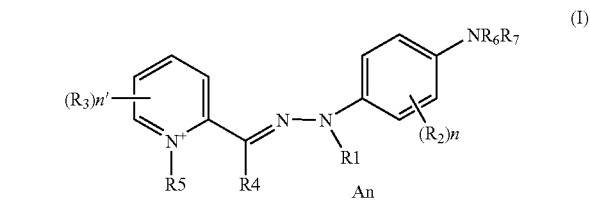

-continued

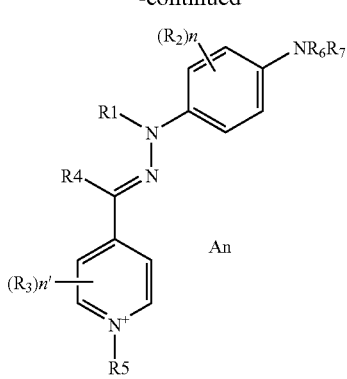

(II)

the mesomeric forms, addition salts with an acid, and/or solvates thereof:
comprising
(a) Condensing a heteroaromatic aldehyde or ketone with a hydrazine derivative according to the following reaction:

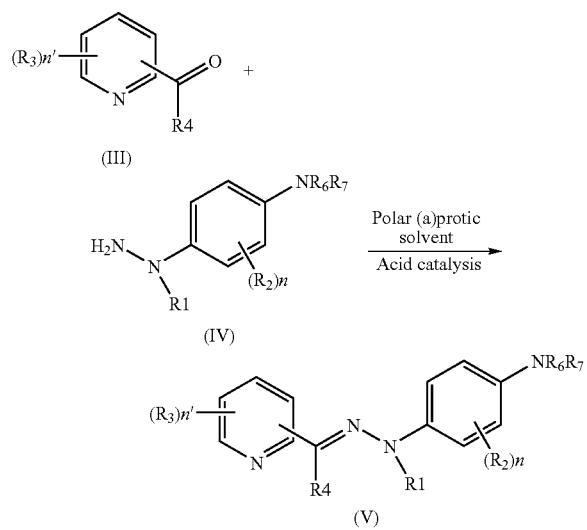

and
(b) Quaternizing the heterocyclic ring of formula (V) according to the following reaction:

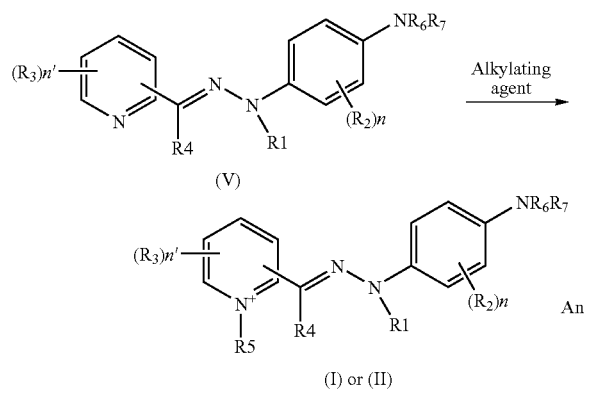

wherein, in formulae I and II:
the $R_1$ radicals, which may be identical or different, represent, independently of one another:
a hydrogen;
an optionally substituted $C_1$-$C_{20}$ alkyl radical, optionally interrupted by at least one heteroatom and/or by at least one group comprising at least one heteroatom; with the proviso that the alkyl radical does not comprise any nitro, nitroso, peroxo or diazo functional groups;
an optionally substituted phenyl radical;
an optionally substituted benzyl radical;
an alkylcarbonyl radical (R—CO—) wherein R represents a $C_1$-$C_4$ alkyl radical;
an alkylsulphonyl radical (RSO$_2$—) wherein R represents a $C_1$-$C_4$ alkyl radical;
an arylsulphonyl radical (R'SO$_2$—) wherein R' represents an optionally substituted phenyl or benzyl radical;
a (di)(alkyl)aminosulphonyl radical ((R)$_2$N—SO$_2$—) wherein the R radicals independently represent a hydrogen or a $C_1$-$C_4$ alkyl radical; or
a (di)(alkyl)aminocarbonyl radical ((R)$_2$N—CO—) wherein the R radicals independently represent a hydrogen or a $C_1$-$C_4$ alkyl radical;
the $R_5$ radicals, which may be identical or different, represent, independently of one another:
an optionally substituted $C_1$-$C_{20}$ alkyl radical, optionally interrupted by at least one heteroatom and/or by at least one group comprising at least one heteroatom; with the proviso that the alkyl radical does not comprise any nitro, nitroso, peroxo or diazo functional groups;
a trimethylsilyl($C_1$-$C_4$)alkyl radical;
an optionally substituted phenyl radical; or
an optionally substituted benzyl radical;
the $R_2$ and $R_3$ radicals, which may be identical or different, represent, independently of one another:
a halogen atom;
an optionally substituted $C_1$-$C_{16}$ alkyl radical, optionally interrupted by at least one heteroatom and/or by at least one groups comprising at least one heteroatom; with the proviso that the alkyl radical does not comprise any nitro, nitroso, peroxo or diazo functional groups;
a hydroxyl radical;
a $C_1$-$C_4$ alkoxy radical; a $C_2$-$C_4$ (poly)hydroxyalkoxy group;
an alkoxycarbonyl radical (RO—CO—) wherein R represents a $C_1$-$C_4$ alkyl radical;
an alkylcarbonyloxy radical (RCO—O) wherein R represents a $C_1$-$C_4$ alkyl radical;
an optionally substituted aryloxy radical;
an optionally substituted (di)arylamino radical;
an amino radical optionally substituted by one or two $C_1$-$C_4$ alkyl radicals, which may be identical or different, optionally bearing at least one hydroxyl or $C_1$-$C_2$ alkoxy group, it being possible for said alkyl radicals to optionally form, with the nitrogen atom to which they are attached, a saturated or unsaturated, optionally substituted, optionally aromatic heterocycle having 5 or 7 ring members, optionally comprising another heteroatom which may be identical to or different from nitrogen;
an alkylcarbonylamino radical (RCO—NR'—) wherein the R radical represents a $C_1$-$C_4$ alkyl radical and R' represents a hydrogen or a $C_1$-$C_4$ alkyl radical;

a (di)(alkyl)aminocarbonyl group (($R)_2$N—CO—) wherein the R radicals, independently of one another, represent a hydrogen or a $C_1$-$C_4$ alkyl radical;

a ureido radical (N(R)$_2$—CO—NR'—) wherein the R radicals, independently of one another, represent a $C_1$-$C_4$ alkyl radical, and R' represents a hydrogen or a $C_1$-$C_4$ alkyl radical;

a (di)(alkyl)aminosulphonyl radical (($_R$)$_2$N—SO$_2$—) wherein the R radicals, independently of one another represent a hydrogen atom or a $C_1$-$C_4$ alkyl radical;

an alkylthio radical (R—S—) wherein the R radical represents a $C_1$-$C_4$ alkyl radical;

an alkylsulphonylamino radical (RSO$_2$—NR'—) wherein the R radical represents a $C_1$-$C_4$ alkyl radical, and the R' radical represents a hydrogen atom or a $C_1$-$C_4$ alkyl radical;

a cyano radical (—C≡N);

a phenyl radical;

a trifluoromethyl radical (—CF$_3$);

a thio (—SH) radical;

an alkylsulphinyl radical (RSO—) wherein the R radical represents a $C_1$-$C_4$ alkyl radical; or an alkylsulphonyl radical (RSO$_2$—) wherein the R radical represents a $C_1$-$C_4$ alkyl radical;

wherein $R_1$ can form with an $R_2$ radical located in the ortho position with respect to the NR$_1$ group and with the nitrogen atom substituted by $R_1$, a substituted or unsubstituted, saturated or unsaturated heterocycle comprising 5 or 6 ring members;

wherein two adjacent $R_2$ radicals can form, with one another and with the carbon atoms to which they are attached, a substituted or unsubstituted, aromatic or non-aromatic (hetero)cyclic radical comprising 5 or 6 ring members;

wherein two adjacent $R_3$ radicals can form, with one another and with the carbon atoms to which they are attached, a substituted or unsubstituted aromatic ring comprising 5 or 6 ring members;

the $R_4$ radicals, which may be identical or different, represent, independently of one another:

a hydrogen atom;

an optionally substituted $C_1$-$C_{16}$ alkyl radical, optionally interrupted by at least one heteroatoms and/or by at least one group comprising at least one heteroatom; with the proviso that the alkyl radical does not comprise any nitro, nitroso, peroxo or diazo functional groups;

an amino radical optionally substituted by one or two $C_1$-$C_4$ alkyl radicals, which may be identical or different, optionally bearing at least one hydroxyl or $C_1$-$C_2$ alkoxy group, it being possible for said alkyl radicals to optionally form, with the nitrogen atom to which they are attached, a saturated or unsaturated or aromatic, optionally substituted heterocycle having 5 or 6 ring members, optionally comprising at least one other heteroatom which may be identical to or different from nitrogen;

an alkylcarbonylamino radical (RCO—NR'—) wherein the R radical represents a $C_1$-$C_4$ alkyl radical and R' represents a hydrogen or a $C_1$-$C_4$ alkyl radical;

a ureido radical (N(R)$_2$—CO—NR'—) wherein the R radicals, independently of one another, represent a $C_1$-$C_4$ alkyl radical, and R' represents a hydrogen or a $C_1$-$C_4$ alkyl radical;

an alkylsulphonylamino radical (RSO$_2$—NR'—) wherein the R radical represents a $C_1$-$C_4$ alkyl radical, and R' represents a hydrogen or a $C_1$-$C_4$ alkyl radical;

a hydroxycarbonyl radical;

a $C_1$-$C_4$ alkoxycarbonyl radical;

a cyano radical;

an optionally substituted phenyl radical; or an optionally substituted benzyl radical;

the $R_6$ and $R_7$ radicals, which may be identical or different, represent, independently of one another:

a hydrogen atom;

an optionally substituted $C_1$-$C_{16}$ alkyl radical, optionally interrupted by at least one heteroatoms and/or by at least one group comprising at least one heteroatom; with the proviso that the alkyl radical does not comprise any nitro, nitroso, peroxo or diazo functional groups;

an (alkoxy)aryl radical (-Ph-OR) wherein the R radical represents a hydrogen or a $C_1$-$C_4$ alkyl radical;

a (di)(alkyl)aminoaryl radical (-Ph-N(R)$_2$) wherein the R radicals, independently of one another, represent a hydrogen or a $C_1$-$C_4$ alkyl radical optionally substituted by a hydroxyl;

an alkylsulphonyl radical (RSO$_2$—) wherein the R radical represents a $C_1$-$C_4$ alkyl radical;

an aminocarbonyl radical, a (di)($C_1$-$C_4$)alkylaminocarbonyl radical;

a CH$_3$CO— radical;

a phenyl; or a benzyl optionally substituted by at least one hydroxyl and/or amino group;

wherein the $R_6$ and $R_7$ radicals can optionally form with the nitrogen atom to which they are attached, a saturated or unsaturated, optionally substituted heterocycle comprising from 5 to 7 ring members, optionally comprising another heteroatom which may be identical to or different from nitrogen;

wherein one of the $R_6$ or $R_7$ radicals can also form with the nitrogen atom to which it is attached and with an $R_2$ radical located in the ortho position with respect to the NR$_6$R$_7$ group, a substituted or unsubstituted, saturated or unsaturated heterocycle comprising 5 or 6 ring members;

wherein the $R_6$ and $R_7$ radicals can form with the nitrogen atom to which they are attached and each with an $R_2$ radical located in the ortho position with respect to the NR$_6$R$_7$ group, a substituted or unsubstituted, saturated or unsaturated heterocycle comprising 5 or 6 ring members;

n is an integer ranging from 1 to 4, wherein when n is below 4, the unsubstituted carbon atom or atoms bear(s) a hydrogen atom;

n' is an integer ranging from 1 to 4, wherein when n' is below 4, the unsubstituted carbon atom or atoms bear(s) a hydrogen atom;

the electroneutrality of the compounds of formulae (I) and/or (II) being ensured by at least one cosmetically acceptable anion An, which may be identical or different.

9. A method for preparing at least one monocationic monochromophoric entity comprising one hydrazone entity, wherein the at least one monocationic monochromophoric entity comprising one hydrazone entity is chosen from those of formulae (I) and (II)

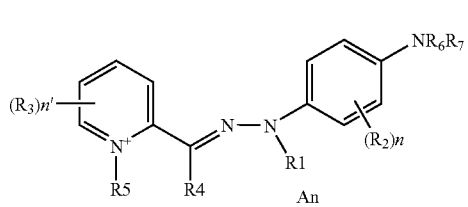

(I)

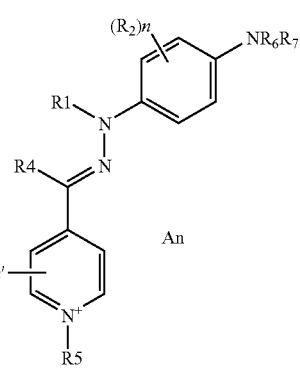

(II)

the mesomeric forms, addition salts with an acid, and/or solvates thereof, comprising:

(a) Condensing a heteroaromatic aldehyde or ketone with a hydrazine derivative according to the following reaction:

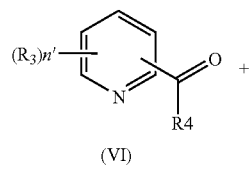

(VI)

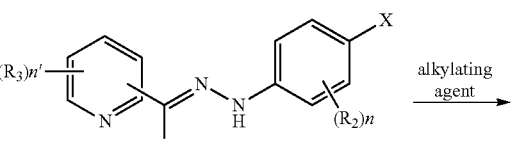

(VIII)

x = I, Br, Cl (b) Quaternizing the heterocyclic ring of formula (VIII) according to the following reaction:

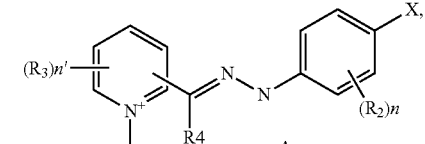

(IX)

x = I, Br, Cl (c) Aminating formula (IX) according to the following reaction:

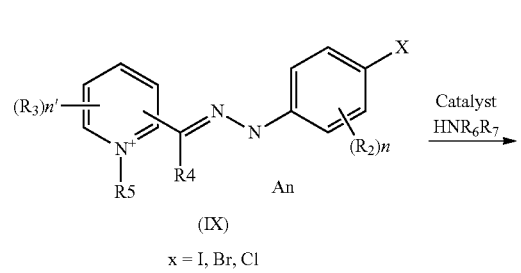

(X)

or (XI)

and (d) Alkylating formula (X) or (XI) according to the following reaction:

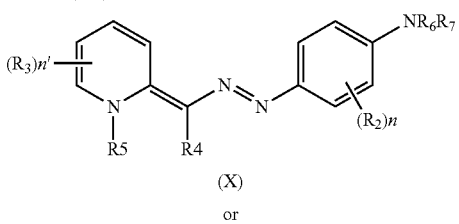

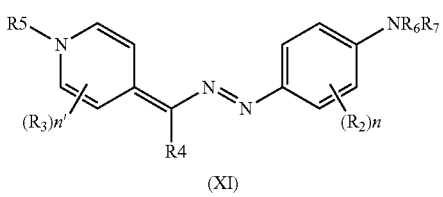

(I) or (II)

wherein, in formulae I and II:
  the $R_1$ radicals, which may be identical or different, represent, independently of one another:
    a hydrogen;
    an optionally substituted $C_1$-$C_{20}$ alkyl radical, optionally interrupted by at least one heteroatom and/or by at least one group comprising at least one heteroatom; with the proviso that the alkyl radical does not comprise any nitro, nitroso, peroxo or diazo functional groups;
    an optionally substituted phenyl radical;
    an optionally substituted benzyl radical;
    an alkylcarbonyl radical (R—CO—) wherein R represents a $C_1$-$C_4$ alkyl radical;
    an alkylsulphonyl radical ($RSO_2$—) wherein R represents a $C_1$-$C_4$ alkyl radical;
    an arylsulphonyl radical ($R'SO_2$—) wherein R' represents an optionally substituted phenyl or benzyl radical;
    a (di)(alkyl)aminosulphonyl radical (($R)_2N$—$SO_2$—) wherein the R radicals independently represent a hydrogen or a $C_1$-$C_4$ alkyl radical; or
    a (di)(alkyl)aminocarbonyl radical (($R)_2N$—CO—) wherein the R radicals independently represent a hydrogen or a $C_1$-$C_4$ alkyl radical;
  the $R_5$ radicals, which may be identical or different, represent, independently of one another:
    an optionally substituted $C_1$-$C_{20}$ alkyl radical, optionally interrupted by at least one heteroatom and/or by at least one group comprising at least one heteroatom; with the proviso that the alkyl radical does not comprise any nitro, nitroso, peroxo or diazo functional groups;
    a trimethylsilyl($C_1$-$C_4$)alkyl radical;
    an optionally substituted phenyl radical; or
    an optionally substituted benzyl radical;
  the $R_2$ and $R_3$ radicals, which may be identical or different, represent, independently of one another:
    a halogen atom;
    an optionally substituted $C_1$-$C_{16}$ alkyl radical, optionally interrupted by at least one heteroatom and/or by at least one groups comprising at least one heteroatom; with the proviso that the alkyl radical does not comprise any nitro, nitroso, peroxo or diazo functional groups;
    a hydroxyl radical;
    a $C_1$-$C_4$ alkoxy radical; a $C_2$-$C_4$ (poly)hydroxyalkoxy group;
    an alkoxycarbonyl radical (RO—CO—) wherein R represents a $C_1$-$C_4$ alkyl radical;
  an alkylcarbonyloxy radical (RCO—O) wherein R represents a $C_1$-$C_4$ alkyl radical;
    an optionally substituted aryloxy radical;
    an optionally substituted (di)arylamino radical;
    an amino radical optionally substituted by one or two $C_1$-$C_4$ alkyl radicals, which may be identical or different, optionally bearing at least one hydroxyl or $C_1$-$C_2$ alkoxy group, it being possible for said alkyl radicals to optionally form, with the nitrogen atom to which they are attached, a saturated or unsaturated, optionally substituted, optionally aromatic heterocycle having 5 or 7 ring members, optionally comprising another heteroatom which may be identical to or different from nitrogen;
    an alkylcarbonylamino radical (RCO—NR'—) wherein the R radical represents a $C_1$-$C_4$ alkyl radical and R' represents a hydrogen or a $C_1$-$C_4$ alkyl radical;
    a (di)(alkyl)aminocarbonyl group (($R)_2N$—CO—) wherein the R radicals, independently of one another, represent a hydrogen or a $C_1$-$C_4$ alkyl radical;
    a ureido radical (N($R)_2$—CO—NR'—) wherein the R radicals, independently of one another, represent a $C_1$-$C_4$ alkyl radical, and R' represents a hydrogen or a $C_1$-$C_4$ alkyl radical;
    a (di)(alkyl)aminosulphonyl radical (($R)_2N$—$SO_2$—) wherein the R radicals, independently of one another represent a hydrogen atom or a $C_1$-$C_4$ alkyl radical;
    an alkylthio radical (R—S—) wherein the R radical represents a $C_1$-$C_4$ alkyl radical;
    an alkylsulphonylamino radical ($RSO_2$—NR'—) wherein the R radical represents a $C_1$-$C_4$ alkyl radical, and the R' radical represents a hydrogen atom or a $C_1$-$C_4$ alkyl radical;
    a cyano radical (—C≡N);
    a phenyl radical;
    a trifluoromethyl radical (—$CF_3$);
    a thio (—SH) radical;
    an alkylsulphinyl radical (RSO—) wherein the R radical represents a $C_1$-$C_4$ alkyl radical; or
    an alkylsulphonyl radical ($RSO_2$—) wherein the R radical represents a $C_1$-$C_4$ alkyl radical;
  wherein $R_1$ can form with an $R_2$ radical located in the ortho position with respect to the $NR_1$ group and with the nitrogen atom substituted by $R_1$, a substituted or unsubstituted, saturated or unsaturated heterocycle comprising 5 or 6 ring members;
  wherein two adjacent $R_2$ radicals can form, with one another and with the carbon atoms to which they are attached, a substituted or unsubstituted, aromatic or non-aromatic (hetero)cyclic radical comprising 5 or 6 ring members;
  wherein two adjacent $R_3$ radicals can form, with one another and with the carbon atoms to which they are attached, a substituted or unsubstituted aromatic ring comprising 5 or 6 ring members;
  the $R_4$ radicals, which may be identical or different, represent, independently of one another:
    a hydrogen atom;
    an optionally substituted $C_1$-$C_{16}$ alkyl radical, optionally interrupted by at least one heteroatoms and/or by at least one group comprising at least one heteroatom; with the proviso that the alkyl radical does not comprise any nitro, nitroso, peroxo or diazo functional groups;
    an amino radical optionally substituted by one or two $C_1$-$C_4$ alkyl radicals, which may be identical or different, optionally bearing at least one hydroxyl or $C_1$-$C_2$ alkoxy group, it being possible for said alkyl radicals to optionally form, with the nitrogen atom to which they are attached, a saturated or unsaturated or aromatic, optionally substituted heterocycle having 5 or 6 ring members, optionally comprising at least one other heteroatom which may be identical to or different from nitrogen;
    an alkylcarbonylamino radical (RCO—NR'—) wherein the R radical represents a $C_1$-$C_4$ alkyl radical and R' represents a hydrogen or a $C_1$-$C_4$ alkyl radical;
    a ureido radical (N($R)_2$—CO—NR'—) wherein the R radicals, independently of one another, represent a $C_1$-$C_4$ alkyl radical, and R' represents a hydrogen or a $C_1$-$C_4$ alkyl radical;
    an alkylsulphonylamino radical ($RSO_2$—NR'—) wherein the R radical represents a $C_1$-$C_4$ alkyl radical, and R' represents a hydrogen or a $C_1$-$C_4$ alkyl radical;

a hydroxycarbonyl radical;

a $C_1$-$C_4$ alkoxycarbonyl radical;

a cyano radical;

an optionally substituted phenyl radical; or an optionally substituted benzyl radical;

the $R_6$ and $R_7$ radicals, which may be identical or different, represent, independently of one another:

a hydrogen atom;

an optionally substituted $C_1$-$C_{16}$ alkyl radical, optionally interrupted by at least one heteroatoms and/or by at least one group comprising at least one heteroatom; with the proviso that the alkyl radical does not comprise any nitro, nitroso, peroxo or diazo functional groups;

an (alkoxy)aryl radical (-Ph-OR) wherein the R radical represents a hydrogen or a $C_1$-$C_4$ alkyl radical;

a (di)(alkyl)aminoaryl radical (-Ph-N(R)$_2$) wherein the R radicals, independently of one another, represent a hydrogen or a $C_1$-$C_4$ alkyl radical optionally substituted by a hydroxyl;

an alkylsulphonyl radical (RSO$_2$—) wherein the R radical represents a $C_1$-$C_4$ alkyl radical;

an aminocarbonyl radical, a (di)($C_1$-$C_4$)alkylaminocarbonyl radical;

a CH$_3$CO— radical;

a phenyl; or a benzyl optionally substituted by at least one hydroxyl and/or amino group;

wherein the $R_6$ and $R_7$ radicals can optionally form with the nitrogen atom to which they are attached, a saturated or unsaturated, optionally substituted heterocycle comprising from 5 to 7 ring members, optionally comprising another heteroatom which may be identical to or different from nitrogen;

wherein one of the $R_6$ or $R_7$ radicals can also form with the nitrogen atom to which it is attached and with an $R_2$ radical located in the ortho position with respect to the $NR_6R_7$ group, a substituted or unsubstituted, saturated or unsaturated heterocycle comprising 5 or 6 ring members;

wherein the $R_6$ and $R_7$ radicals can form with the nitrogen atom to which they are attached and each with an $R_2$ radical located in the ortho position with respect to the $NR_6R_7$ group, a substituted or unsubstituted, saturated or unsaturated heterocycle comprising 5 or 6 ring members;

n is an integer ranging from 0 to 4, wherein when n is below 4, the unsubstituted carbon atom or atoms bear(s) a hydrogen atom;

n' is an integer ranging from 1 to 4, wherein when n' is below 4, the unsubstituted carbon atom or atoms bear(s) a hydrogen atom;

the electroneutrality of the compounds of formulae (I) and/or (II) being ensured by at least one cosmetically acceptable anion An, which may be identical or different.

10. A method for preparing at least one monocationic monochromophoric entity comprising one hydrazone entity, wherein the at least one monocationic monochromophoric entity comprising one hydrazone entity is chosen from those of formulae (I) and (II)

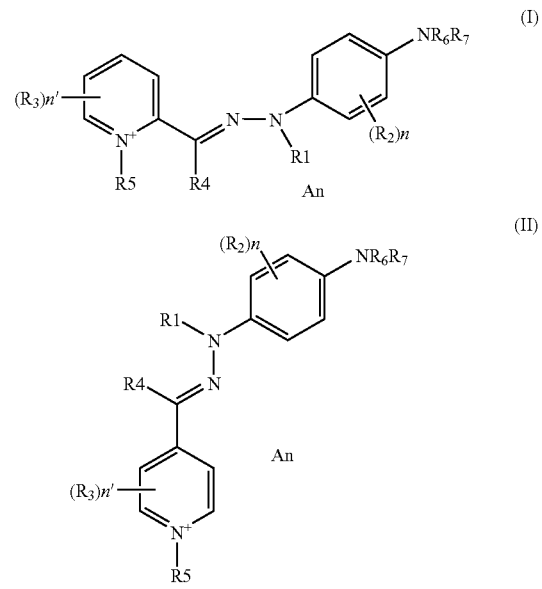

the mesomeric forms, addition salts with an acid, and/or solvates thereof, comprising:

(a) quaternizing formula (XII) according to the following reaction:

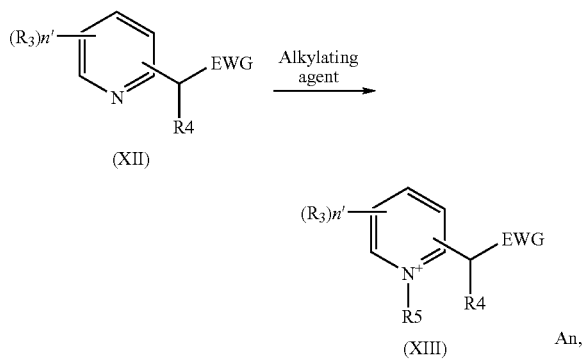

EWG = Electron-withdrawing group (b) coupling a diazonium salt to formula (XIII) according to the following reaction:

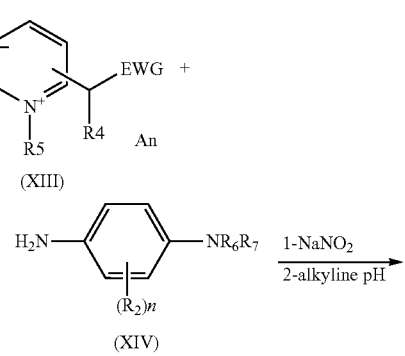

-continued

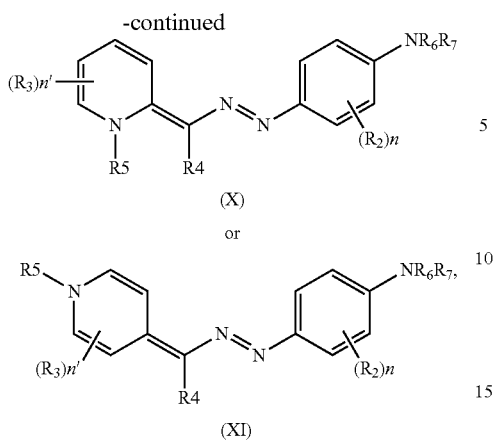

(X)

or (XI)

and (c) alkylating formula (X) or (XI) according to the following reaction:

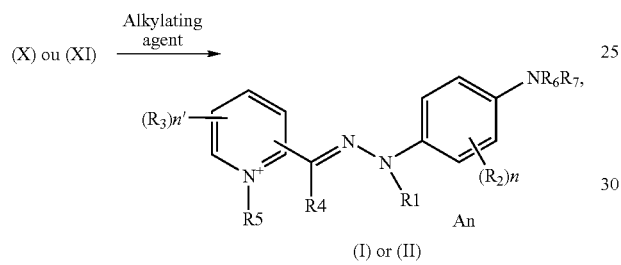

(I) or (II)

wherein, in formula I and II:

the $R_1$ radicals, which may be identical or different, represent, independently of one another:
  a hydrogen;
  an optionally substituted $C_1$-$C_{20}$ alkyl radical, optionally interrupted by at least one heteroatom and/or by at least one group comprising at least one heteroatom; with the proviso that the alkyl radical does not comprise any nitro, nitroso, peroxo or diazo functional groups;
  an optionally substituted phenyl radical;
  an optionally substituted benzyl radical;
  an alkylcarbonyl radical (R—CO—) wherein R represents a $C_1$-$C_4$ alkyl radical;
  an alkylsulphonyl radical (RSO$_2$—) wherein R represents a $C_1$-$C_4$ alkyl radical;
  an arylsulphonyl radical (R'SO$_2$—) wherein R' represents an optionally substituted phenyl or benzyl radical;
  a (di)(alkyl)aminosulphonyl radical ((R)$_2$N—SO$_2$—) wherein the R radicals independently represent a hydrogen or a $C_1$-$C_4$ alkyl radical; or
  a (di)(alkyl)aminocarbonyl radical ((R)$_2$N—CO—) wherein the R radicals independently represent a hydrogen or a $C_1$-$C_4$ alkyl radical;

the $R_5$ radicals, which may be identical or different, represent, independently of one another:
  an optionally substituted $C_1$-$C_{20}$ alkyl radical, optionally interrupted by at least one heteroatom and/or by at least one group comprising at least one heteroatom; with the proviso that the alkyl radical does not comprise any nitro, nitroso, peroxo or diazo functional groups;
  a trimethylsilyl($C_1$-$C_4$)alkyl radical;
  an optionally substituted phenyl radical; or
  an optionally substituted benzyl radical;

the $R_2$ and $R_3$ radicals, which may be identical or different, represent, independently of one another:
  a halogen atom;
  an optionally substituted $C_1$-$C_{16}$ alkyl radical, optionally interrupted by at least one heteroatom and/or by at least one groups comprising at least one heteroatom; with the proviso that the alkyl radical does not comprise any nitro, nitroso, peroxo or diazo functional groups;
  a hydroxyl radical;
  a $C_1$-$C_4$ alkoxy radical; a $C_2$-$C_4$ (poly)hydroxyalkoxy group;
  an alkoxycarbonyl radical (RO—CO—) wherein R represents a $C_1$-$C_4$ alkyl radical;
  an alkylcarbonyloxy radical (RCO—O) wherein R represents a $C_1$-$C_4$ alkyl radical;
  an optionally substituted aryloxy radical;
  an optionally substituted (di)arylamino radical;
  an amino radical optionally substituted by one or two $C_1$-$C_4$ alkyl radicals, which may be identical or different, optionally bearing at least one hydroxyl or $C_1$-$C_2$ alkoxy group, it being possible for said alkyl radicals to optionally form, with the nitrogen atom to which they are attached, a saturated or unsaturated, optionally substituted, optionally aromatic heterocycle having 5 or 7 ring members, optionally comprising another heteroatom which may be identical to or different from nitrogen;
  an alkylcarbonylamino radical (RCO—NR'—) wherein the R radical represents a $C_1$-$C_4$ alkyl radical and R' represents a hydrogen or a $C_1$-$C_4$ alkyl radical;
  a (di)(alkyl)aminocarbonyl group ((R)$_2$N—CO—) wherein the R radicals, independently of one another, represent a hydrogen or a $C_1$-$C_4$ alkyl radical;
  a ureido radical (N(R)$_2$—CO—NR'—) wherein the R radicals, independently of one another, represent a $C_1$-$C_4$ alkyl radical, and R' represents a hydrogen or a $C_1$-$C_4$ alkyl radical;
  a (di)(alkyl)aminosulphonyl radical ((R)$_2$N—SO$_2$—) wherein the R radicals, independently of one another represent a hydrogen atom or a $C_1$-$C_4$ alkyl radical;
  an alkylthio radical (R—S—) wherein the R radical represents a $C_1$-$C_4$ alkyl radical;
  an alkylsulphonylamino radical (RSO$_2$—NR'—) wherein the R radical represents a $C_1$-$C_4$ alkyl radical, and the R' radical represents a hydrogen atom or a $C_1$-$C_4$ alkyl radical;
  a cyano radical (—C≡N);
  a phenyl radical;
  a trifluoromethyl radical (—CF$_3$);
  a thio (—SH) radical;
  an alkylsulphinyl radical (RSO—) wherein the R radical represents a $C_1$-$C_4$ alkyl radical; or
  an alkylsulphonyl radical (RSO$_2$—) wherein the R radical represents a $C_1$-$C_4$ alkyl radical;

wherein $R_1$ can form with an $R_2$ radical located in the ortho position with respect to the $NR_1$ group and with the nitrogen atom substituted by $R_1$, a substituted or unsubstituted, saturated or unsaturated heterocycle comprising 5 or 6 ring members;

wherein two adjacent $R_2$ radicals can form, with one another and with the carbon atoms to which they are attached, a substituted or unsubstituted, aromatic or non-aromatic (hetero)cyclic radical comprising 5 or 6 ring members;
wherein two adjacent $R_3$ radicals can form, with one another and with the carbon atoms to which they are attached, a substituted or unsubstituted aromatic ring comprising 5 or 6 ring members;
the $R_4$ radicals, which may be identical or different, represent, independently of one another:
a hydrogen atom;
an optionally substituted $C_1$-$C_{16}$ alkyl radical, optionally interrupted by at least one heteroatoms and/or by at least one group comprising at least one heteroatom; with the proviso that the alkyl radical does not comprise any nitro, nitroso, peroxo or diazo functional groups;
an amino radical optionally substituted by one or two $C_1$-$C_4$ alkyl radicals, which may be identical or different, optionally bearing at least one hydroxyl or $C_1$-$C_2$ alkoxy group, it being possible for said alkyl radicals to optionally form, with the nitrogen atom to which they are attached, a saturated or unsaturated or aromatic, optionally substituted heterocycle having 5 or 6 ring members, optionally comprising at least one other heteroatom which may be identical to or different from nitrogen;
an alkylcarbonylamino radical (RCO—NR'—) wherein the R radical represents a $C_1$-$C_4$ alkyl radical and R' represents a hydrogen or a $C_1$-$C_4$ alkyl radical;
a ureido radical (N(R)$_2$—CO—NR'—) wherein the R radicals, independently of one another, represent a $C_1$-$C_4$ alkyl radical, and R' represents a hydrogen or a $C_1$-$C_4$ alkyl radical;
an alkylsulphonylamino radical (RSO$_2$—NR'—) wherein the R radical represents a $C_1$-$C_4$ alkyl radical, and R' represents a hydrogen or a $C_1$-$C_4$ alkyl radical;
a hydroxycarbonyl radical;
a $C_1$-$C_4$ alkoxycarbonyl radical;
a cyano radical;
an optionally substituted phenyl radical; or
an optionally substituted benzyl radical;
the $R_6$ and $R_7$ radicals, which may be identical or different, represent, independently of one another:
a hydrogen atom;
an optionally substituted $C_1$-$C_{16}$ alkyl radical, optionally interrupted by at least one heteroatoms and/or by at least one group comprising at least one heteroatom; with the proviso that the alkyl radical does not comprise any nitro, nitroso, peroxo or diazo functional groups;
an (alkoxy)aryl radical (-Ph-OR) wherein the R radical represents a hydrogen or a $C_1$-$C_4$ alkyl radical;
a (di)(alkyl)aminoaryl radical (-Ph-N(R)$_2$) wherein the R radicals, independently of one another, represent a hydrogen or a $C_1$-$C_4$ alkyl radical optionally substituted by a hydroxyl;
an alkylsulphonyl radical (RSO$_2$—) wherein the R radical represents a $C_1$-$C_4$ alkyl radical;
an aminocarbonyl radical, a (di)($C_1$-$C_4$)alkylaminocarbonyl radical;
a $CH_3CO$— radical;
a phenyl; or
a benzyl optionally substituted by at least one hydroxyl and/or amino group;
wherein the $R_6$ and $R_7$ radicals can optionally form with the nitrogen atom to which they are attached, a saturated or unsaturated, optionally substituted heterocycle comprising from 5 to 7 ring members, optionally comprising another heteroatom which may be identical to or different from nitrogen;
wherein one of the $R_6$ or $R_7$ radicals can also form with the nitrogen atom to which it is attached and with an $R_2$ radical located in the ortho position with respect to the $NR_6R_7$ group, a substituted or unsubstituted, saturated or unsaturated heterocycle comprising 5 or 6 ring members;
wherein the $R_6$ and $R_7$ radicals can form with the nitrogen atom to which they are attached and each with an $R_2$ radical located in the ortho position with respect to the $NR_6R_7$ group, a substituted or unsubstituted, saturated or unsaturated heterocycle comprising 5 or 6 ring members;
n is an integer ranging from 1 to 4, wherein when n is below 4, the unsubstituted carbon atom or atoms bear(s) a hydrogen atom;
n' is an integer ranging from 1 to 4, wherein when n' is below 4, the unsubstituted carbon atom or atoms bear(s) a hydrogen atom;
the electroneutrality of the compounds of formulae (I) and/or (II) being ensured by at least one cosmetically acceptable anion An, which may be identical or different.

* * * * *

UNITED STATES PATENT AND TRADEMARK OFFICE
CERTIFICATE OF CORRECTION

| | |
|---|---|
| PATENT NO. | : 8,012,220 B2 |
| APPLICATION NO. | : 12/296721 |
| DATED | : September 6, 2011 |
| INVENTOR(S) | : Hervé David, Nadègre Murguet and Andrew Greaves |

It is certified that error appears in the above-identified patent and that said Letters Patent is hereby corrected as shown below:

Claim 1, col. 98, line 1, insert -- , -- after "radical".

Claim 1, col. 100, line 11, "to which the are attached" should read -- to which they are attached --.

Claim 2, col. 102, line 17, insert "$R_1$," after -- substituted by --.

Claim 8, col. 113, line 8, "$((_R)_2N\text{-}SO_2\text{-})$" should read -- $((R)_2N\text{-}SO_2\text{-})$ --.

Claim 9, col. 119, line 52, "0-4" should read -- 1-4 --.

Signed and Sealed this
Sixth Day of December, 2011

David J. Kappos
*Director of the United States Patent and Trademark Office*